US007115205B2

(12) United States Patent
Robinson et al.

(10) Patent No.: US 7,115,205 B2
(45) Date of Patent: Oct. 3, 2006

(54) METHOD OF SIMULTANEOUS BLOOD COLLECTION AND SEPARATION USING A CONTINUOUS FLOW CENTRIFUGE HAVING A SEPARATION CHANNEL

(75) Inventors: Thomas C. Robinson, San Francisco, CA (US); Thomas P. Robinson, Encinitas, CA (US); Richard D'Elia, San Mateo, CA (US); Thomas Sahines, Milpitas, CA (US); Paul Eibe, Fremont, CA (US)

(73) Assignee: Mission Medical, Inc., Fresno, CA (US)

( * ) Notice: Subject to any disclaimer, the term of this patent is extended or adjusted under 35 U.S.C. 154(b) by 89 days.

(21) Appl. No.: 10/891,343

(22) Filed: Jul. 14, 2004

(65) Prior Publication Data

US 2004/0245189 A1    Dec. 9, 2004

Related U.S. Application Data

(62) Division of application No. 10/179,920, filed on Jun. 24, 2002, now Pat. No. 6,890,291.

(60) Provisional application No. 60/374,141, filed on Apr. 19, 2002, provisional application No. 60/300,873, filed on Jun. 25, 2001.

(51) Int. Cl.
*B01D 21/26* (2006.01)
*A61M 1/00* (2006.01)
*B04B 13/00* (2006.01)

(52) U.S. Cl. ............ 210/789; 210/739; 210/782; 210/787; 210/806; 494/1; 494/10; 494/23; 494/26; 494/27; 494/37; 494/43; 604/4.01; 604/5.01; 604/6.01; 604/6.02; 604/6.04; 604/6.09; 604/6.11; 604/6.15

(58) Field of Classification Search .......... 210/85, 210/86, 97, 103, 104, 109, 143, 782, 787, 210/789, 739, 744, 745, 806; 494/1, 2, 3, 494/10, 23, 26, 27, 43, 45; 604/4.01, 5.01, 604/6.01, 6.02, 6.04, 6.11, 6.15
See application file for complete search history.

(56) References Cited

U.S. PATENT DOCUMENTS

| 3,655,123 | A |   | 4/1972  | Judson et al. |
|-----------|---|---|---------|---------------|
| 3,957,197 | A | * | 5/1976  | Sartory et al. ............ 494/1 |
| 4,007,871 | A |   | 2/1977  | Jones et al. |
| 4,010,894 | A |   | 3/1977  | Kellogg et al. |
| 4,056,224 | A |   | 11/1977 | Lolachi |
| 4,086,924 | A |   | 5/1978  | Latham, Jr. |
| 4,091,989 | A |   | 5/1978  | Schlutz |
| 4,114,802 | A |   | 9/1978  | Brown |
| 4,285,464 | A |   | 8/1981  | Latham, Jr. |
| 4,303,193 | A |   | 12/1981 | Latham, Jr. |
| 4,304,357 | A |   | 12/1981 | Schoendorfer |

(Continued)

FOREIGN PATENT DOCUMENTS

AU    199718589    9/1997

(Continued)

*Primary Examiner*—John S. Kim
(74) *Attorney, Agent, or Firm*—Pillsbury Winthrop Shaw Pittman LLP

(57) ABSTRACT

A system for automatically collecting and separating whole blood into its components is described. The system includes a console, which contains all motors, pumps, sensors, valves and control circuitry, and a unique disposable set that includes a cassette supporting a centrifuge with an improved design, pump interfaces with an improved design, component and solution bags, and tubing. Various processes are implemented using a specific disposable set for each process which allows automatic identification of the process to be performed the console.

32 Claims, 53 Drawing Sheets

U.S. PATENT DOCUMENTS

| | | |
|---|---|---|
| 4,330,080 A | 5/1982 | Mathieu |
| 4,342,420 A | 8/1982 | Rosemeier et al. |
| 4,344,560 A | 8/1982 | Iriguchi et al. |
| 4,356,958 A | 11/1982 | Kolobow et al. |
| 4,379,452 A | 4/1983 | DeVries |
| 4,381,072 A | 4/1983 | Matsumoto et al. |
| 4,386,730 A | 6/1983 | Mulzet |
| 4,387,848 A | 6/1983 | Kellogg et al. |
| 4,416,654 A | 11/1983 | Schoendorfer et al. |
| 4,419,089 A | 12/1983 | Kolobow et al. |
| 4,439,178 A | 3/1984 | Mulzet |
| 4,447,221 A | 5/1984 | Mulzet |
| 4,464,167 A | 8/1984 | Schoendorfer et al. |
| 4,531,932 A | 7/1985 | Luppi et al. |
| 4,636,193 A | 1/1987 | Cullis |
| 4,637,813 A | 1/1987 | DeVries |
| 4,647,279 A | 3/1987 | Mulzet et al. |
| 4,668,214 A | 5/1987 | Reeder |
| 4,680,025 A | 7/1987 | Kruger et al. |
| 4,696,666 A | 9/1987 | Rice, Jr. |
| 4,708,712 A | 11/1987 | Mulzet |
| 4,710,161 A | 12/1987 | Takabayashi et al. |
| 4,734,089 A | 3/1988 | Cullis |
| 4,747,952 A | 5/1988 | Nakano et al. |
| 4,790,807 A | 12/1988 | Neumann et al. |
| 4,806,252 A | 2/1989 | Brown et al. |
| 4,834,890 A | 5/1989 | Brown et al. |
| 4,850,995 A | 7/1989 | Tie et al. |
| 4,897,185 A | 1/1990 | Schuyler et al. |
| 4,940,543 A | 7/1990 | Brown et al. |
| 4,985,153 A | 1/1991 | Kuroda et al. |
| 5,053,127 A | 10/1991 | Schoendorfer et al. |
| 5,076,911 A | 12/1991 | Brown et al. |
| 5,104,526 A | 4/1992 | Brown et al. |
| 5,147,290 A | 9/1992 | Jonsson |
| 5,186,844 A | 2/1993 | Burd et al. |
| 5,217,426 A | 6/1993 | Bacehowski et al. |
| 5,217,427 A | 6/1993 | Cullis |
| 5,217,618 A | 6/1993 | Murakoshi |
| 5,242,384 A | 9/1993 | Robinson et al. |
| 5,273,517 A | 12/1993 | Barone et al. |
| 5,281,342 A | 1/1994 | Biesel et al. |
| 5,298,016 A | 3/1994 | Gordon |
| 5,298,171 A | 3/1994 | Biesel |
| 5,311,908 A | 5/1994 | Barone et al. |
| 5,318,512 A | 6/1994 | Neumann |
| 5,322,620 A | 6/1994 | Brown et al. |
| 5,386,734 A | 2/1995 | Pusinelli |
| 5,387,187 A | 2/1995 | Fell et al. |
| 5,394,732 A | 3/1995 | Johnson et al. |
| 5,403,272 A | 4/1995 | Deniega et al. |
| 5,427,695 A | 6/1995 | Brown |
| 5,437,598 A | 8/1995 | Antwiler |
| 5,437,624 A | 8/1995 | Langley |
| 5,445,506 A | 8/1995 | Afflerbaugh et al. |
| 5,445,593 A | 8/1995 | Biesel et al. |
| 5,462,416 A | 10/1995 | Dennehey et al. |
| 5,478,479 A | 12/1995 | Herrig |
| 5,141,486 A | 1/1996 | Antwiler |
| 5,482,440 A | 1/1996 | Dennehey et al. |
| 5,494,578 A | 2/1996 | Brown et al. |
| 5,494,592 A | 2/1996 | Latham, Jr. et al. |
| 5,501,840 A | 3/1996 | Mantovani et al. |
| 5,514,069 A | 5/1996 | Brown et al. |
| 5,527,472 A | 6/1996 | Bellotti et al. |
| 5,547,453 A | 8/1996 | Di Perna |
| 5,549,834 A | 8/1996 | Brown |
| 5,571,068 A | 11/1996 | Bacehowski et al. |
| 5,573,678 A | 11/1996 | Brown et al. |
| 5,580,465 A | 12/1996 | Pall et al. |
| 5,581,687 A | 12/1996 | Lyle et al. |
| 5,607,579 A | 3/1997 | Latham, Jr. et al. |
| 5,607,830 A | 3/1997 | Biesel et al. |
| 5,614,106 A | 3/1997 | Payrat et al. |
| 5,628,915 A | 5/1997 | Brown et al. |
| 5,632,893 A | 5/1997 | Brown et al. |
| 5,637,082 A | 6/1997 | Pages et al. |
| 5,641,414 A | 6/1997 | Brown |
| 5,649,903 A | 7/1997 | Deniega et al. |
| 5,651,766 A | 7/1997 | Kingsley et al. |
| 5,653,887 A | 8/1997 | Wahl et al. |
| 5,658,240 A | 8/1997 | Urdahl et al. |
| 5,670,060 A | 9/1997 | Matkovich et al. |
| 5,686,238 A | 11/1997 | Martinson et al. |
| 5,693,232 A | 12/1997 | Brown et al. |
| 5,702,357 A | 12/1997 | Bainbridge et al. |
| 5,704,887 A | 1/1998 | Slowik et al. |
| 5,704,888 A | 1/1998 | Hlavinka et al. |
| 5,704,889 A | 1/1998 | Hlavinka et al. |
| 5,712,798 A | 1/1998 | Langley et al. |
| 5,720,716 A | 2/1998 | Blakeslee et al. |
| 5,722,946 A | 3/1998 | Mudloff et al. |
| 5,728,060 A | 3/1998 | Kingsley et al. |
| 5,730,883 A | 3/1998 | Brown |
| 5,733,253 A | 3/1998 | Headley et al. |
| 5,738,644 A | 4/1998 | Holmes et al. |
| 5,738,796 A | 4/1998 | Bormann et al. |
| 5,741,428 A | 4/1998 | Holm |
| 5,746,708 A | 5/1998 | Giesler et al. |
| 5,750,025 A | 5/1998 | Holmes et al. |
| 5,759,147 A | 6/1998 | Bacehowski et al. |
| 5,769,811 A | 6/1998 | Stacey et al. |
| 5,769,839 A | 6/1998 | Carmen et al. |
| 5,779,660 A | 7/1998 | Kingsley et al. |
| 5,783,085 A | 7/1998 | Fischel |
| 5,785,869 A | 7/1998 | Martinson et al. |
| 5,792,038 A | 8/1998 | Hlavinka |
| 5,792,372 A | 8/1998 | Brown et al. |
| 5,795,317 A | 8/1998 | Brierton et al. |
| 5,807,492 A | 9/1998 | Brown et al. |
| 5,817,042 A | 10/1998 | Langley et al. |
| 5,837,150 A | 11/1998 | Langley et al. |
| 5,849,203 A | 12/1998 | Brown et al. |
| 5,853,382 A | 12/1998 | Kingsley et al. |
| 5,865,785 A | 2/1999 | Bischof |
| 5,870,805 A | 2/1999 | Kandler et al. |
| 5,876,321 A | 3/1999 | Hlavinka et al. |
| 5,879,280 A | 3/1999 | Hlavinka et al. |
| 5,882,289 A | 3/1999 | Sakota et al. |
| 5,891,080 A | 4/1999 | Skinkle et al. |
| 5,904,645 A | 5/1999 | Hlavinka |
| 5,906,570 A | 5/1999 | Langley et al. |
| 5,913,768 A | 6/1999 | Langley et al. |
| 5,919,154 A | 7/1999 | Toavs et al. |
| 5,921,950 A | 7/1999 | Toavs et al. |
| 5,941,842 A | 8/1999 | Steele et al. |
| 5,956,023 A | 9/1999 | Lyle et al. |
| 5,961,842 A | 10/1999 | Min et al. |
| 5,980,757 A | 11/1999 | Brown et al. |
| 5,980,760 A | 11/1999 | Min et al. |
| 5,989,177 A | 11/1999 | West et al. |
| 5,996,634 A | 12/1999 | Dennehey et al. |
| 6,007,509 A | 12/1999 | Kingsley et al. |
| 6,022,306 A | 2/2000 | Dumont et al. |
| 6,027,657 A | 2/2000 | Min et al. |
| 6,051,147 A | 4/2000 | Bischof |
| 6,059,979 A | 5/2000 | Brown |
| 6,068,970 A | 5/2000 | Hosono et al. |
| 6,071,421 A | 6/2000 | Brown |
| 6,071,423 A | 6/2000 | Brown et al. |
| 6,099,491 A | 8/2000 | Headley et al. |
| 6,102,883 A | 8/2000 | Kingsley et al. |
| 6,113,554 A | 9/2000 | Gilcher et al. |
| 6,129,656 A | 10/2000 | Blakeslee et al. |

| | | |
|---|---|---|
| 6,135,940 A | 10/2000 | Walters |
| 6,179,801 B1 | 1/2001 | Holmes et al. |
| 6,186,752 B1 | 2/2001 | Deniega et al. |
| 6,196,987 B1 | 3/2001 | Holmes et al. |
| 6,197,579 B1 | 3/2001 | Van Vlasselaer et al. |
| 6,200,287 B1 | 3/2001 | Keller et al. |
| 6,228,017 B1 | 5/2001 | Brown |
| 6,231,537 B1 | 5/2001 | Holmes et al. |
| 6,241,649 B1 * | 6/2001 | Zanella et al. .................. 494/1 |
| 6,251,284 B1 * | 6/2001 | Bischof et al. ............. 210/739 |
| 6,254,784 B1 | 7/2001 | Nayak et al. |
| 6,261,065 B1 * | 7/2001 | Nayak et al. .................. 417/53 |
| 6,270,673 B1 | 8/2001 | Belt et al. |
| 6,277,060 B1 | 8/2001 | Neumann |
| 6,280,375 B1 | 8/2001 | Meisberger et al. |
| 6,280,406 B1 | 8/2001 | Dolecek et al. |
| 6,309,606 B1 | 10/2001 | Sitar |
| 6,315,707 B1 | 11/2001 | Smith et al. |
| 6,322,488 B1 | 11/2001 | Westberg et al. |
| 6,325,775 B1 | 12/2001 | Thom et al. |
| 6,334,842 B1 | 1/2002 | Hlavinka et al. |
| 6,344,020 B1 | 2/2002 | Reitz et al. |
| 6,348,156 B1 | 2/2002 | Vishnoi et al. |
| 6,379,322 B1 | 4/2002 | Kingsley et al. |
| 6,387,263 B1 | 5/2002 | Bhaskar et al. |
| 6,409,696 B1 | 6/2002 | Toavs et al. |
| 6,419,822 B1 | 7/2002 | Muller et al. |
| 6,440,372 B1 | 8/2002 | Pages |
| 6,451,203 B1 | 9/2002 | Brown |
| 6,464,624 B1 | 10/2002 | Pages |
| 6,475,175 B1 | 11/2002 | Rivera et al. |
| 6,481,980 B1 | 11/2002 | Vandlik et al. |
| 6,524,231 B1 | 2/2003 | Westberg et al. |
| 6,709,412 B1 * | 3/2004 | Vandlik et al. ............ 604/6.02 |
| 6,730,054 B1 * | 5/2004 | Pierce et al. ............... 604/6.01 |
| 6,790,195 B1 * | 9/2004 | Steele et al. ............... 604/6.02 |
| 2001/0000185 A1 | 4/2001 | Keller et al. |
| 2001/0037078 A1 | 11/2001 | Lynn et al. |
| 2002/0028155 A1 | 3/2002 | Dolecek et al. |
| 2002/0032398 A1 | 3/2002 | Steele et al. |
| 2002/0033370 A1 | 3/2002 | Bainbridge et al. |
| 2002/0062100 A1 | 5/2002 | Pierce et al. |
| 2002/0077241 A1 | 6/2002 | Odak et al. |
| 2002/0090319 A1 | 7/2002 | Vandlik et al. |
| 2002/0099319 A1 | 7/2002 | Saito et al. |
| 2002/0128582 A1 | 9/2002 | Farrell et al. |
| 2002/0128583 A1 | 9/2002 | Min et al. |
| 2002/0128584 A1 | 9/2002 | Brown et al. |
| 2002/0131891 A1 | 9/2002 | Smith et al. |
| 2002/0142909 A1 | 10/2002 | Sakota |
| 2003/0106861 A1 * | 6/2003 | Gibbs et al. ................ 210/806 |
| 2004/0236263 A1 * | 11/2004 | Van Waeg et al. ......... 604/5.01 |

FOREIGN PATENT DOCUMENTS

| | | |
|---|---|---|
| EP | 0 214 803 A2 | 8/1986 |
| EP | 0987039 A2 | 3/2000 |
| GB | 1 451 859 | 12/1974 |
| GB | 1 509 667 | 10/1976 |
| GB | 1 511 819 | 10/1976 |
| WO | WO 88/05691 | 8/1988 |
| WO | WO 89/00084 | 1/1989 |
| WO | WO 93/12888 | 7/1993 |
| WO | WO 94/08691 | 4/1994 |
| WO | WO 98/22165 | 5/1998 |

* cited by examiner

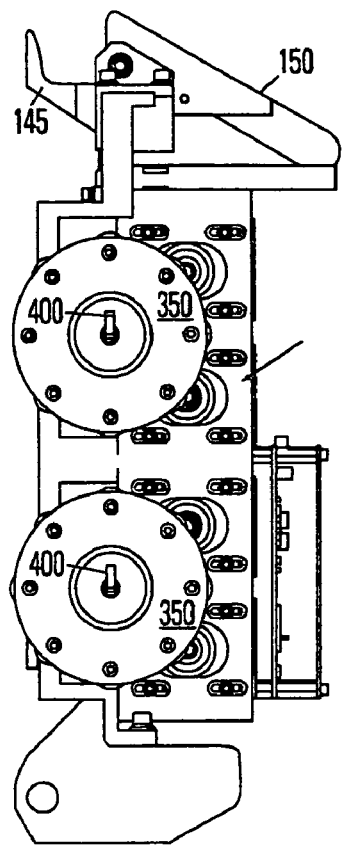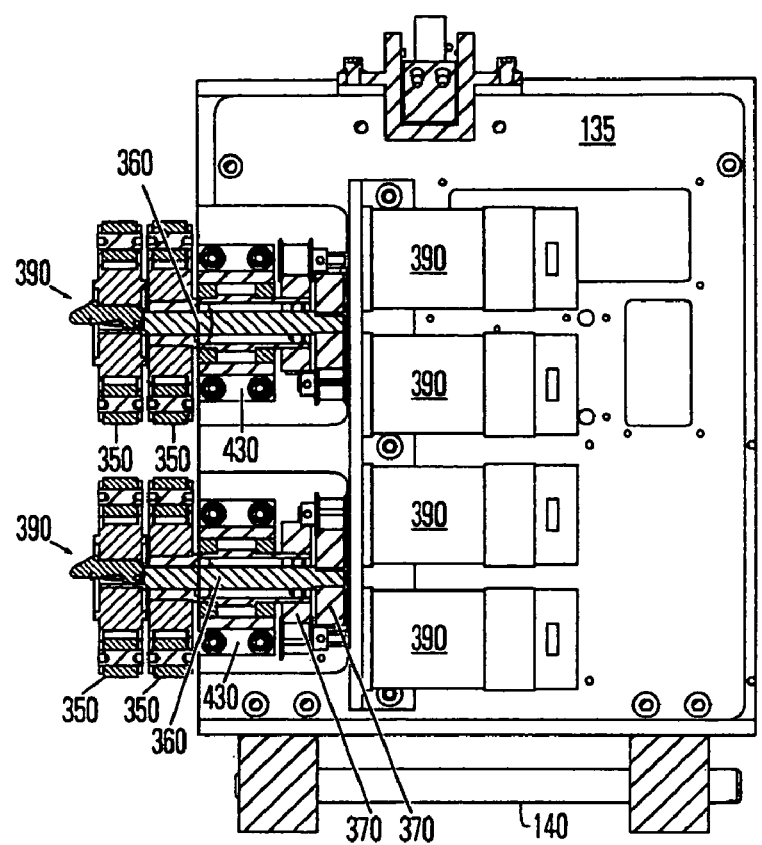
FIG. 9A  FIG. 9B

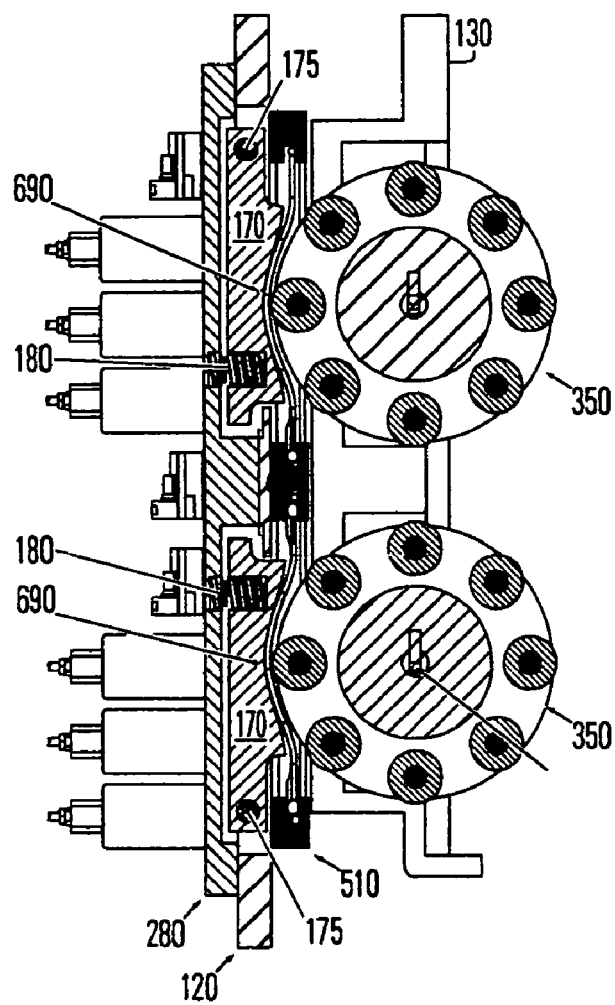 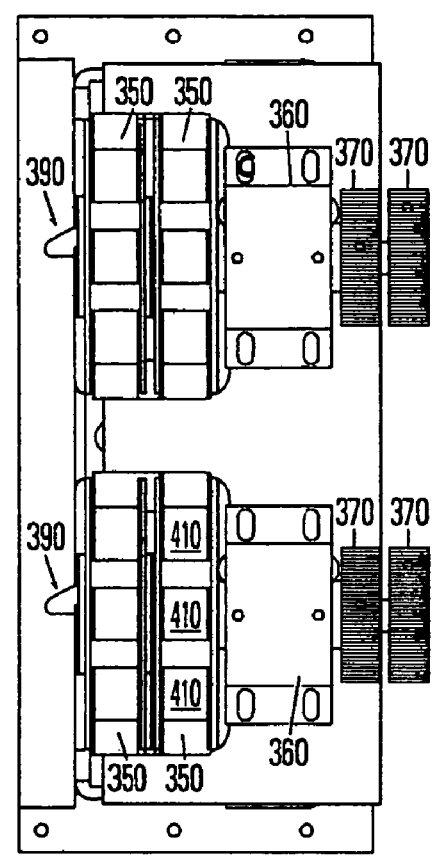
FIG. 10A  FIG. 10B

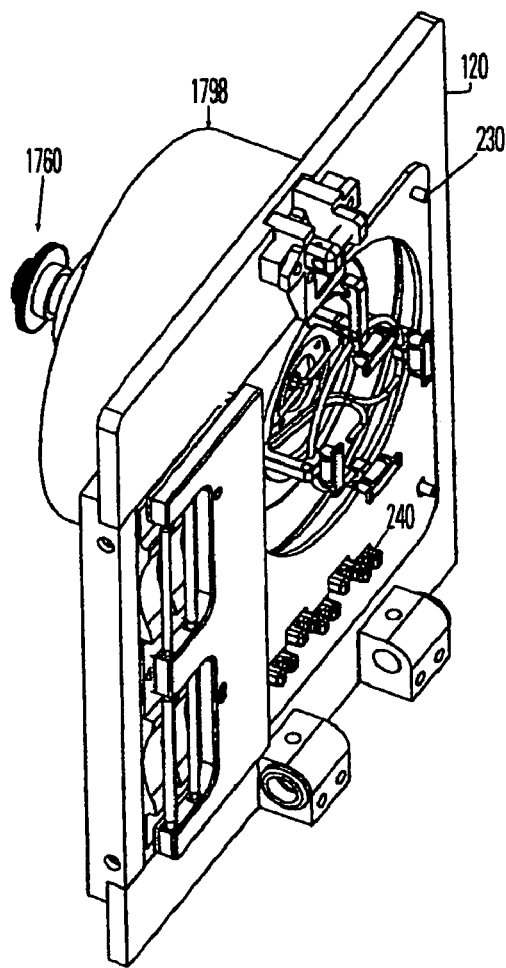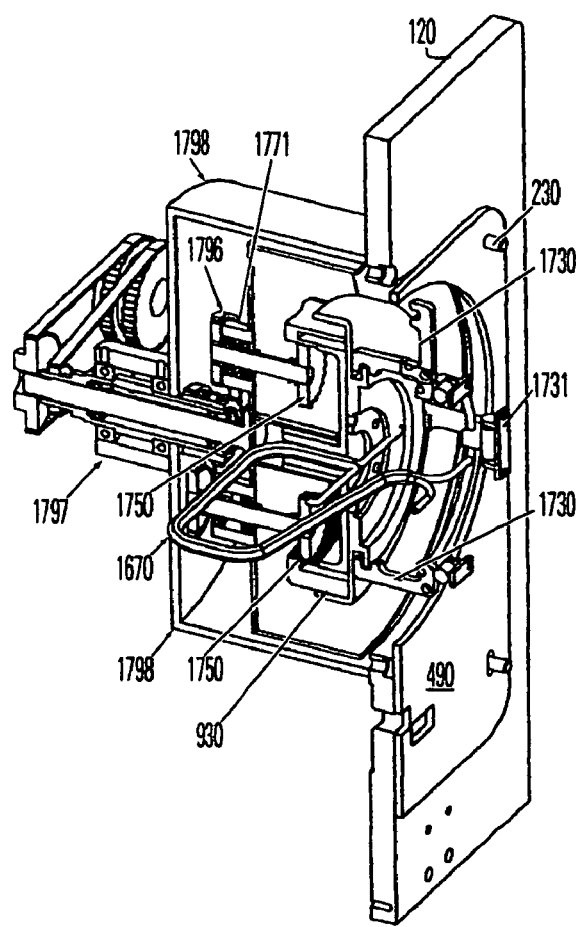
FIG. 28A  FIG. 28B

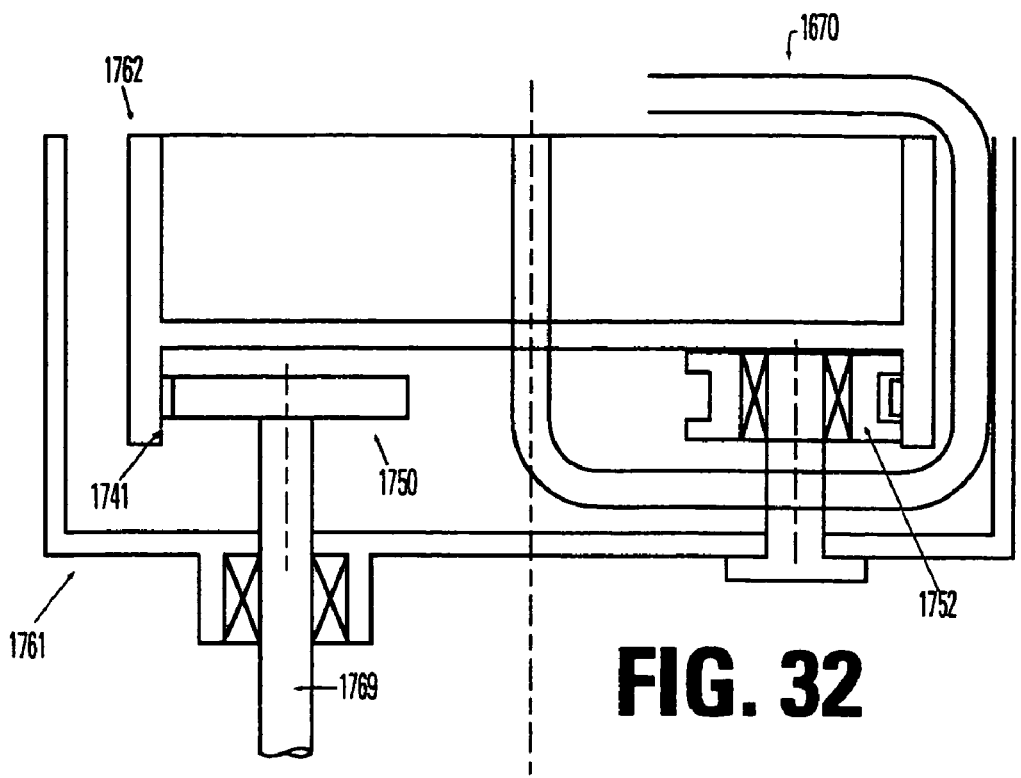
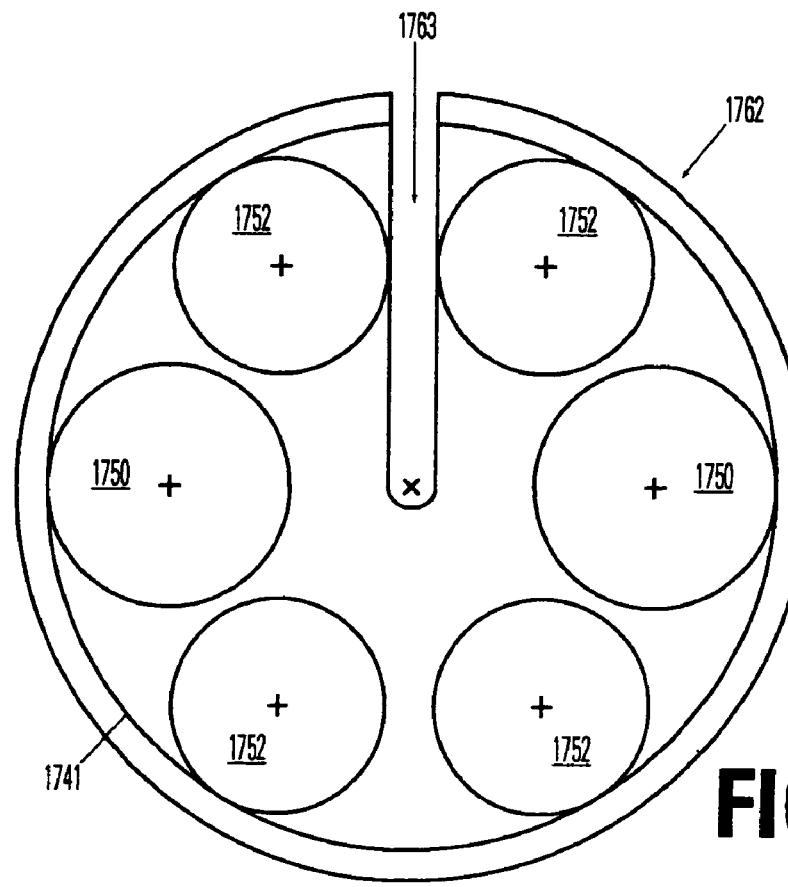

METHOD OF SIMULTANEOUS BLOOD COLLECTION AND SEPARATION USING A CONTINUOUS FLOW CENTRIFUGE HAVING A SEPARATION CHANNEL

CROSS REFERENCE TO RELATED APPLICATIONS

This application is a divisional of U.S. patent application Ser. No. 10/179,920, filed Jun. 24, 2002, now issued as U.S. Pat. No. 6,890,291. Additionally, this application claims the benefit of U.S. Provisional Patent Application No. 60/300,873, entitled Automated Whole Blood Collection and Separation System filed Jun. 25, 2001, and of U.S. Provisional Patent Application No. 60/374,141, filed Apr. 19, 2002, entitled Integrated Blood Collection and Processing Unit.

TECHNICAL FIELD

This invention relates generally to devices and methods for the automated collection of blood and separation of blood into its component parts.

BACKGROUND AND DESCRIPTION OF PRIOR ART

There are two basic methods currently used for blood collection and separation of blood into its component parts: a manual method and apheresis.

The current method of collecting and processing whole blood into its components (red cells, plasma, platelets) takes 75 to 90 minutes per unit. The process begins with the manual whole blood collection from a donor, which takes about 12 to 15 minutes. Then the unit of whole blood and test samples are transported to a fixed blood components laboratory where the whole blood is tested, centrifuged, expressed, labeled, leukoreduced, and placed into inventory. Further centrifugation and handling are required to produce platelets.

In the United States, collection of certain components are more frequently performed using apheresis. Apheresis is an automated process in which the donor blood is collected and stripped of a desired component. The remainder is then returned to the donor. For example, plateletpheresis is the automated removal of platelets from the body through the withdrawal of blood, its separation into red blood cells, plasma, and platelets, and the re-infusion of the red blood cells and plasma back into the body.

In general, manual methods of collection and separation of blood are less efficient than automated methods such as aphaeresis. For example, with the manual method of platelet collection six collections are required to produce a therapeutic dose.

Additionally, the regulatory climate and issues affecting the donor population would also appear to favor an alternative approaches to the current blood collection procedures including the standard manual collection and separation process.

Blood products are biological products, and blood centers must therefore operate under the United States Food and Drug Administration's (FDA) regulations and established practices. Operating in compliance with regulations and practices when utilizing manual collection and processing procedures imposes an enormous quality assurance burden, under which more than one-half of blood centers in the United States still fail to operate.

Moreover, new regulations are being proposed. For example, leukocytes have been identified to cause negative physiological reactions in a small percentage of blood transfusion recipients. As a result, the FDA's Blood Products Advisory Committee has formally recommended that the FDA mandate leukocyte reduction and nations around the world, including Canada and the United Kingdom, have adopted leukocyte filtering. Leukocytes are currently removed from red cells and platelets by manual filtration processes which are time consuming and labor intensive.

The donor population in the United States and elsewhere is expected to decline by approximately 8% from its level in 2002. The decline is anticipated for a variety of reasons, including more stringent donor screening to prevent contamination of the blood supply by various diseases. Some entities have proposed the collection of two red cell units during one donor session as a partial solution to supply problems. One study has suggested that the adoption of double red cell collection could reduce the required donor pool by 6% and continue to meet existing blood supply requirements from a smaller donor pool. However, many blood banks currently do not have the capacity to perform double red cell collection.

Although, clearly, manual processes for blood collection and separation have some serious disadvantages, they are generally far less expensive than the automated alternatives, such as aphaeresis, as they do not require specialized staff, expensive equipment and disposables. Additionally, the cumbersome apheresis equipment does not lend itself to use at mobile collection sites, where the majority of blood donations are collected. In part for these reasons, although apheresis is used extensively for certain procedures, such as platelet collection where up to sixty-five percent of platelets collected in the United States are collected using plateletpheresis, apheresis has not achieved high penetration or displaced the current manual processes for blood collection and separation. Similarly, double unit collection has not been implemented in part because current procedures for double unit collection are expensive and relatively complex. Finally, for some procedures, such as leukocyte filtering, there are few, if any, alternatives to a time consuming and expensive manual process.

It is therefore an object of this invention to provide an apparatus and system for blood collection that reduces direct collection and processing costs. It is a further object of this invention to automate and standardize collection and processing procedures, and to automate data collection to minimize errors. It is a further object of this invention to have an automated system of blood collection that has the capacity to perform multiple collection processes including the collection of both single and double units of red blood cells. It is a further object of this invention to provide a system that can perform all processes at remote sites on mobile blood drives as well as at fixed, blood center sites. And, it is an object of this invention to simultaneously collect, process, and leukofilter blood.

SUMMARY OF THE INVENTION

The present invention comprises a console or electromechanical instrument that may be used to perform several different blood collection and separation processes. The console is a small, compact apparatus that has the various actuation pumps and valves and sensing pressure transducers, ultrasonic detectors, and other devices needed to implement the process using a closed, sterile disposable set. The invention further comprises a different disposable set for each process that is specifically designed to implement that process and to contain all associated blood and fluids. As many functions and devices as possible are placed in the console, allowing simplification and reduction in size of the disposable set.

The disposable system includes a cassette to integrate, locate, and support all disposable set components that interact with the console actuation and sensing components. The disposable set components interact automatically with their interactive console components without significant influence by or dependence on the user.

The console uses micro-processor based electronics and software to select and control a variety of different processes. The console identifies the cassette installed in it by reading a bar code on the cassette. The microprocessor then initiates the process appropriate for that cassette, with user verification. Automated data collection by the console plus bar code scanning by the user eliminates manual entries and allows error-free data to be provided to a blood center computer.

In addition to identifying the process to be implemented by the console, the bar code also identifies the cassette lot number and expiration date, along with other cassette information. It provides calibration values for the pumps and other devices in the console. Since pump tubing inside diameter is variable, a calibration based on the tubing diameter for each pump tube in each cassette improves pump flow accuracy. These calibrations ensure maximum accuracy of actuators and sensors.

Other features of the invention include a low-cost manifold as part of the disposable set that contains the actuation and sensing components, and a simple, low-cost, continuous-flow centrifuge assembly with unique features that increase its efficiency.

BRIEF DESCRIPTION OF THE DRAWINGS

FIGS. 9A and 9B are views of the door showing the attachment of the rotors.
FIGS. 10A and 10B are views of the pump rotors, manifold pump tubing and rotor tracks.

FIGS. 28A and 28B are views of the continuous centrifuge disk with an umbilical with the cassette mounted to the front panel of the console.
FIG. 32 is a conceptual representation of an alternative umbilical design.
FIG. 33 is a conceptual representation of the gear and bearing arrangement of the embodiment of the umbilical continuous flow centrifuge shown in FIG. 32.

DETAILED DESCRIPTION OF THE DRAWINGS

Console

Figure 1:
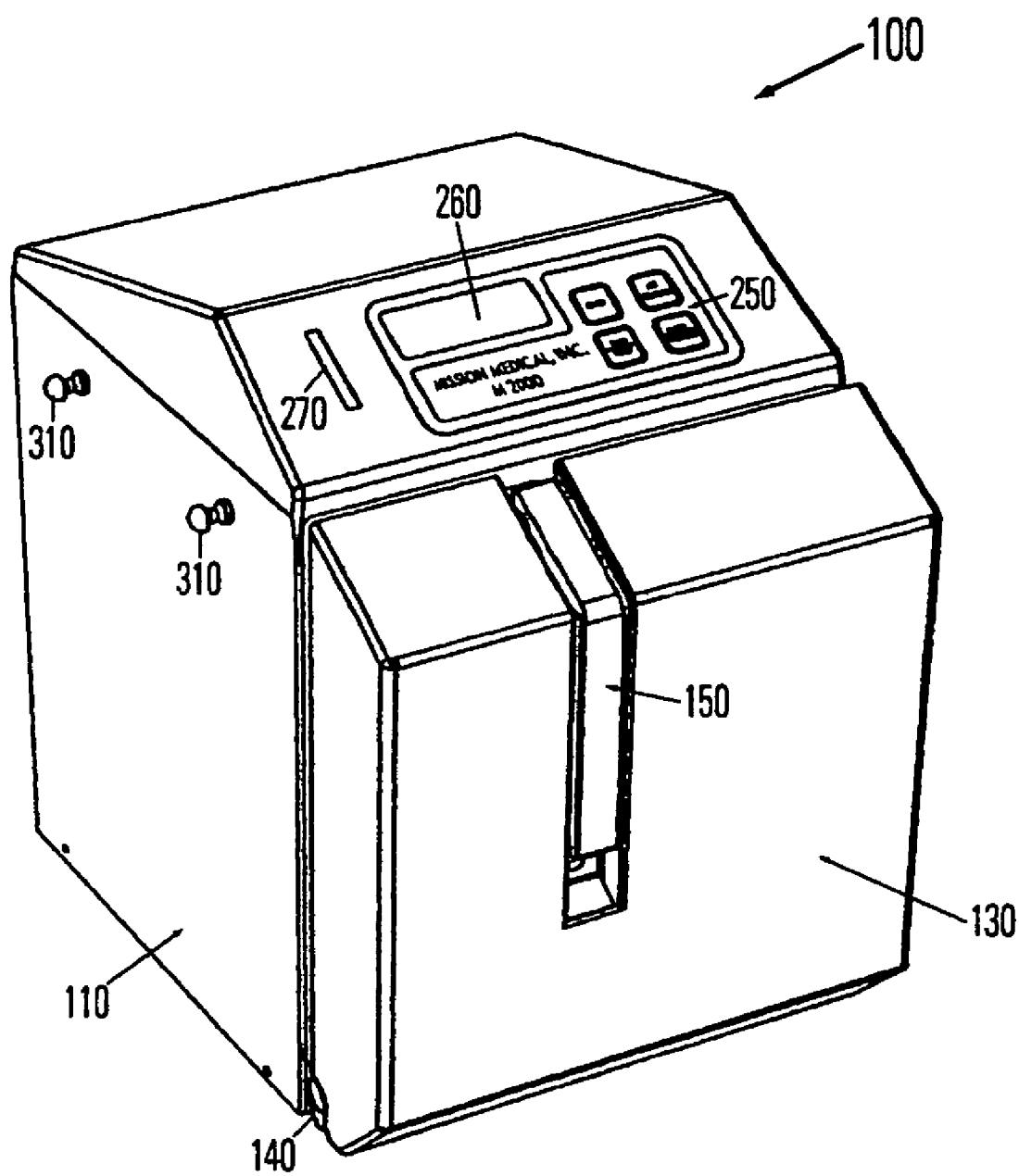
FIG. 1 is a perspective view of the console.
Figure 2:
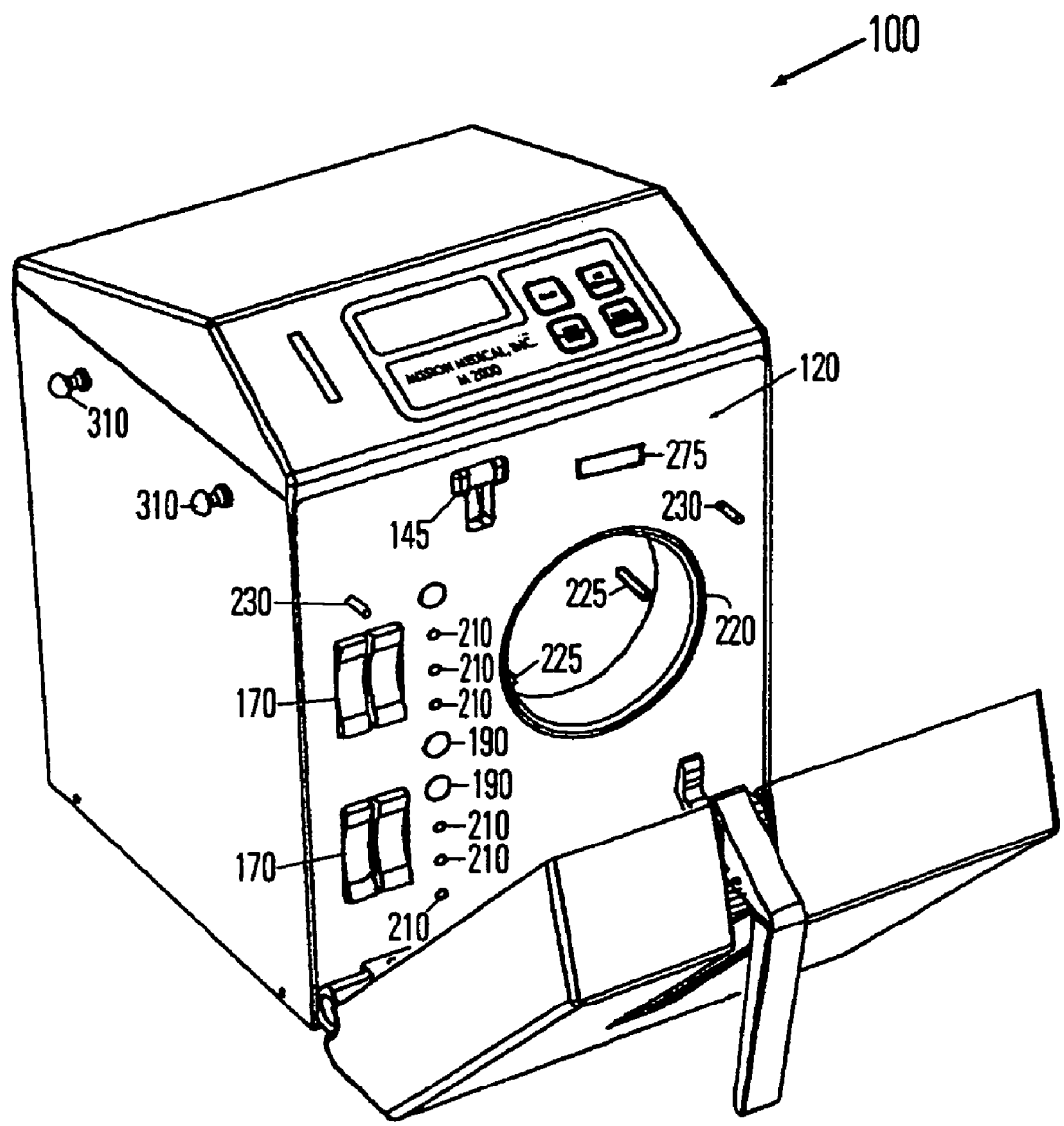
FIG. 2 is a perspective view of the console with the door open.
Figure 3:
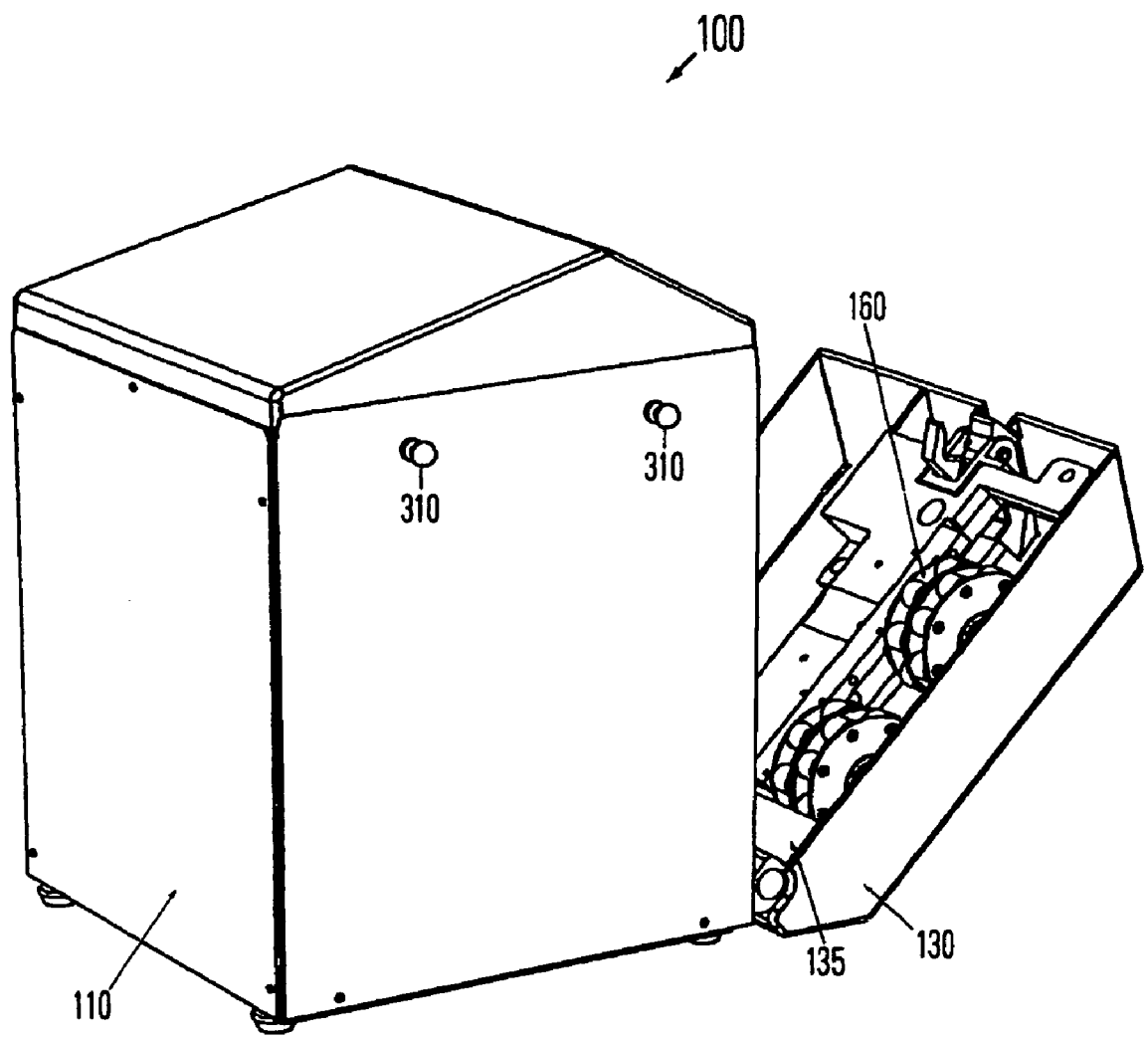
FIG. 3 is a perspective view of the console from the rear showing the interior of the open console door.
Figure 4:
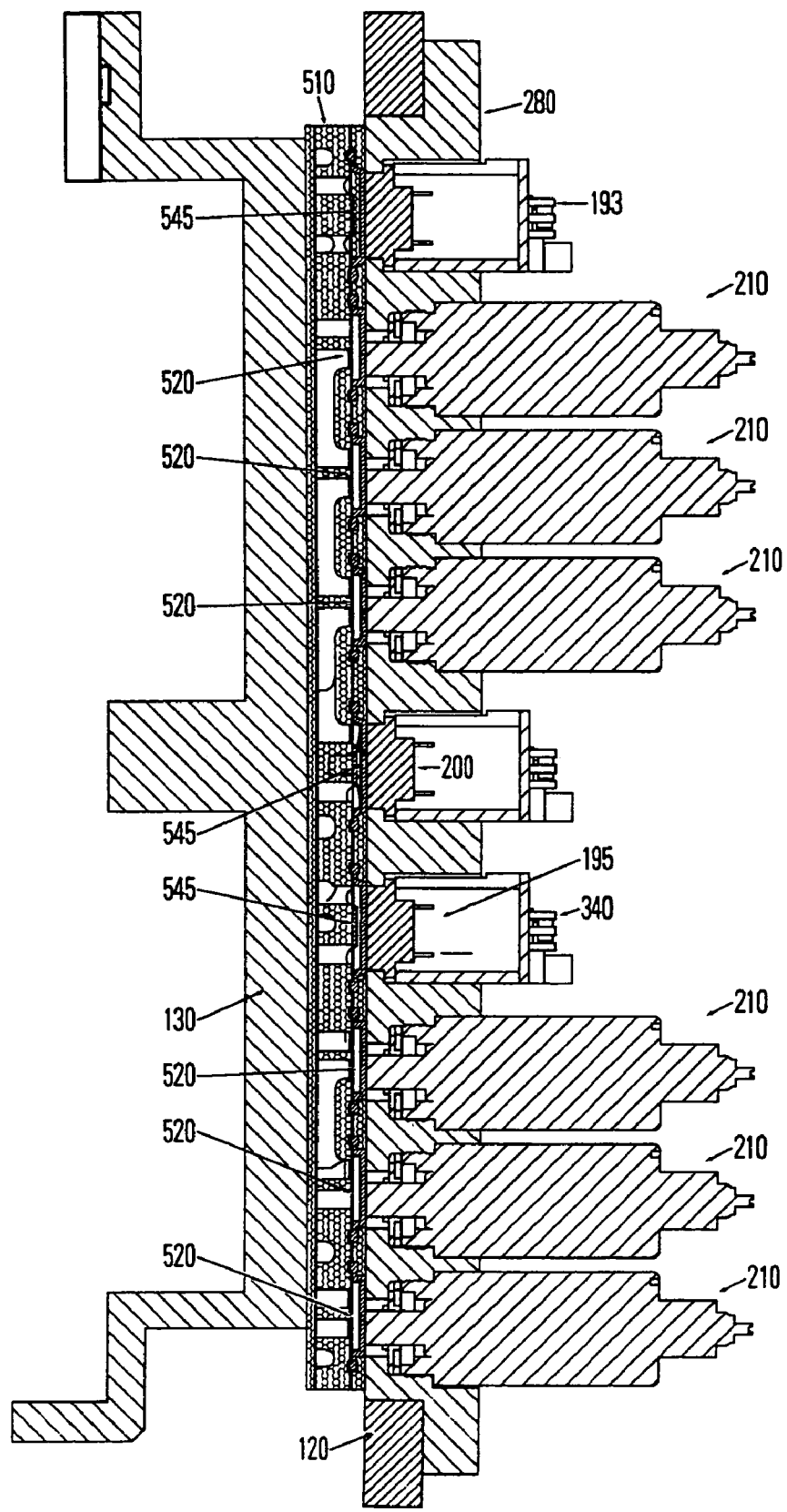
FIG. 4 is a cutaway view of the valve plate assembly.
Figure 21A:
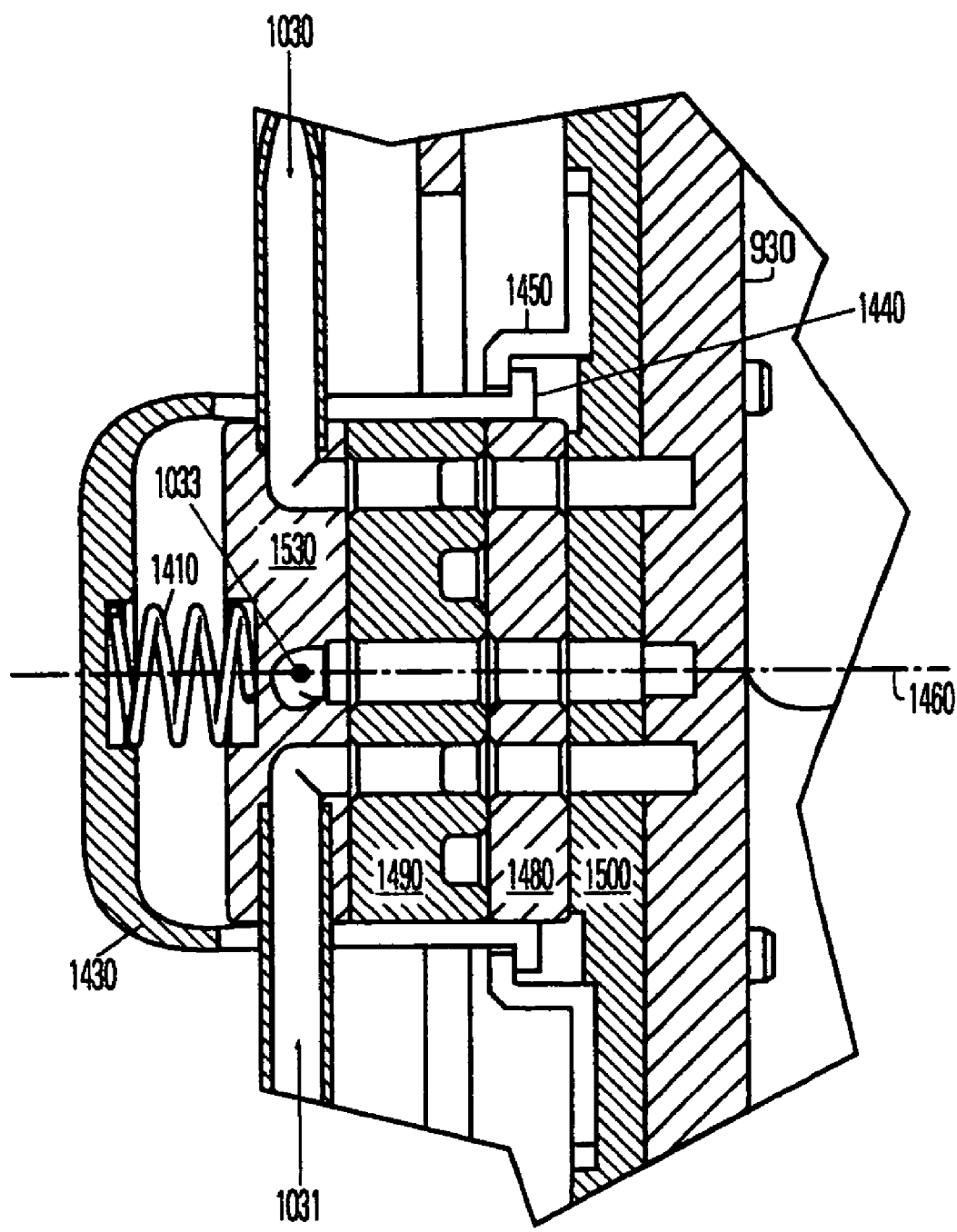
FIGS. 21A and 21B show the conceptual design and operation of the continuous flow centrifuge that uses a face seal.
Figure 21B:
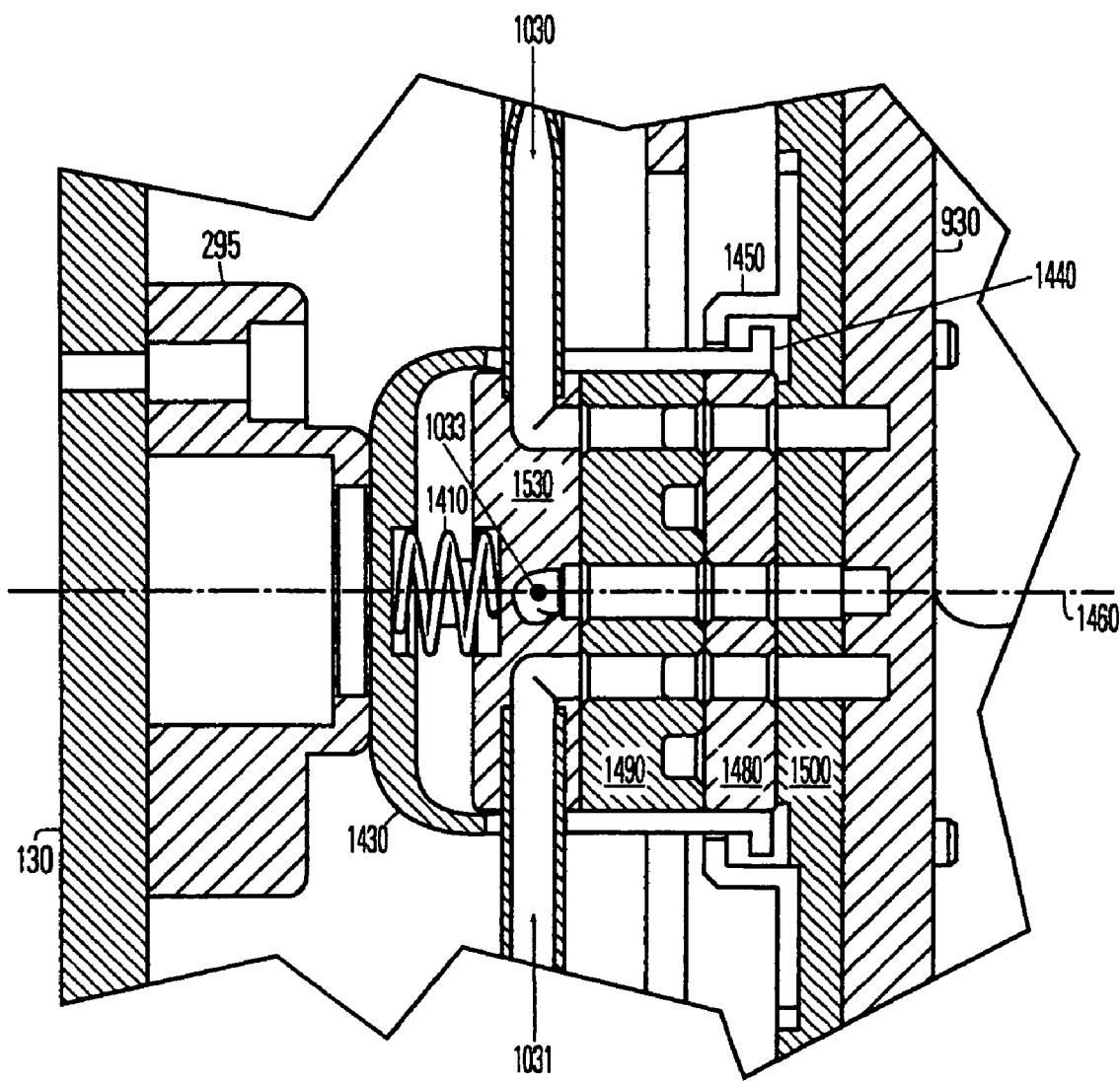
Figure 23:
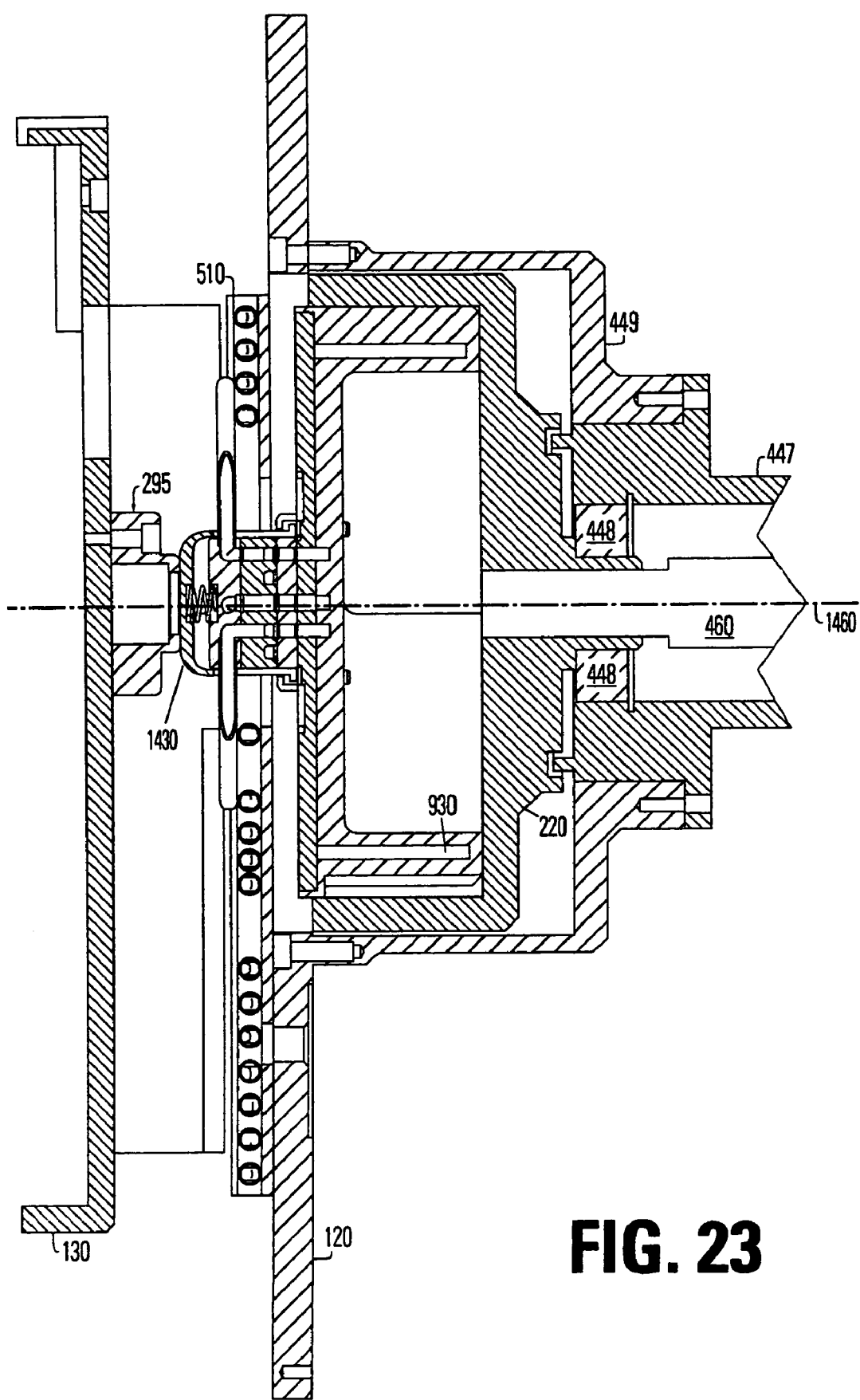
FIG. 23 shows the continuous flow centrifuge that uses a face seal as mounted for operation in the centrifuge cup in the console.

With reference to FIGS. 1, 2 and 3, the system includes a console 100 having a console body 110 enclosing electronic, electromechanical, and mechanical components. A console door 130, is connected to the front panel 120 of the console body 110 using a hinge 140 along the front horizontal bottom of the front panel 120. The door may also include a door plunger 295 shown in FIGS. 21B and 23, which interacts with certain designs of a centrifuge element on the disposable set as further described below. A latch 145 secures and positions the console door to the front panel 120 at the top and may be operated through the use of a handle 150 on the door. Hangers 310 on the outside of the console 100 may be used to hold solution and blood product bags 580, 590 which are part of a disposable set 480 shown in FIGS. 15 and 16. Four roller pumps 160 and their drive mechanisms are shown as mounted on the inside of the door 130. Power may be provided to the system from alternating current sources and/or direct current sources such as batteries (not shown) to allow for portability.

Figure 15:
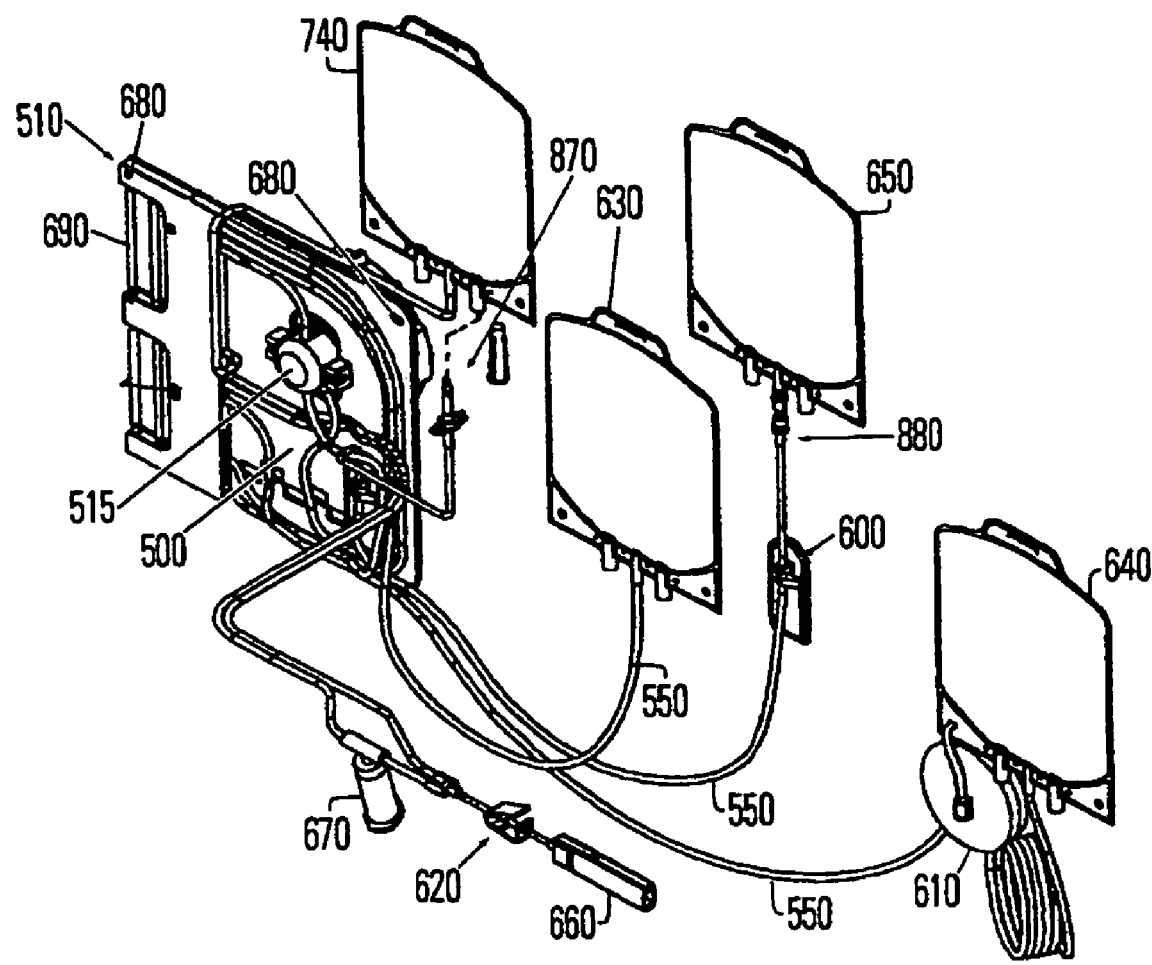
FIG. 15 is a second view of the disposable set.
Figure 16:
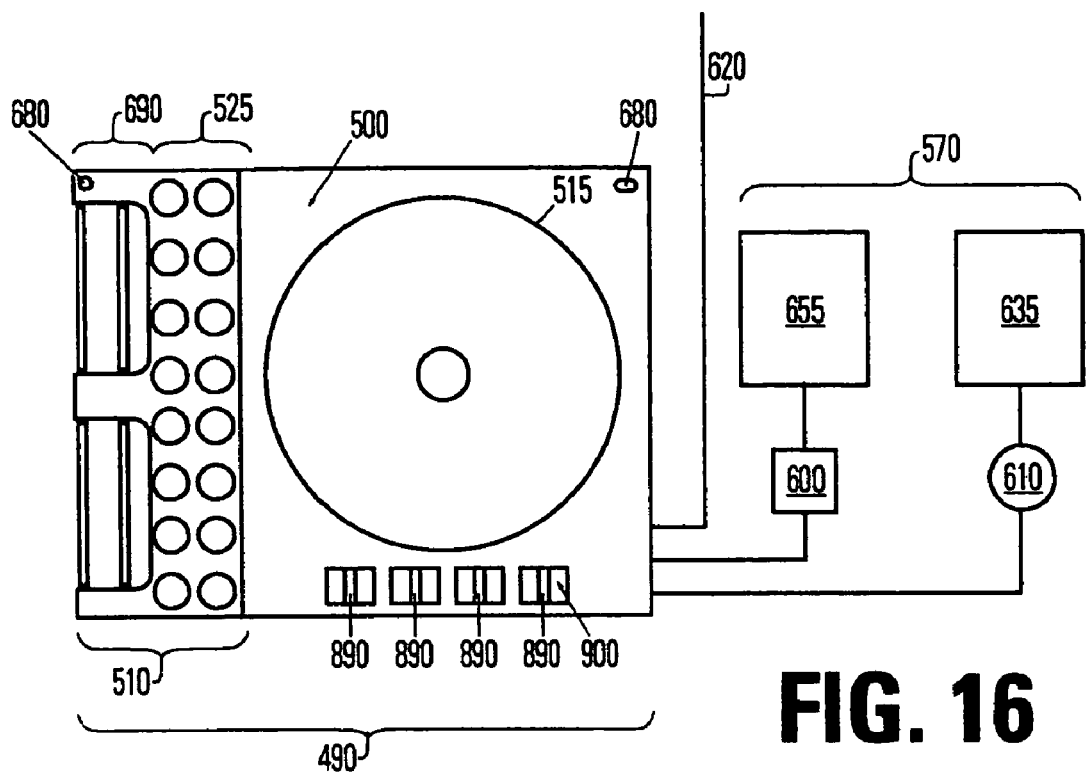
FIG. 16 is a conceptual view of the cassette.

With reference to FIGS. 2, 4, 5 and 6 the substantially vertical front panel 120 of the console locates and positions roller pump tracks 170, pressure transducers 190, valves, which may be solenoid valve actuators 210 as shown, a centrifuge drive cup 220, ultrasonic sensors 240, and pins 230 from which to hang a disposable cassette 490, which is further described below in connection with FIGS. 15 and 16. The valve actuators 210 and positive pressure transducers 193, 195, and negative pressure transducer 200 are mounted to a valve plate 280 that is part of and attached to the console front panel 120. Valve actuators 210, including a washer 320 and seal 330, are mounted on the valve plate 280 and front panel 120 so as to be opposite valve components 520 in the cassette 490 of the disposable set 480.

Placement of the roller pump and drive mechanisms on the door with valves and sensors in the console body may allow for a more compact cassette design as the roller pump and drive mechanisms do not compete for space on the console front panel with the valves, sensors and other elements. However, as alternatives to the design shown and described, the roller pumps and drive mechanisms may be placed in the console on the front panel 120, and/or the valves 210 and pressure transducers 190 and/or other components may be placed on the interior of the door, with appropriate modifications to the design of the disposable set.

Figure 6:
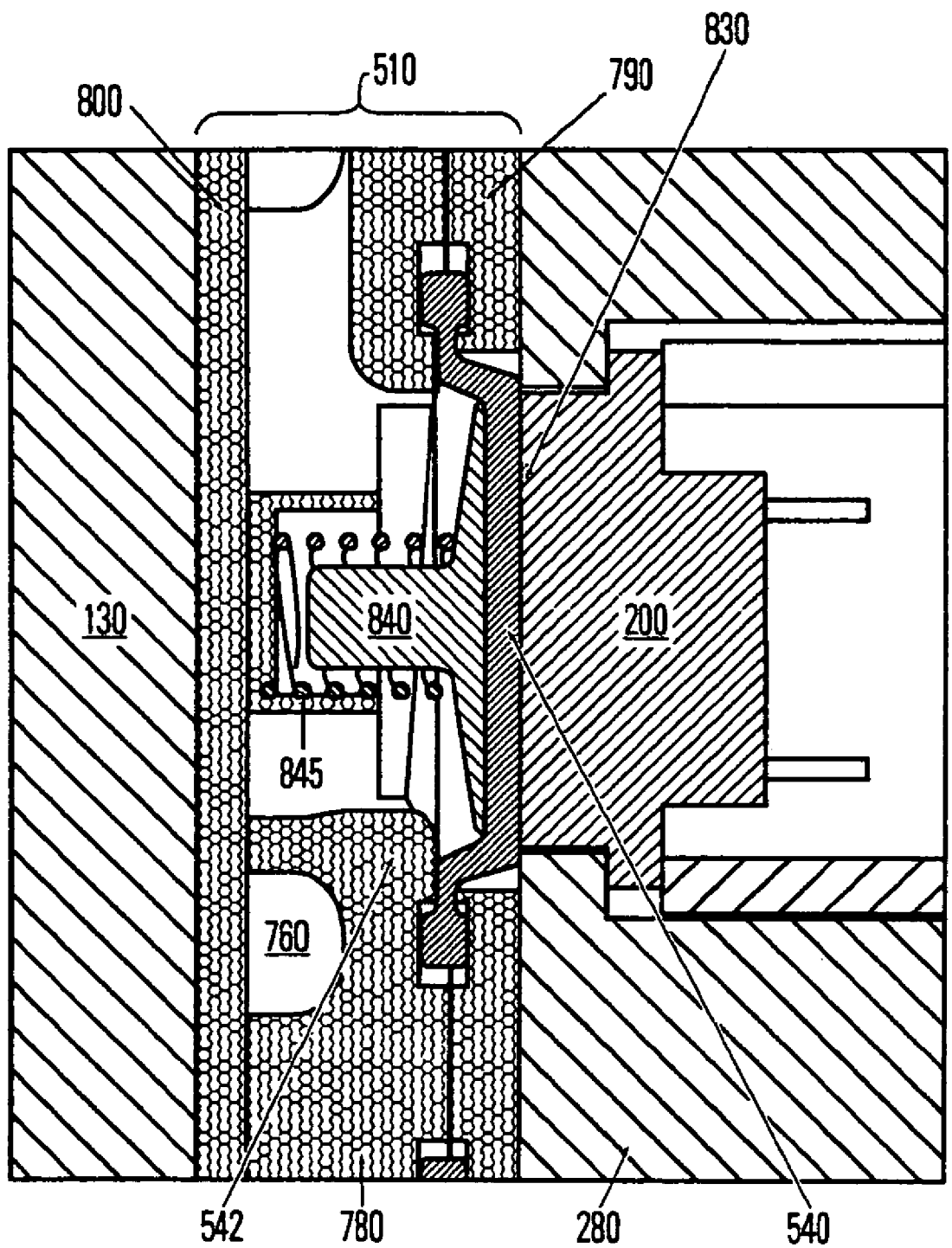
FIG. 6 shows a negative pressure sensing transducer and associated pressure component.
Figure 8:
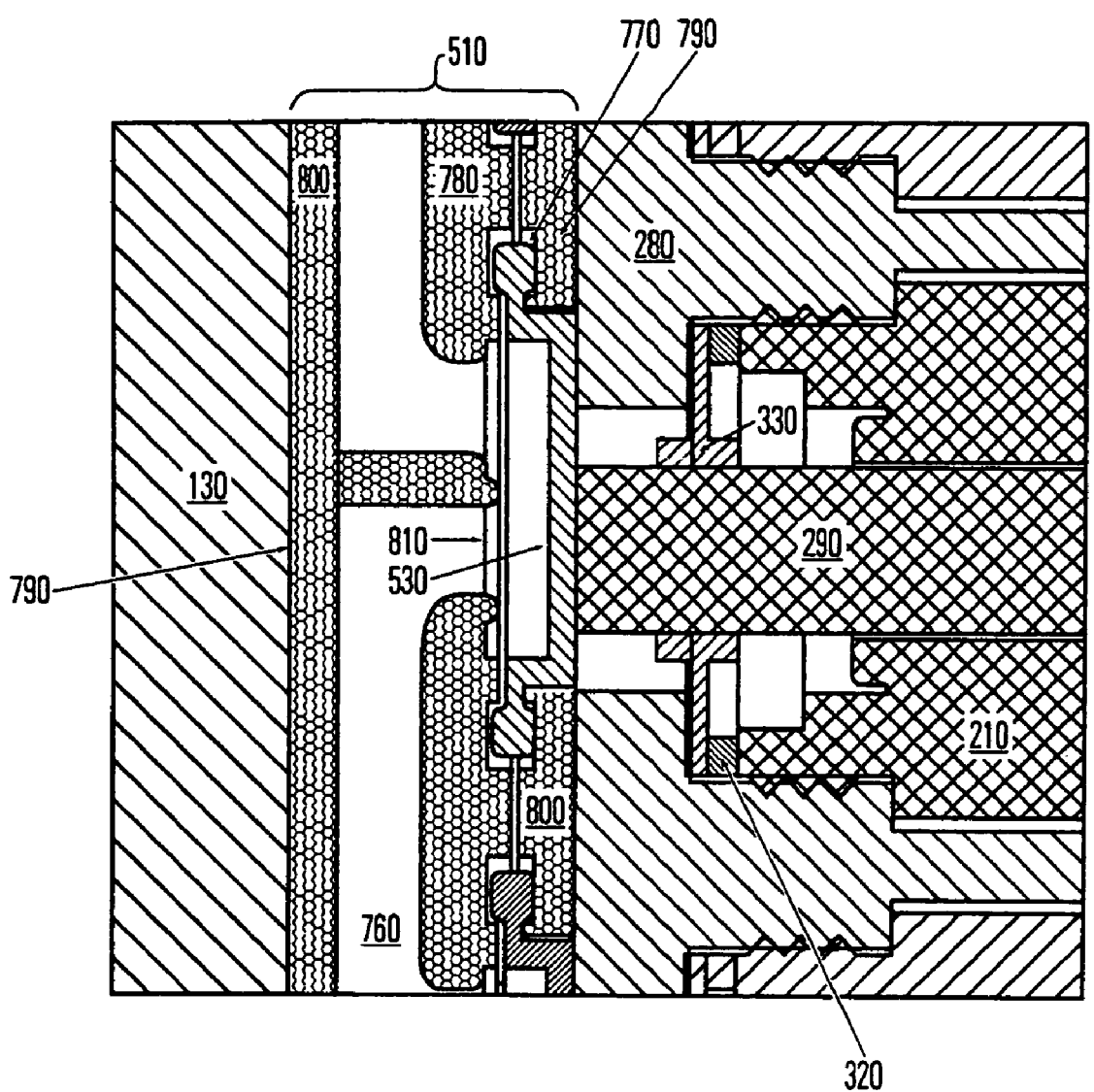
FIG. 8 shows detailed view of the valve actuator and valve component.

Each valve actuator 210, shown in detail in FIG. 8, has a solenoid-operated plunger that moves the valve diaphragm 530 of a disposable valve component 520 to open or occlude a fluid path orifice. The valve actuator 210 shown may be biased closed by a spring (not shown). A low power level would be needed to keep the valve in an open position, as shown in FIG. 6. The spring-loaded feature is a fail-safe advantage, ensuring that no fluid flow can occur with a system or power failure. The motion of the plunger may be independently monitored with a Hall effect or optical sensor (not shown) to provide confirmation of proper valve function and a warning of solenoid failure.

With reference to FIGS. 4, 5, 6 and 7 the pressure transducers 190, both positive and negative 193, 195, 200, may be flat-faced standard devices that couple directly to the pressure diaphragm 540 on pressure measurement components 545 in the cassette. Negative pressure is sensed as shown in FIG. 10, as the diaphragm 540 is deformed. Positive pressure is sensed as shown in FIG. 11, when the diaphragm 540 is not deformed.

The console front panel also includes ultrasonic sensors with interfacing fingers mounted in the door. The operation of these devices is described below in connection with the cassette.

Figure 11:
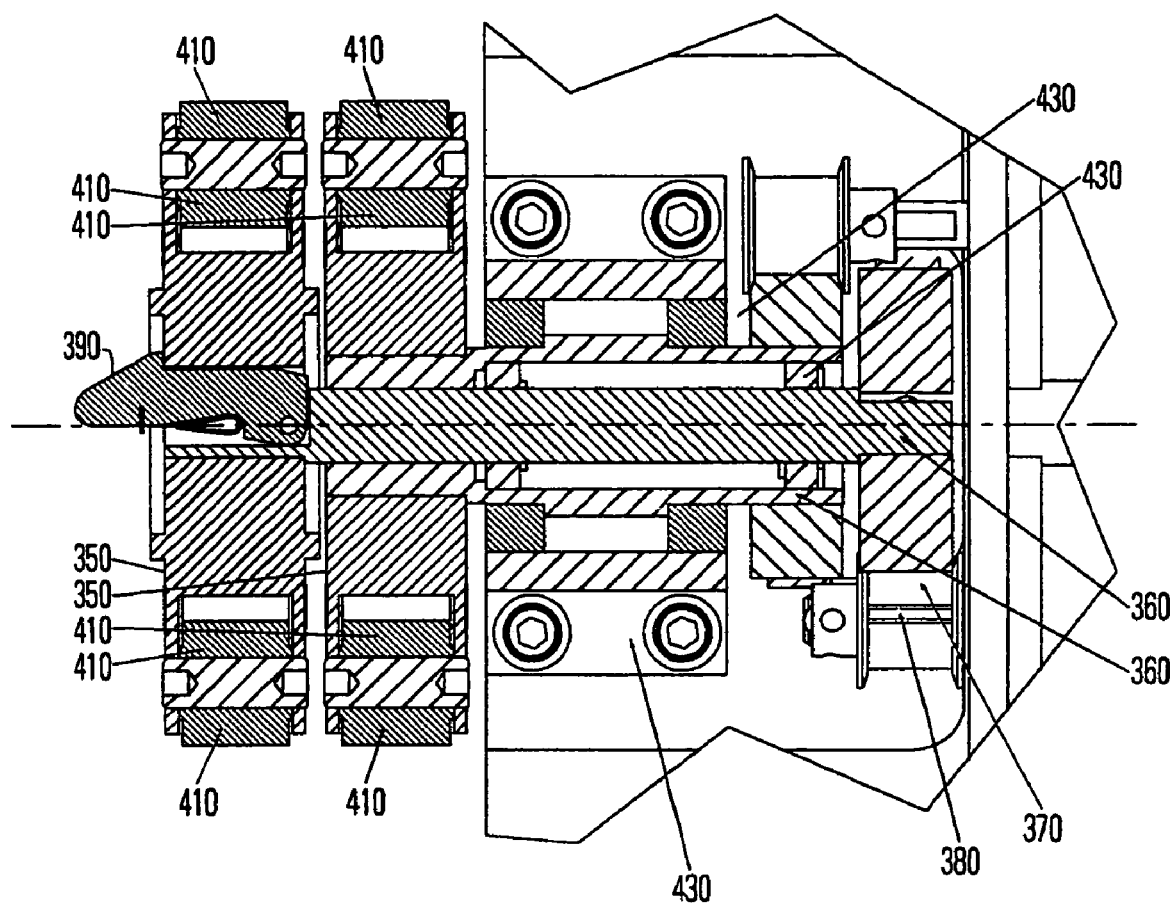
FIG. 11 is a detailed cutaway of the electric motors and rotors.

With reference to FIGS. 9, 10 and 11 the roller pump and drive mechanism 160 includes a number of components. Two roller pump rotors 350 are mounted on a concentric shafts 360 supported by bearings 420 within bearing blocks 430 and driven, through belt drives 370 including sprockets 380, from two motors 390, which may be brushless D.C. motors, on a mounting bracket 440 attached to the door 130. The rotors 350 may be designed to be easily removed from the shafts 360 for cleaning by using a mechanism such as a spring-loaded key 400 that is manually activated. Two such assemblies are mounted in the console door. Four independent tracks 170 are mounted to the console front panel 120. These tracks 170 are spring-loaded 180 against roller pump tubing sections 690 which are located between the tracks 170 and rotors 350 when the cassette is mounted on the console 100.

Each rotor has six to eight rollers 410 equally spaced on its periphery. The small spacing between rollers 410 and the relatively large rotor diameter allow a short track length and short tubing segment on the disposable. This tubing segment is deformed into a short, shallow arc by the rotor and track. As the rotor turns during operation of the system, the rollers 410 force the movement of any liquid, blood, for example, contained in the tubing. Short pump tube segments are desirable in order to minimize overall manifold 510 and cassette size and cost. Additionally, the combination of features allows for a cassette design that automatically places the appropriate pump tube segments in operable connection with the correct pumps and tracks when the cassette is mounted on the front panel and the door is close, thus eliminating the need for an operator to make such connections and the potential for error.

With reference to FIGS. 2, 12, 13 and 23, a centrifuge drive cup 220 is located in the console front panel 120 in order to accept and support a continuous flow centrifuge CFC disk 930 on the disposable, which is further described below. The drive cup 220 may have a shield 450 around it inside the console 100. The drive cup 220 is supported on a centrifuge drive shaft 460 which has bearings 448 spaced at each end with a stationary housing 449 and motor mount 447 supporting these bearings 448. A shield (not shown) may optionally be attached to that portion of the back of the front panel 120 to which the stationary housing 449 is bolted. This achieves a leak-tight assembly preventing fluids from entering the console 100. As one alternative, the drive cup 220 may optionally include locking ears 222 and associated stop pins 223 for locking the centrifuge into the cup 220. As another alternative element in the design, pins 225 may extend from the bottom of the cup to interface with holes 226 in the centrifuge so as to hold the centrifuge 515 in place in the cup and correctly orient the cup and CFC disk 930. As another alternative, a slot 227 on one side of the drive cup accepts a tab 228 on the centrifuge, to further hold the centrifuge in place in the cup during operation and orient the centrifuge. The shaft 460 is driven by a brushless D.C. motor (not shown), preferably with a position encoder, located in the console 100. The motor drive electronics (not shown), mounted in the console 100, may use this encoder to achieve the necessary very smooth, vibration-free, constant-speed rotation of the centrifuge and also allows for the pins 225, slot 227 or other orientation element to be properly positioned when the cup is stopped so as to allow for proper placement of the centrifuge 515 and the CFC disk 930.

With reference to FIG. 28B, to interface with certain centrifuge designs including an umbilical 1670, the cup includes dual gears 1750 to drive the centrifuge disk while the umbilical 1670 is rotated by the cup 1761. In another alternative, concentric cups may be used, the first cup 1761 for rotating the umbilical, and within that cup 1761 a second cup 1762 for rotating the CFC disk 930 at twice the rotational velocity of the first cup 1761. The second cup 1762 includes a slot to allow the umbilical to be properly placed in the first cup. These embodiments are further described in detail below in connection with the umbilical design.

A user interface 250 is located on the outside of the top of the console 100. Preferably, the interface provides sealed push-button or diaphragm switch controls for implementing user control of the specific functions of the processes implemented by the console 100 to a limited and well-defined extent. The user interface 250 includes a display 260, which may be an alphanumeric illuminated monitor, for displaying the state of the process, for display and selection or process parameters, and for warnings or alarm conditions. The interface may include a donor line pressure indicator 270.

A bar code reader 275 may be provided in order to take bar code data such as identifiers, lot numbers and expiration dates from bags, the user, the donor, and other sources. The console 100 provides date, time, and process and blood product information. All process and system data, process parameters, warnings, failures and a process validation may thus be automatically provided to a central blood bank computer.

All processes within the system are controlled by electronic controls (not shown) contained within the console 100 in a conventional manner utilizing a microprocessor-based controller with a watchdog microprocessor, or dual microprocessors, that meet medical device electronic system requirements. Electronic PC boards or similar structures, shown for example, at 340, provide electronic interfaces to various motors, actuators, transducers, and sensors. Although not shown, it will be understood that all operations of components are controlled and/or monitored by the microprocessor or other controller utilizing standard techniques known in the art, in response to inputs from the sensors, such as the pressure transducers, and to set process procedures programmed into software, stored in a ROM or other storage device, which is used to implement the process identified using a bar code 276 or other identifier on the cassette 490 that may be read by the bar code reader 275 or the like mounted in the console. It will be understood that all components will be electronically coupled to such controller via control circuits such as the transducer printed circuit board. Control software to control the microprocessor may be written in C+ and should follow FDA and ISO guidelines for medical device software. As an alternative to a microprocessor and control software instructions, a state machine, which could be implemented using a FPGA, could be used.

Disposable Set

Figure 14:
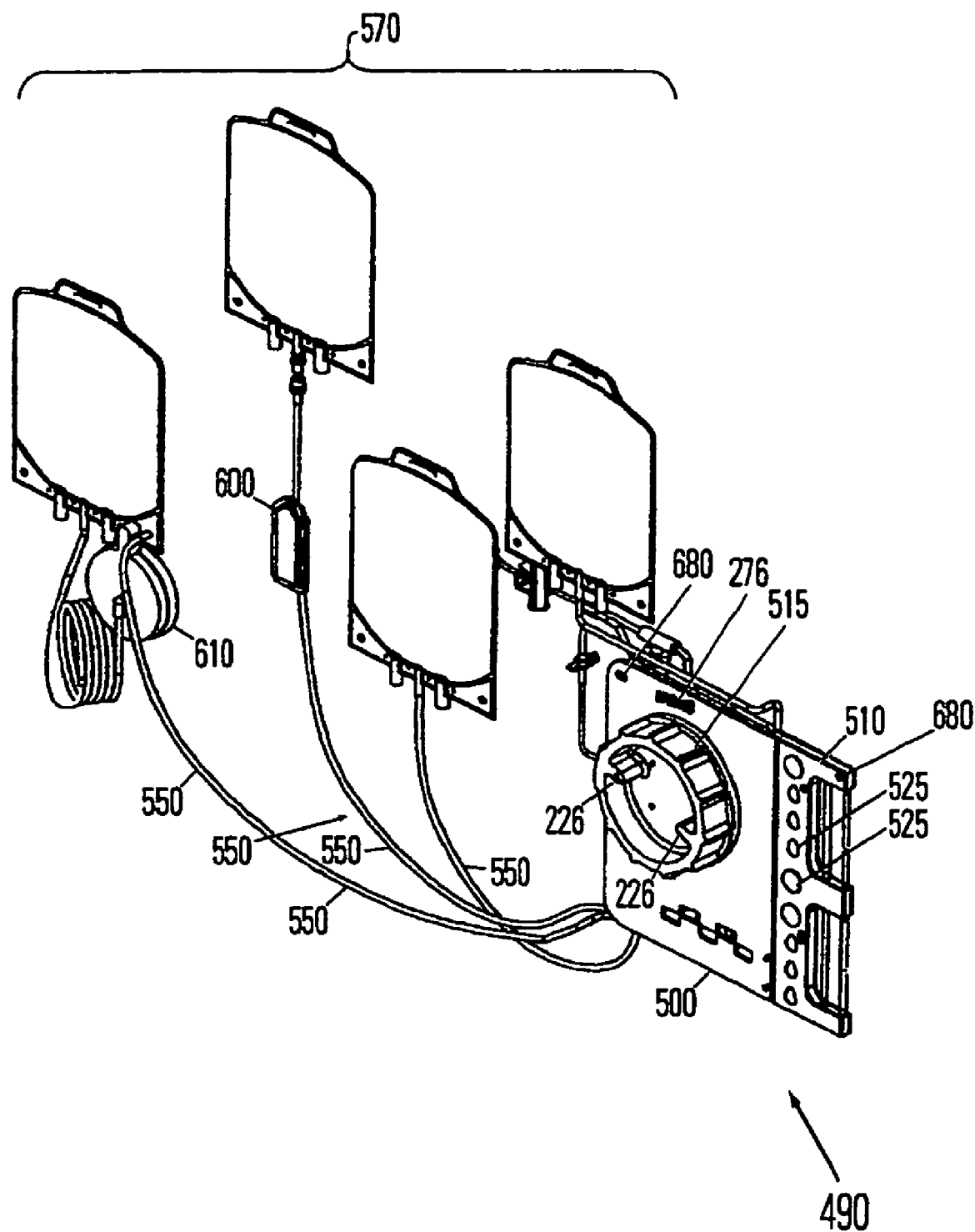
FIG. 14 is a first view of the disposable set.

The disposable sets 480 for processes implemented by the system have several components as well as the overall design approach in common. This overall design is shown in FIGS. 14 and 15 with the structure of the cassette shown conceptually in FIG. 16 and in FIG. 17. The disposable set 480 consists of a cassette 490, including a manifold 510, a continuous-flow centrifuge ("CFC") 515, and a cassette frame 500 that supports the manifold 510 and the CFC 515. The frame may be formed of injection-molded plastic disposable component or similar material with sufficient rigidity to support the manifold 510 and CFC 515, and to allow the valve and sensor components 525 to be precisely located opposite the actuators and sensors mounted on the console front panel 120 and console door 130. The manifold, frame and portions of the CFC are preferably made of clear plastic so as to allow for the use of optical sensors mounted in the console, as further described below. The cassette also has a bar code 276 that may be read by the bar code reader 275 in the console 100. This provides identification to the console 100 of the process to be implemented. It also provides cassette calibration valves to allow for more efficient pump operation, cassette lot number, and expiration date.

The disposable set 480 also includes various components 570 attached that are attached to the manifold 510 by tubing 550. These components 570 may include one or more solution bags 655, such as a red cell storage solution bag 650; anticoagulant bag 740; blood product bags 635, such as a plasma bag 630 and/or red blood cell bag or bags 640; bacterial filters 600; leukofilters 610; and a donor blood collection tube 620 with access needle 660.

Figure 18:
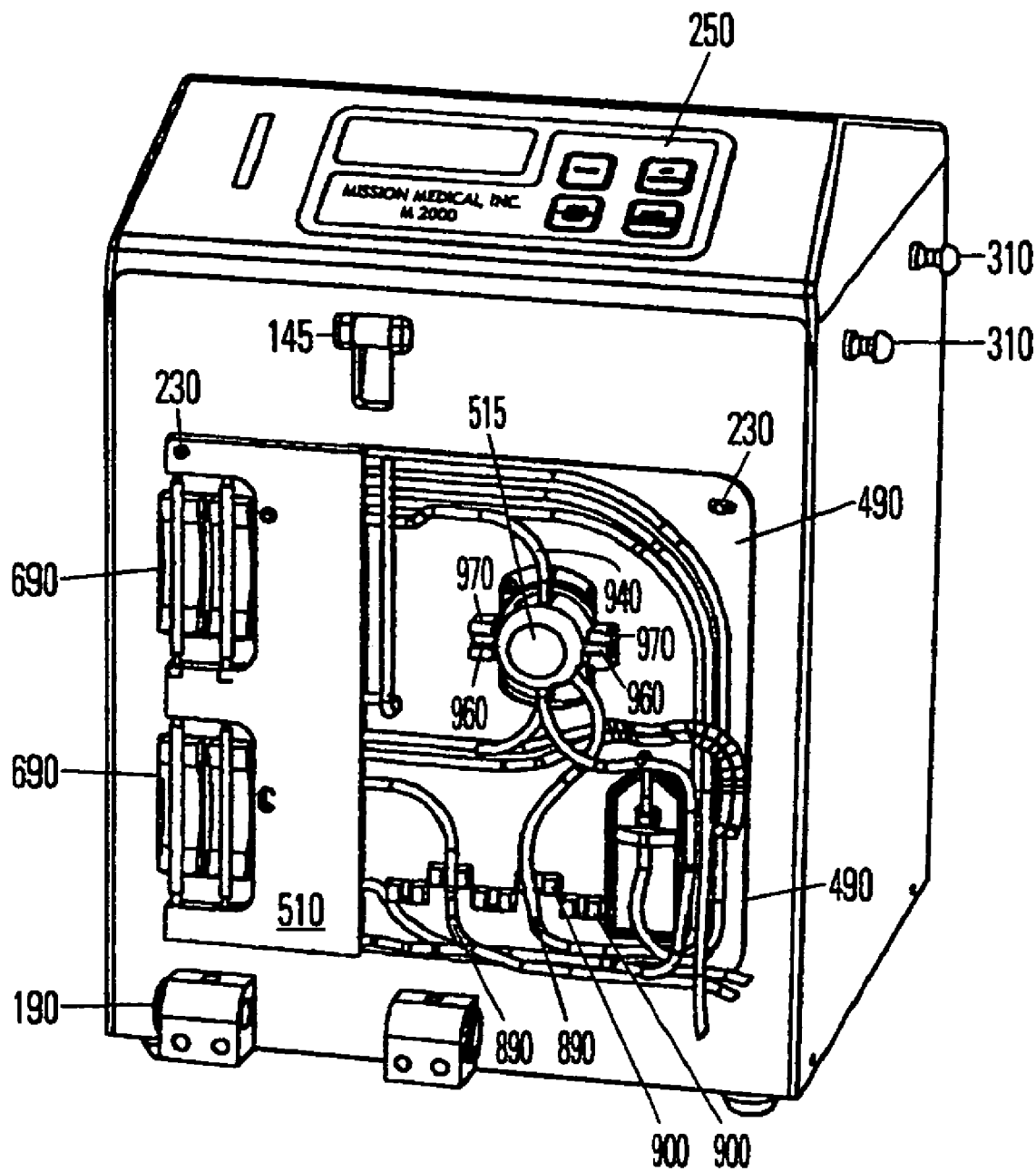
FIG. 18 is a view of the console with a cassette mounted.

The cassette 490 may be mounted on the vertical front panel 120 of the console, as shown in FIG. 18. The cassette 490 is held by the user vertically and is lowered into the space between the open door and the vertical console front panel 120. It is lowered until the support and alignment holes 680 in the top of the cassette 490 as shown in FIG. 18 are opposite the horizontal locating pins 230 on the front panel 120. The holes 680 and pins 230 may be placed strategically to permit only one possible placement of the cassette 490 within the console 100. With reference to FIGS. 35A and B the cassette 490 is then pushed horizontally toward the front panel 120. The CFC 515 will first engage and slip easily into its console drive cup 220 mechanism. In a rotating cup design, pins 225 in the cup, and/or slots if an umbilical design is used, will have been properly oriented using the position locator in the drive motor. Then the locating pins 230 on the console front panel 120 will engage the support and alignment holes 680 in the cassette 490. The process of mounting the cassette 490 takes no appreciable force and is completed when the cassette 490 is mounted on the pins 230 and is contacting the console front panel components. Then the console door is closed and latched, securing the cassette 490 between the door and the console front panel 120. This cassette mounting process takes a few seconds. Then components 570 such as solution bags 655 and blood product bags 635, are hung and/or connected, and the system is ready for donor connection and use.

The cassette 490 is hung vertically on the console front panel 120 to allow easy, direct, close visual observation of mounting of cassette 490 to the console 100. Vertically mounted cassettes are also easier to insert into the console 100 than horizontally mounted cassettes. Vertical mounting also allows for a vertical door design that does not require lifting the entire weight of the door as with a horizontal door and a vertical front panel 120, which is more easily cleaned than a horizontal front panel. Additionally, substantial vertical positioning of the cassette allows gravity to aid in separating air from liquid in the disposable set 480 components 570; air removal, including air removal during the initial priming or filling of the centrifuge (usually including a slow rotation or clocking of the rotor) is easier since the centrifuge can be positioned to allow air to move upward along vertical fluid pathways. Furthermore, as an important safety feature, fluid leaks are seen more easily and quickly when they occur since the fluid is not contained on a horizontal surface but flows downwards along vertical surfaces for collection at the bottom of the cassette 490. Finally, the vertical mounted cassette 490 allows for a substantially horizontal rotor on the centrifuge drive which permits fluids to drain from and not accumulate in the drive and allows air to be more easily removed.

The manifold 510, which may be bonded or ultrasonically-welded to the cassette frame 500, is shown in more detail in FIG. 19 and incorporates several components, including roller pump tubing sections 690 for liquid flow control, fluid flow pathways to the sensor and valve actuation components 546, 520 which are more specifically identified below in the discussion of the various system procedures; valve diaphragm 530 components to turn on or off fluid flow in selected fluid pathways 750; and pressure diaphragm 540 components to measure selected fluid pathway 750 pressures.

The manifold 510 includes molded-in fluid pathways 760 and may include interfaces for valves and sensors. Four roller pump tubes 690, for anticoagulant 710, whole blood 720, red blood cells 700 and storage solution 730, are connected to various fluid pathways 760, and are further described below. The fluid pathways 760 end in tubing receptacles 934–939 and 941–950 for receiving tubing 550 that attaches selected components 570 appropriate for the process the cassette 490 is intended to perform. It will be appreciated by those of ordinary skill in the art that a primary feature of the system is flexibility, in that it may perform different process by utilizing different cassettes and software. For this reason, not all of the fluid pathways and/or roller pump tubes would be used in every process, and, depending on the process, some could be selectively eliminated without affecting the performance of the cassette. Furthermore, the exact position of the various tubing, valves and pressure sensors could be altered, providing the associated elements of the console 100 were modified accordingly, without affecting the basic concepts of the manifold design. For ease of explanation of the structure of the manifold 510, however, the figures include fluid pathways and tubing that would not be used in all processes. Additionally, including all possible fluid pathways and tubing for multiple processes could assist in the manufacturing process by allowing for a consistent basic manifold structure that could be used with more than one process. Ideally, a single manifold structure could be used with all processes.

As shown in FIGS. 5, 6, 7 and 8 the manifold 510 consists of three parts: a mid-body 780 into which channels, including fluid pathways 760 are molded from one side; a back cover 790, adjacent to the console front panel 120 when in operation, that seals the valves, pressure sensors and any other component interfaces; and a front cover 800, adjacent to the console door when in operation, that covers and seals each fluid pathway. The back cover 790 traps the elastomeric valve diaphragms 530 and pressure diaphragms 540, which are part of the valve and sensor components 520, 546, and which may be two-part molded to the front cover 800 at the location shown at 770, between the front cover 800 and the mid-body 780. The elastomeric diaphragms provide the deformable surfaces for valve and pressure sensor interfaces. It may also be appropriate to mold fluid pathways 760 in both sides of the mid-body, allowing for more channels and potentially simplified arrangement of elements on the cassette.

Figure 12A:
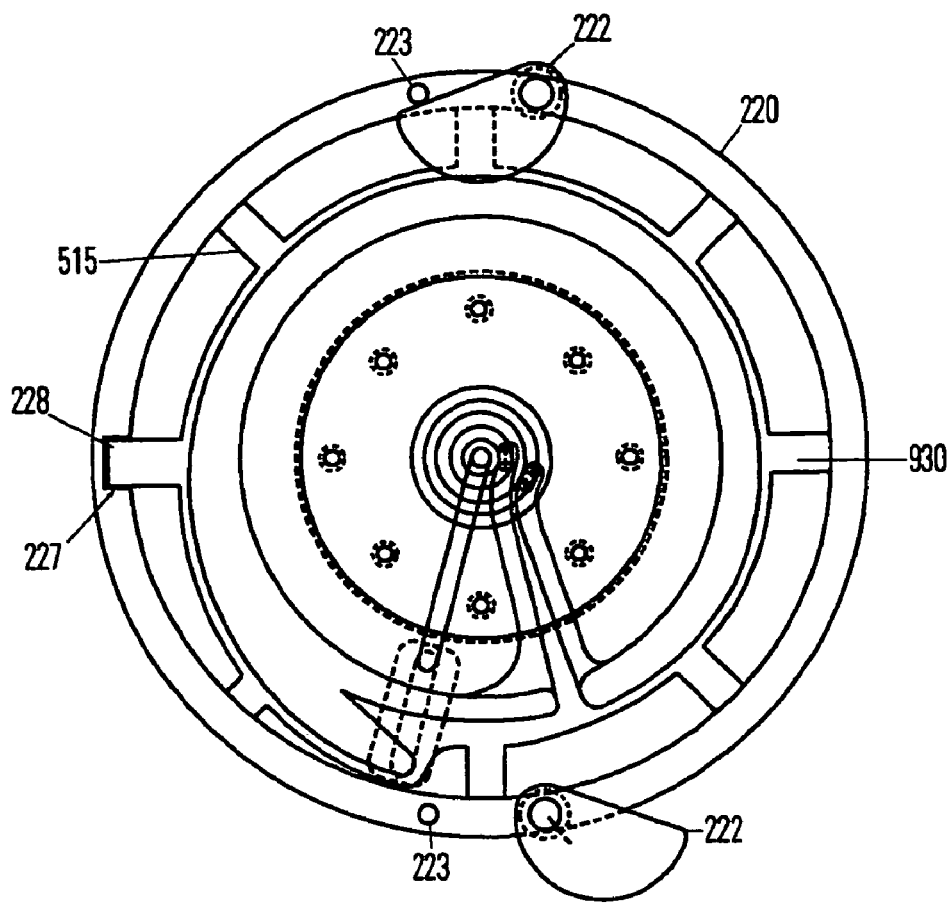
FIGS. 12A and 12B show the drive cup.
Figure 12B:
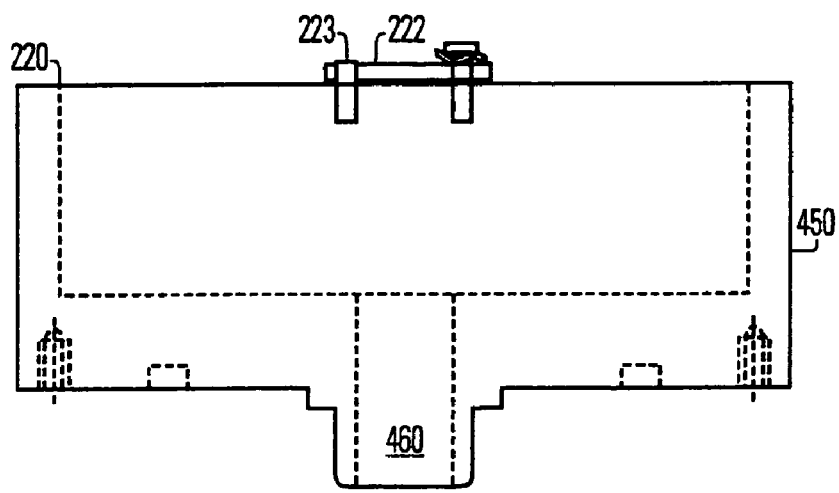
Figure 13:
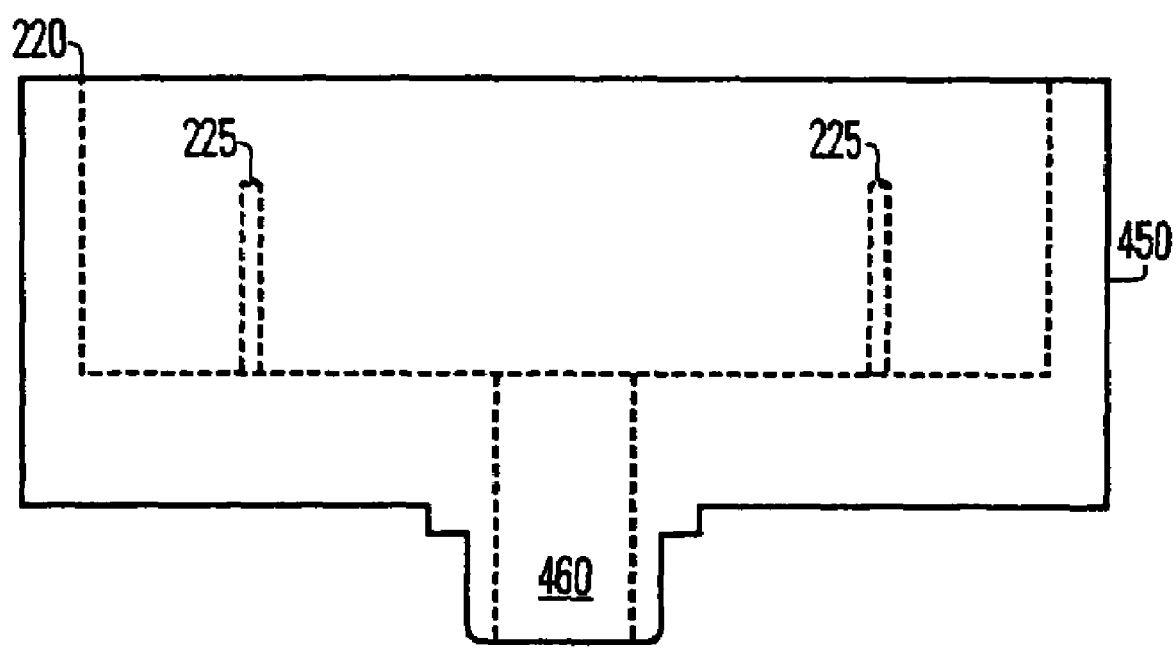
FIG. 13 shows alternative features for the drive cup.

The operation of the valve components 520 will now be described. When the cassette 490 is mounted on the front panel 120, the valve diaphragms 530 are each located opposite the valve actuators 210, shown as solenoids with plungers 290, secured to the front panel 120. The elastomeric valve diaphragm 530 is in a normally open position when not deformed by the plunger 290, and resists deformation by the plunger 290 to close the valve. The valve diaphragm 530 also resists negative pressures and does not close when exposed to such pressures within the fluid path. When the console door is closed, the cassette 490 is moved by the door up against the console front panel 120 and the spring-loaded plunger 290 is thereby forced against the diaphragm 530. The valve diaphragms 530 are deformed by the spring-loaded plungers 290 on the console 100 to contact and occlude a tubular port 810 molded into the mid-body 780 and thereby close a fluid pathway. The tubular port 810 has a raised annulus 820 around it against which the plunger 290 pushes, creating a seal and closing the port and fluid flow path. When the solenoid is energized, the plunger 290 pulls away from the manifold 510, allowing the diaphragm 530 to pull away from the port due to its elastomeric bias, and the fluid path is open. With reference to FIGS. 11 and 12, the pressure diaphragms 540 contact pressure transducer 190 faces to expose the transducer face 830 to the fluid pressure. The front and back covers 790, 800 are ultrasonically welded to the mid-body 780 along each side of each valve, pressure or other components and the fluid pathways 760 to prevent fluid leaks between pathways or to the outside.

Figure 5:
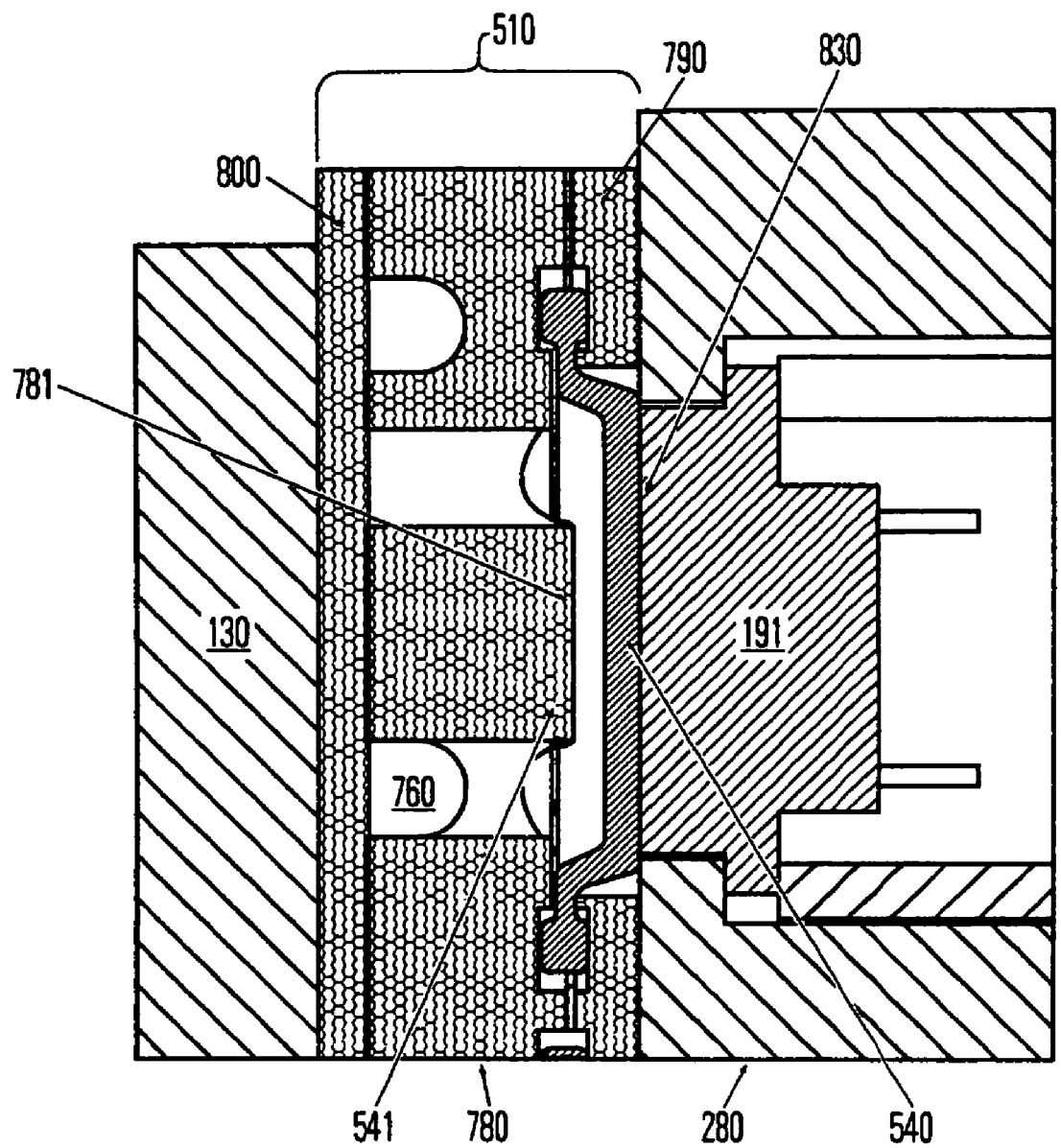
FIG. 5 shows a positive pressure sensing transducer and associated pressure component.

The sensor components 546 will now be described in more detail. The design of the positive pressure components which are integrated and molded into the cassette 490 is shown in FIG. 5. A flexible elastomeric pressure diaphragm 540, of material similar to the valve diaphragm 530, is sealed between the back cover 790 and the mid-body 780 of the manifold 510. Fluid pathways 760 bring fluid into and out of the mid-body 780 space 781 adjacent to the diaphragm 540. When the console door is closed, the outer surface of the pressure diaphragm 540 contacts the face of a pressure transducer 191 which is mounted to the console front panel 120. The fluid in the fluid pathway 760 exerts pressure across the highly flexible diaphragm 540 to the transducer face 830. The transducer output may be reset to zero every time a new cassette 490 is installed and before the process is begun, using ambient air pressure inside the manifold 510.

One possible design of the negative pressure component is shown in FIG. 6. It is very much like the positive pressure interface design except a spring 845 causes the piston 840 to exert a fixed force equivalent, in the example shown, to a pressure of about 250 mm Hg on the diaphragm 540 and on the negative pressure transducer or sensor 200. The function of the spring-loaded piston 840 is to keep the pressure diaphragm 540 in contact with the sensor face 830 during negative fluid pressures and provide a fixed pressure offset. Consequently, in the example shown, when the pressure reading is zeroed at ambient pressure before the process begins, the transducer in reality is seeing the pressure of the spring-loaded piston 840, but reading zero. Thus, a negative fluid pressure can be measured down to the negative of the fixed force equivalent, in this case −250 mm Hg, before the pressure diaphragm 540 pulls away from the transducer face 830. However, no pressure less than the negative value of the equivalent fixed force, or −250 mm Hg in the example shown, can be read.

Figure 7:
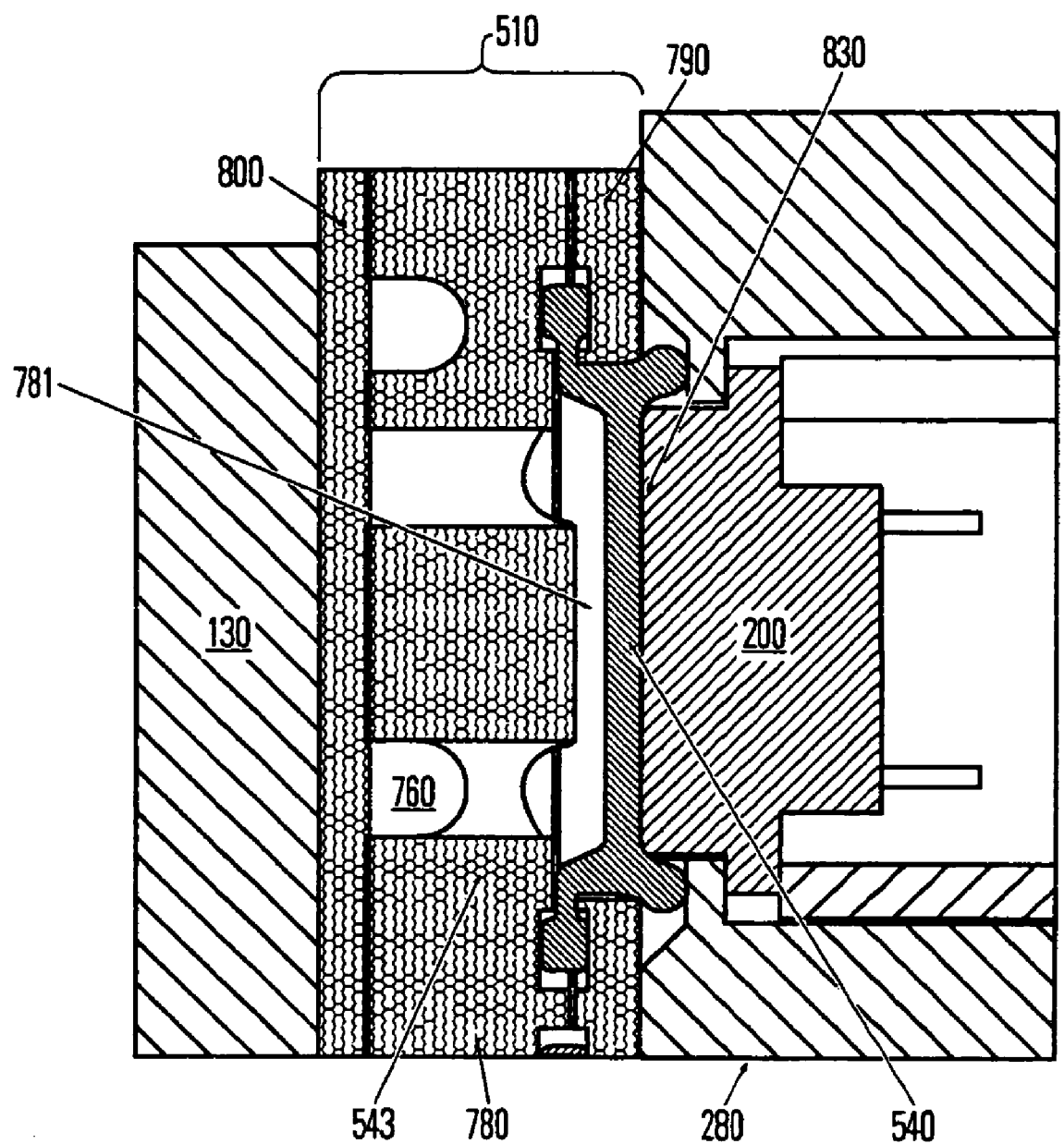
FIG. 7 shows another embodiment for a negative pressure transducer and associated pressure component.

An alternative negative pressure design is shown in FIG. 7. In this design the elastomeric pressure diaphragm 540 has a peripheral seal member 850 that seals the pressure diaphragm 540 to the console front panel 120. Air is trapped in the space 781 between the pressure diaphragm 540 and transducer face 830. This permits positive and negative pressures to be read by the transducer via the trapped air volume. This transducer or sensor is also zeroed by ambient pressure before the process begins.

Figure 19:
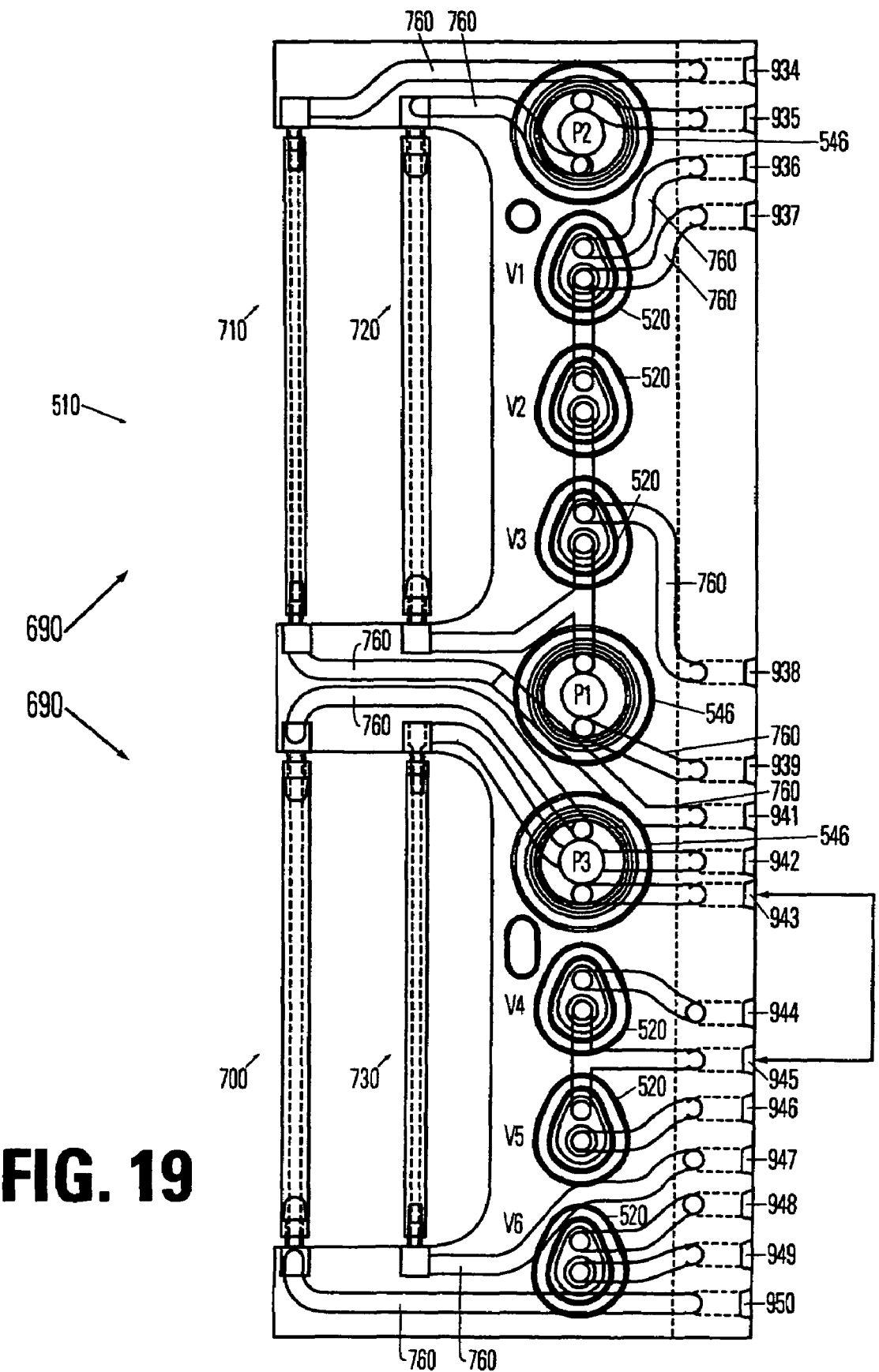
FIG. 19 is a detailed schematic of the manifold portion of the cassette.
Figure 20:
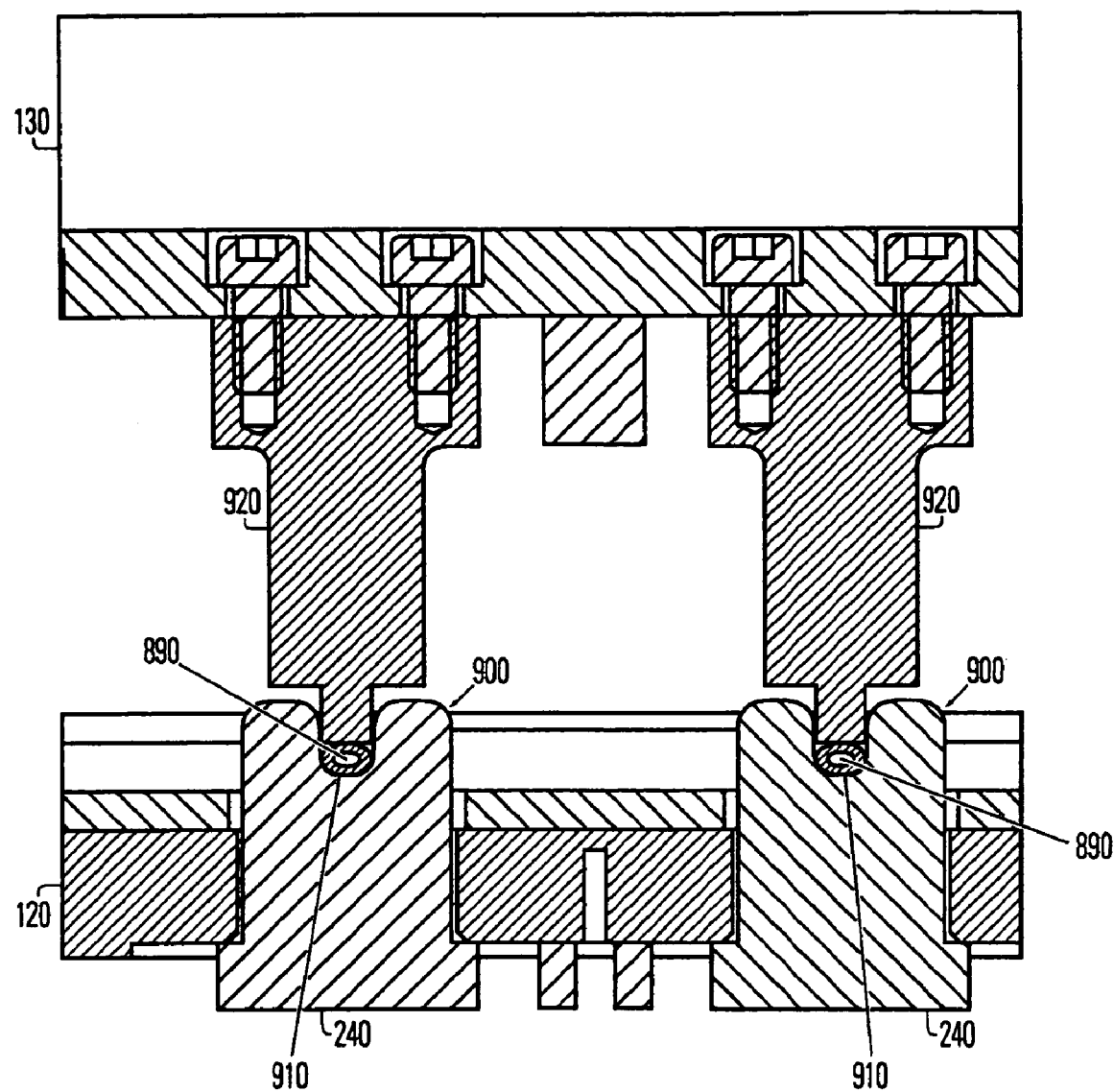
FIG. 20 is a cutaway view of ultrasonic sensors.

With reference to FIG. 19, the four roller pump tubing segments 690 can be constructed of segments of extruded pvc tubing formulated and dimensioned to have properties optimized for use with the roller pump 160. In the embodiment shown these roller pump tube segments 690 are in two sets of two, allowing interface with the roller pump rotors mounted in two sets of two on concentric bearings. This design creates a more compact cassette design. The include a red blood cell tubing segment 700, an anticoagulant tubing segment 710, a whole blood tubing segment 720, and a storage solution tubing segment 730. In each set the tubes are adjacent each other, parallel, and closely spaced. This tubing is slightly stretched onto and bonded to barbed fittings 860 molded to and part of the cassette mid-body 780.

With reference to FIGS. 3 and 10A, the roller pump and drive mechanism 160 with motors are located in the console door. The roller pump tubes are unengaged when the console door is open. When the door is closed and locked in place the roller pump rotors 350 engage the roller pump tubing 690. The rollers 410 on each rotor compress and occlude the tubing against a curved block or track that is mounted to the console front panel 120. No action on the part of the user is needed except to close the door. This eliminates the manual step of inserting tubing into each pump assembly required by many blood processing systems and eliminates the possibility of operator error.

The track may be spring-loaded 180 against the rollers 410 to ensure adequate occlusion but avoid excessive force. The track 170 is pivoted on a track pivot pin 175 parallel to the console front panel 120 at some distance from the center of the track 170. The track is provided with a stop 177 that limits its motion in the direction of the spring force, which is biased towards the rotors 350. The control of spring force and tubing compression by pump rollers 410 to the lowest level necessary to ensure occlusion minimizes hemolysis in this pump design. The roller pump tube segment inside diameter is selected for the flow rates of fluid desired, the degree of "pulsatility" of the fluid that can be allowed, and the speed range capability of the pump rotors 350. This inside diameter is controlled precisely, with tolerances preferably of less than plus or minus 3 mils, in order to achieve accurate flow control in operation as the rotors 350 force the rollers 410 over the roller tubing segments to pump the various liquids through the system.

The manifold 510 also supports tubing 550 that is routed from the manifold 510 to bags and/or other components 570. The tubing 550 acts as the path for fluids moving to and from these components 570. This tubing 550 is bonded to or captured onto the frame at the tubing receptacles as shown in FIG. 19. With reference to FIGS. 14, 15, and 16, the components 570 vary for each process, but can include such items as a leukofilter 610 for red cells; bacterial filters 600 for anticoagulant, red cell additive, or other solution bags attached to the set by the use of spikes 870 or by Luer connectors 880; possible air or bubble traps (not shown); tubing 550 to donor with venous access needle 660 with cap and sample site 670, which may be mixed with anticoagulant introduced via a tube downstream of the sample site; bags for blood products 590, including, for example, red blood cell bags, buffy coat bags and plasma bags; and other various fittings, elbows, Y-connectors, and manual clamps as appropriate. Some of these components 570 may be attached to the cassette frame 500. Preferably, all tubing 550 is bonded into selected tubing receptacles 934–939 and 941–950 on one side of the manifold 510, as shown in the embodiment, to simplify and shorten tubing runs to components 570 or bags. The specific components 570 for various processes are indicated in the process descriptions and schematics described in more detail below.

With reference to FIGS. 16, 17, 18 and 20, portions of the tubing 890 from the components 570 is bonded or captured to the frame on each side of access holes 900 in the cassette frame 500 and engages ultrasonic sensors 240 mounted in the console front panel 120. The tubing 550 can be standard pvc tubing used for fluid flow from the cassette 490 to various external components 570, bags, and the donor. The access hole in the cassette frame 500 bridged by the tubing 550 permits the yoke-shaped sensor to surround the tubing segment on three sides. When the cassette 490 is hung on the front panel 120, the air detection tubing is adjacent to and partially within the slot 910 in the sensor. When the door 130 is closed, a finger 920 on the door pushes the tubing into the slot 910 and compresses it to ensure good contact with the parallel sides of the slot 910 achieving good acoustic coupling. An ultrasonic transducer sends ultrasonic waves through the tube across these parallel sides to a receiving transducer on the opposite side of the slot 910. The differences in acoustic properties between liquids, air, and air bubbles in liquids, are determined by the ultrasonic sensor and its electronics. This is used for safety to prevent air entering the donor in the event of a system malfunction, for ensuring the process is occurring without air bubbles, and for detecting empty liquid-containing bags.

Figure 17:
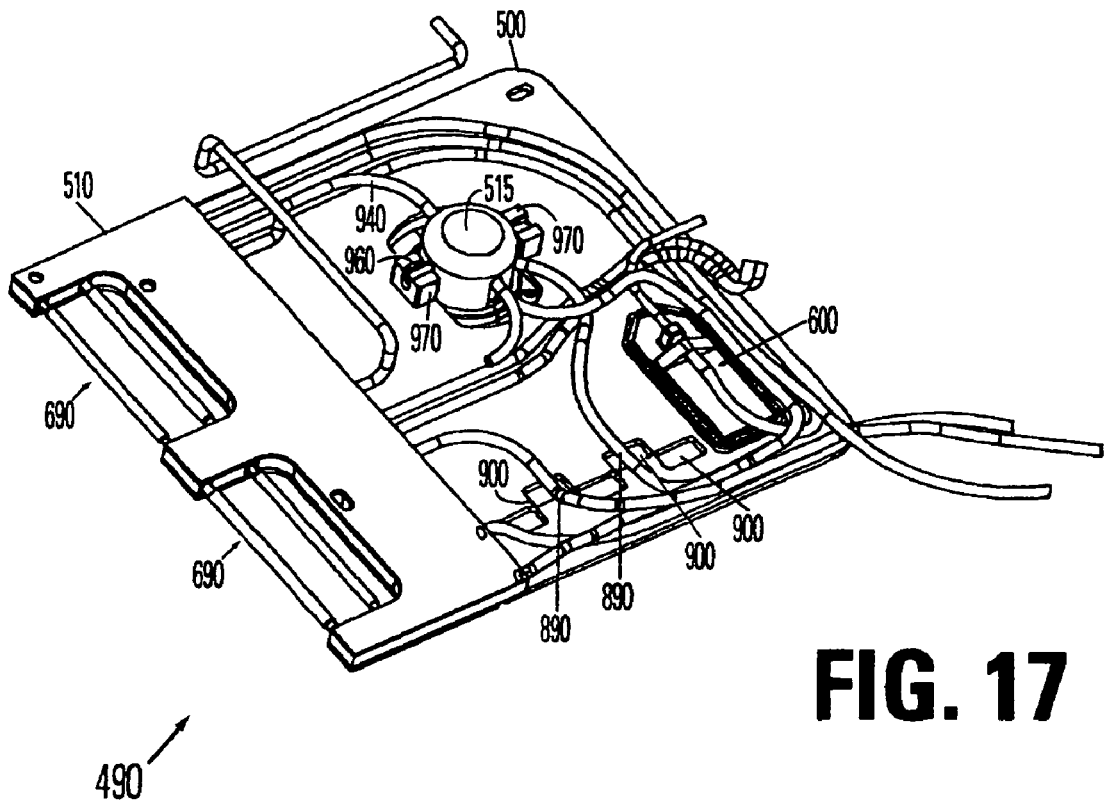
FIG. 17 is a detailed view of the cassette.

With reference to FIGS. 17 and 18, the CFC 515, including the CFC disk 930, is also connected to the manifold 510 by tubing 940. The cassette frame 500 supports the CFC disk 930 loosely and allows direct, easy insertion of the centrifuge into the centrifuge drive cup 220 simultaneous with hanging the cassette 490 on the console front panel 120, without complicating cassette mounting. Details of the CFC 515 are further described below.

Continuous Flow Centrifuge

The CFC 515 is "flexibly" supported on the cassette frame 500 such that it is easily inserted into a centrifuge drive cup 220, 1762 during cassette installation. This "flexible" support structure is decoupled from the disk 930 when the door is closed, permitting the CFC disk 930 to rotate freely. The attachment of the CFC disk 930 to the cassette frame 500 is shown in FIGS. 17 and 18. The CFC disk 930 is attached to the cassette 490 in such a way that it can readily move approximately ±0.040 inch in any direction parallel to the front panel 120 and approximately 0.1 inch toward the front panel 120. Two pins 960 at 180° on the disk static seal housing 1430 fit loosely in two yokes 970 that are part of the cassette frame 500. In the embodiments shown, the centrifuge disk 930 is approximately 6 inches in outside diameter and 1.75 inches thick, although other dimensions are possible.

Figure 24:
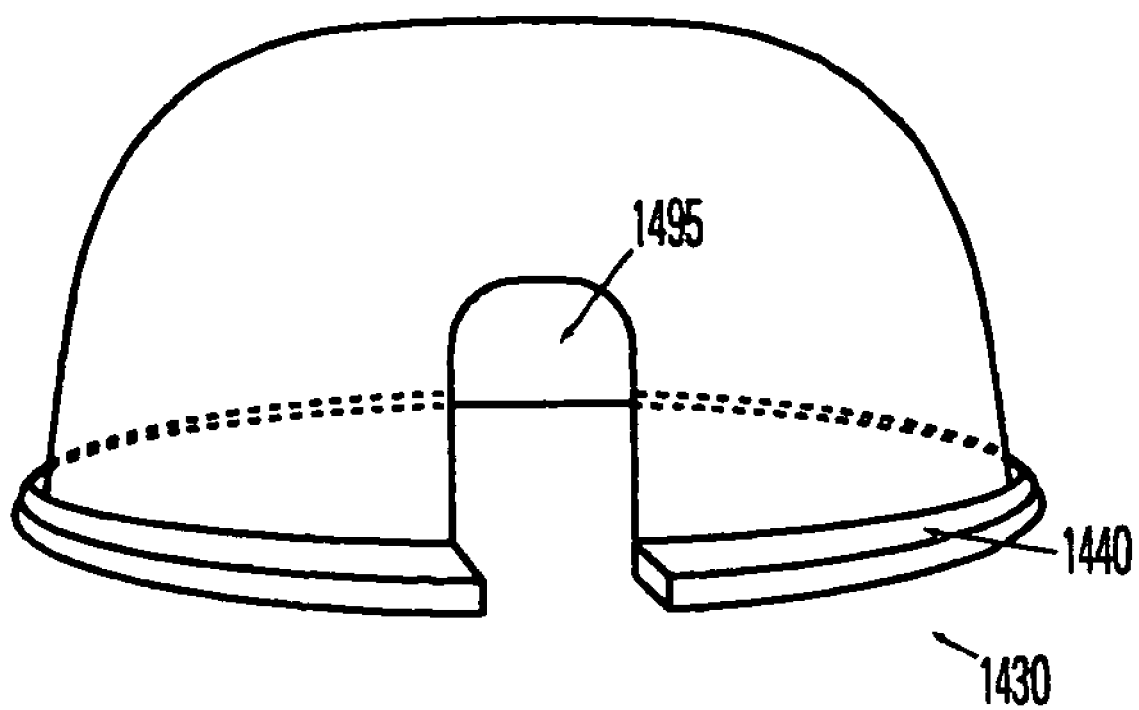
FIG. 24 shows a detail of the housing for the centrifuge.

Two possible approaches to the design of the CFC 515 are described below. In the first approach with reference to FIGS. 21A–B, 22, 23 and 24, the centrifuge apparatus includes several elements that are able to rotate around a central spin axis 1460. These elements include a housing mounting ring 1450, a rotating face seal, a disk cap 1500 and a disk body 1150. The rotating face seal 1480 is supported adjacent to the disk cap 1500, which is mounted on a housing mounting ring 1450 that is rotably connected to rotate around the opening of a bucket-like stationary housing 1430. Contained within the housing 1430, adjacent to the rotating face seal 1480 is a stationary face seal 1490 which is bonded to a distributor 1530. The stationary face seal 1490 is slidably mounted in the 1430, and is also attached to a spring or other spring-loading element 1410 mounted at the top of the 1430. With reference to FIG. 24 the housing forms slot or slots 1495 that allow tubing to be connected to the distributor 1530, while permitting movement of the 1430 as described below.

The CFC disk 930 is supported on the cassette 490 but must be free to rotate after the cassette 490 is in place, mounted to the console body 110 front panel 120, with the console door closed. The console door closure is used to disengage the CFC disk 930 from the cassette 490 such that the disk 930 can rotate freely and is positioned and supported correctly and safely within the centrifuge drive cup 220.

To accomplish this, the housing 1430 includes an engagement lip around the opening. The spring-loading element 1410 in the housing 1430 forces the engagement lip 1440 against the housing mounting ring 1450. The centrifuge assembly of FIG. 24A shows the engagement lip on the static seal housing 1430 contacting a disk housing mounting ring 1450, preventing disk rotation. The door of the console in this embodiment must include a plunger 295 or similar structure, as shown in FIG. 24B, that will, when the door 130 is closed, engage the housing 1430, compressing this housing against the spring-loading element 1410, and moving the 1430 a fixed distance. This separates the engagement lip 1440 from the mounting ring 1450, permitting rotation of the elements mounted, directly or indirectly, on the housing mounting ring 1450. In practice, it may be preferable to include additional elements to improve performance of the device. For example, with reference to FIG. 22, guide 1505 may be mounted on the rotating disk cap 1500, to maintain the rotating and stationary face seals 1480, 1490 in alignment as the spring-loading element 1410 is compressed against the housing. The guide 1505 may also act as a shield to prevent spattering of liquid in the event the seal is compromised.

Figure 22:
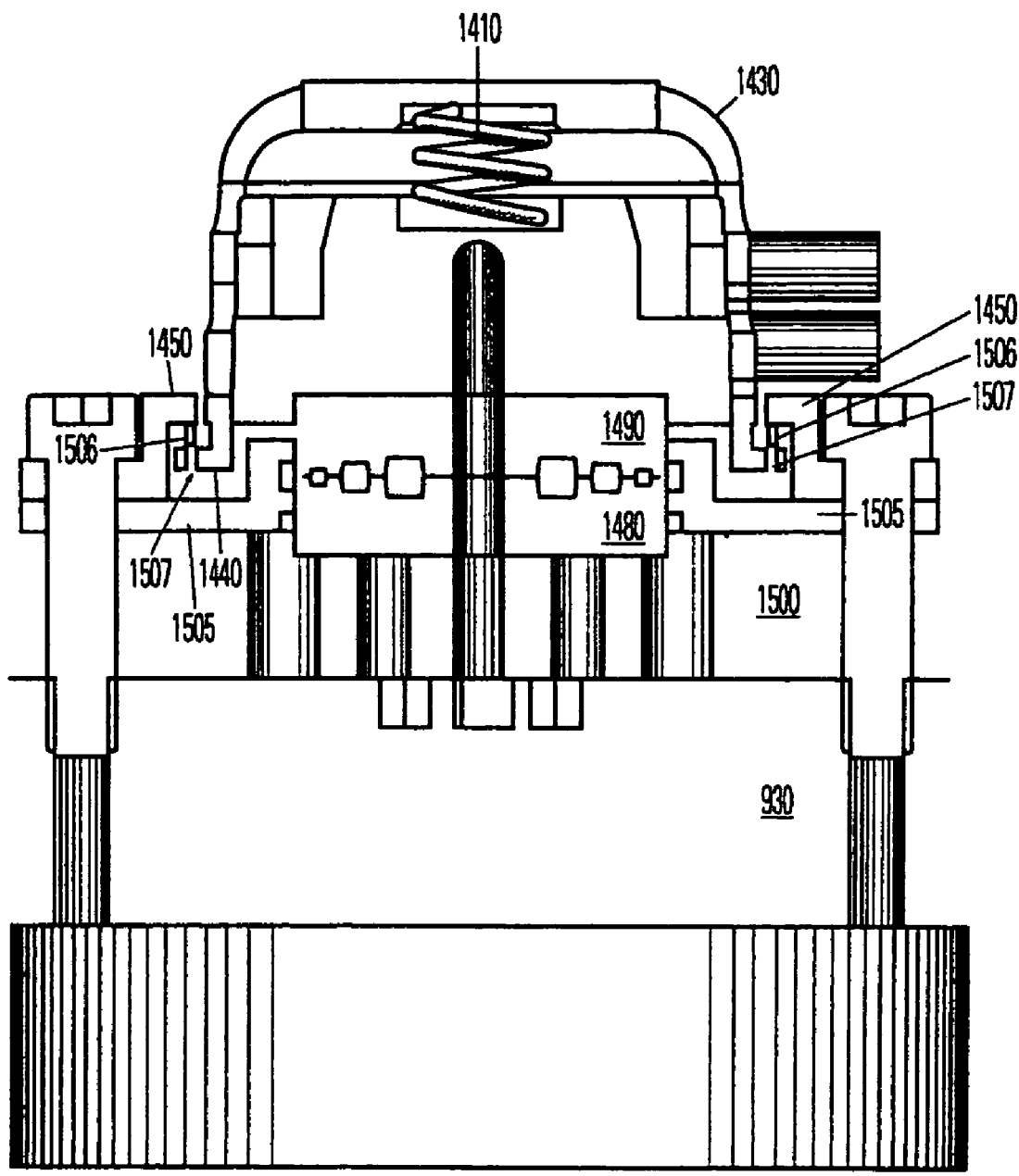
FIG. 22 shows a detailed design of the continuous flow centrifuge that uses a face seal.

The CFC disk 930 is preferably keyed in angular location to the cassette 490 when the centrifuge is not mounted in the console. This may be accomplished using a tongue in groove that is disengaged when the rotor is pushed toward the front panel 120 by the door, or alternatively, as shown in FIG. 22 using pins 1506 on the housing mounting ring 1450, and holes 1507 in the lip 1440 of the housing 1430. This alignment of the centrifuge disk allows appropriate positioning of the CFC disk 930 relative to the console and permits precise control of disk location during priming and other elements of the processes performed by the system as further described below.

Other variations are possible. For example, a stationary sleeve could be attached to a flexing annular part that attaches to the stationary face seal or the distributor 1530. The stationary sleeve could have an annular lip extending radially inward that engages an annular lip on a sleeve that rotates with and is attached to the rotor. The flexing annular part provides sufficient elastic force to make the gap zero between these engaged lips and provides a force that keeps the seal faces firmly pressed together. A projection on the sleeve engages a slot or hole on the stationary sleeve to maintain angular orientation between the rotor, stationary seal, and the cassette. The stationary seal and its distributor are attached to the cassette by a cassette structure that provides angular alignment of the stationary seal.

Figure 25:
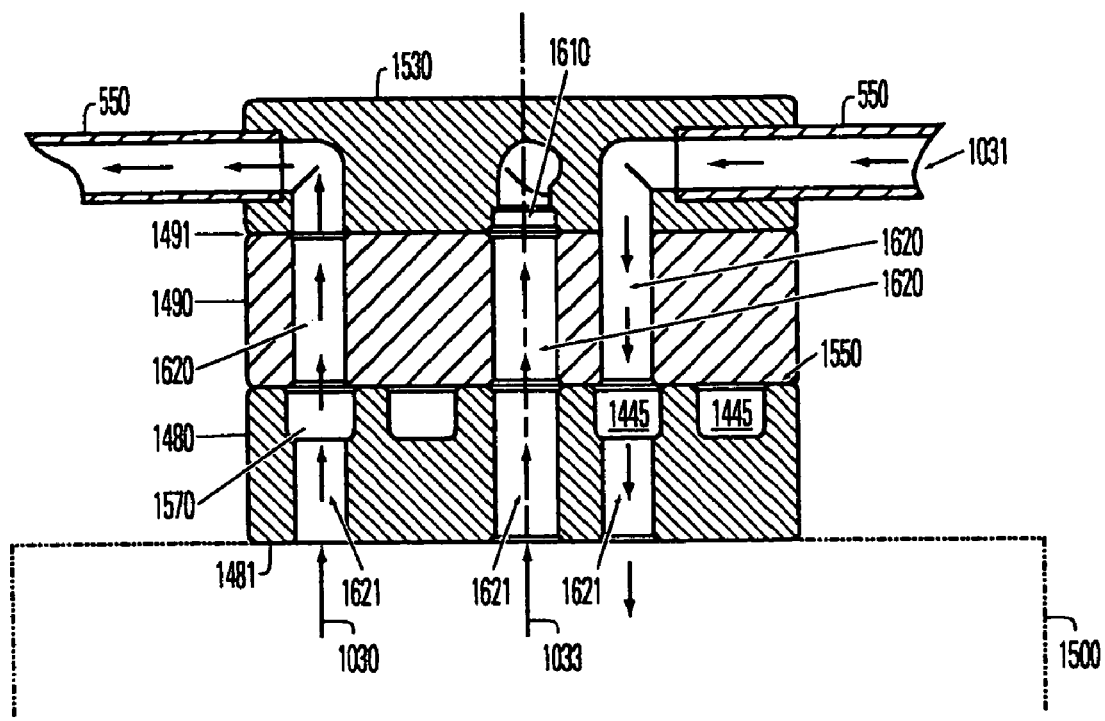
FIG. 25 shows the face seal with three fluid paths.

With reference to FIG. 25, the face seal structure will be described in more detail. The face seal is used for the sealing of fluid paths or ducts that which act as the means for transporting whole blood from the cassette 490 into the rotating CFC disk 930, and transporting plasma and concentrated red cells from the rotating disk 930 to the stationary cassette 490.

The face seal assembly comprises a rotating ceramic (aluminum oxide) face seal and a stationary face seal 1490. The stationary face seal 1490 may be made of carbon (carbon-graphite) or of ceramic. Although carbon has better lubricating capacities and is preferred for that reason, the use of this material may produce an unacceptable amount of particulates. Further, ceramic wears better and may more easily be manufactured to the appropriate "flatness". As noted above, the spring-loading element 1410 provides sufficient force at all times that keep the rotating and stationary seal faces 1480, 1490 in contact with each other. The face seal components each have a central hole 1610 and two or three annular channels 1445 with access holes 1620, 1621 to provide three or fluid paths. The rotating face seal 1480 is adhesive-bonded 1481 to the molded plastic centrifuge disk cap 1500. The disk cap 1500 provides fluid channel access to the ceramic fluid path holes. The annular channels 1445 in the rotating face seal 1480 collect flow from localized holes 1620 in the stationary face seal 1490. The mating surfaces of the face seals are made extremely flat, to less than 3 helium wavelengths. This ensures sealing of all of the flat lands between the grooves. The outer face seal land 1550 provides sealing to plasma 1030 which flows through the outermost annular channel 1570. This is the only seal to the outside or to ambient air and is the only face seal that could allow bacterial contamination of the blood from ambient air. Therefore, this outer face seal must not leak. The plasma 1030 in this outer channel is kept at a slight positive pressure, and is dependent only on the plasma bag height. Plasma is generally not pumped through the seal, so that plasma pressures cannot be negative or significantly positive which might cause the seal to be compromised. The whole blood 1031 inlet pressure is measured with a sensor (not shown) in the cassette 490. This pressure is limited to a maximum of 5 psig to avoid opening the seal. These are operating characteristics accepted by the FDA to ensure sterile operation and be considered as functionally closed and sterile. However, the internal face seals can leak slightly without compromising blood component quality or sterility.

A plastic molded distributor 1530 is adhesive-bonded 1491 to the stationary face seal part 1490. Flexible tubes 550 attach to the fluid ducts of this distributor 1530 and connect to the manifold 510 thus connecting stationary face seal 1490 and its fluid pathways 750 to the stationary disposable components 570 that are part of the disposable cassette 490.

This face seal assembly is made from materials used in similar blood applications and with similar dimensions and compressive forces. This is done to ensure proper function and also to more easily obtain FDA approvals, but other designs and modifications may be possible.

Figure 26:
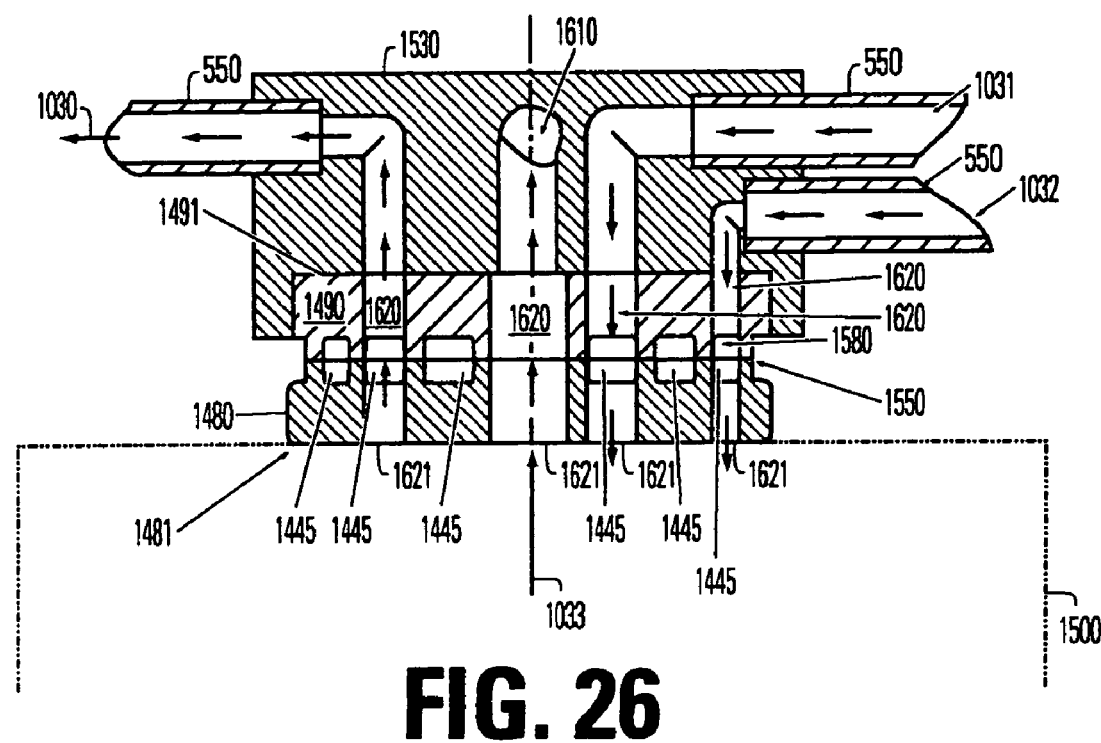
FIG. 26 shows the face seal with four fluid paths.

An alternative face seal design is shown in FIG. 26. This is very much like the design in the embodiment of FIG. 25, except that it has four fluid pathways rather than three. The additional outer annular channel 1580 provides a fluid path for red cell storage solution 1032. This solution is pumped into the CFC disk 930 through this face seal and into the concentrated red cells after they are picked up via a red cell port at a maximum radius in the separation channel 990 in a manner further described below. The storage solution flow 1032 in its annular channel within the seal also cools seal surfaces and provides some lubrication to the sealing faces or lands. The storage solution pressure is maintained near ambient to prevent air leaks into the storage solution from the non-sterile ambient air (if the storage solution pressure were very negative); and to prevent solution leaks out into the ambient environment (if the solution pressure were very positive). Such leaks out of the seal (if only of storage solution) would not be a biohazard, or any hazard, to the user. Preferably, concentrated or "packed" red blood cells 1033 are removed through the path defined by the central holes 1610 in the disk, particularly if the red blood cells have a high hemocrit, that has not been reduced through the addition of storage solution or the like, so as to reduce the possibility of damage caused by shear forces in the annular channels 1445 during operation of the centrifuge.

Figure 27:
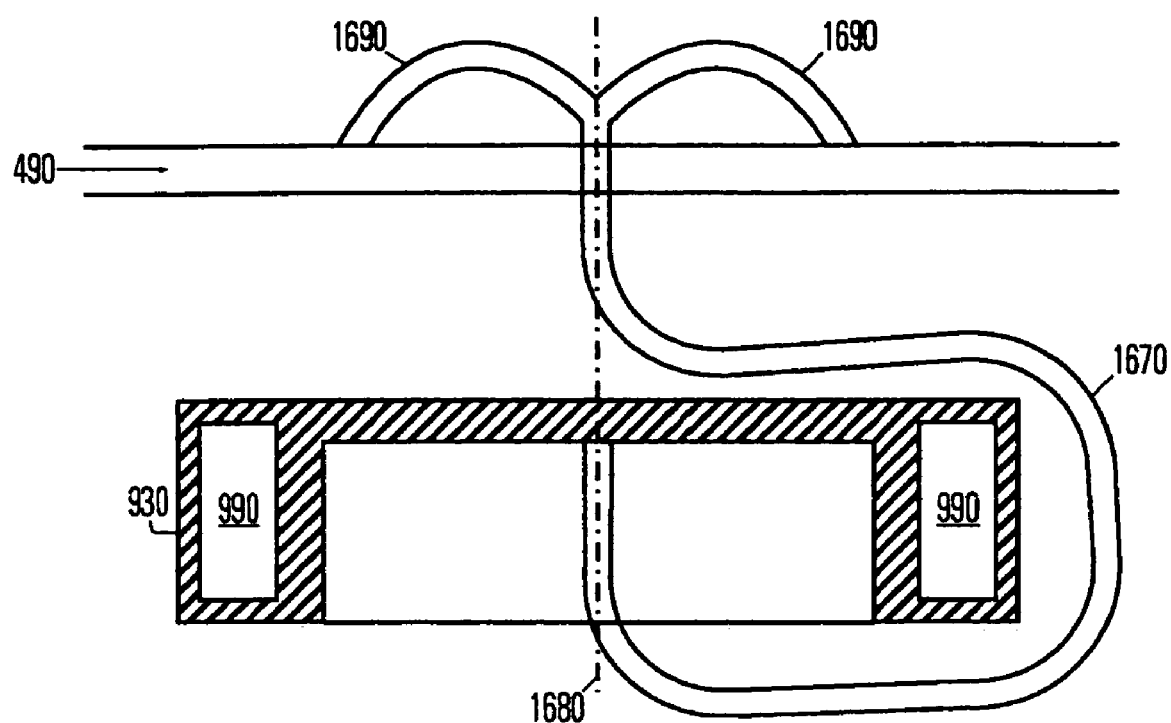
FIG. 27 is a conceptual representation of the umbilical or skiprope design for the continuous flow centrifuge.
Figure 29:
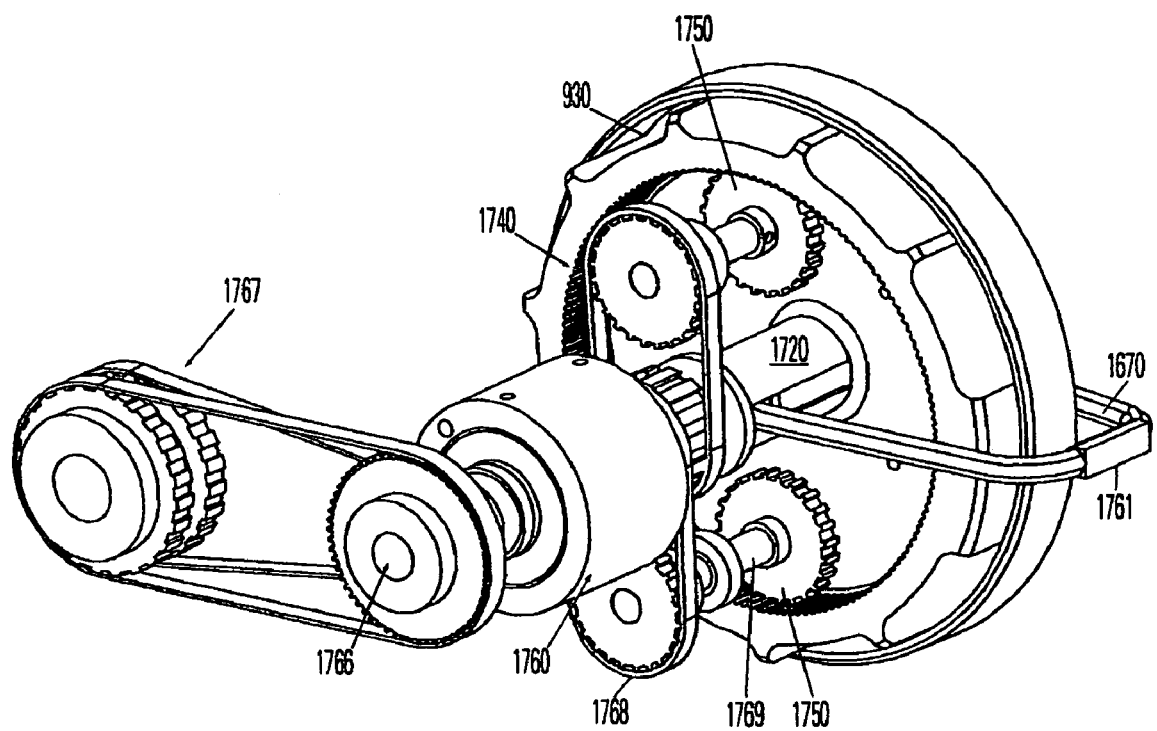
FIG. 29 is a view of the drive mechanisms for an umbilical continuous flow centrifuge.
Figure 30A:
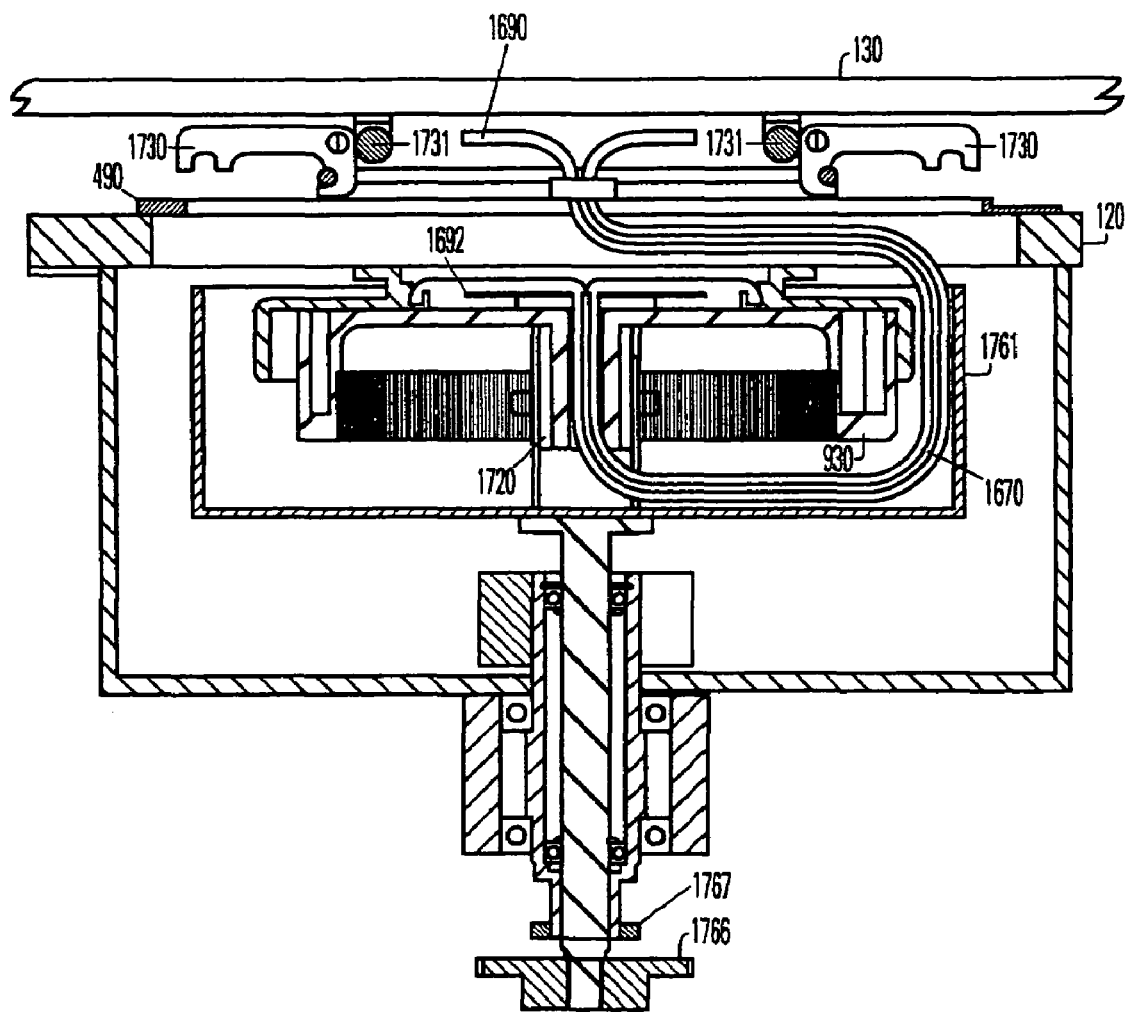
FIGS. 30A and 30B are cutaway views of a umbilical continuous flow centrifuge.
Figure 30B:
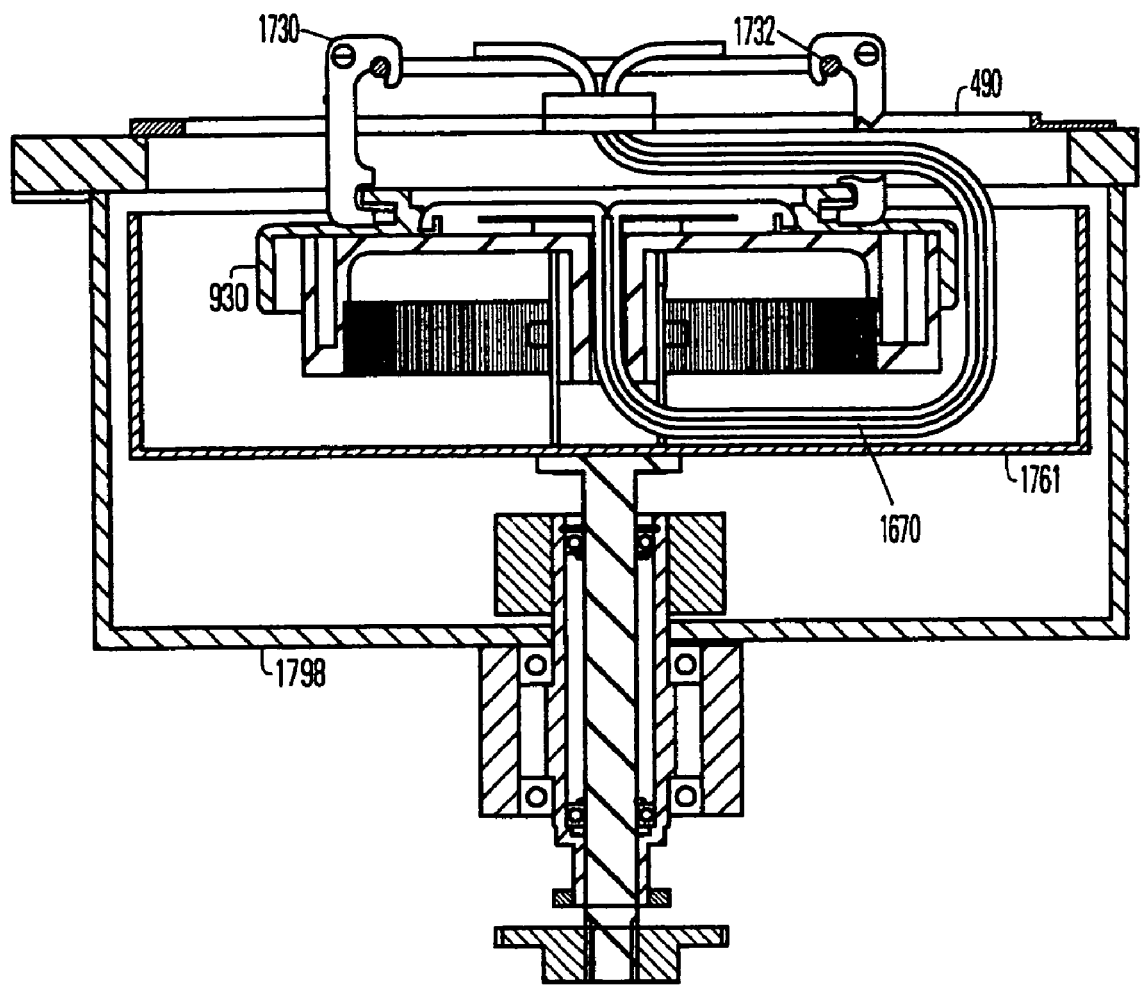
Figure 31:
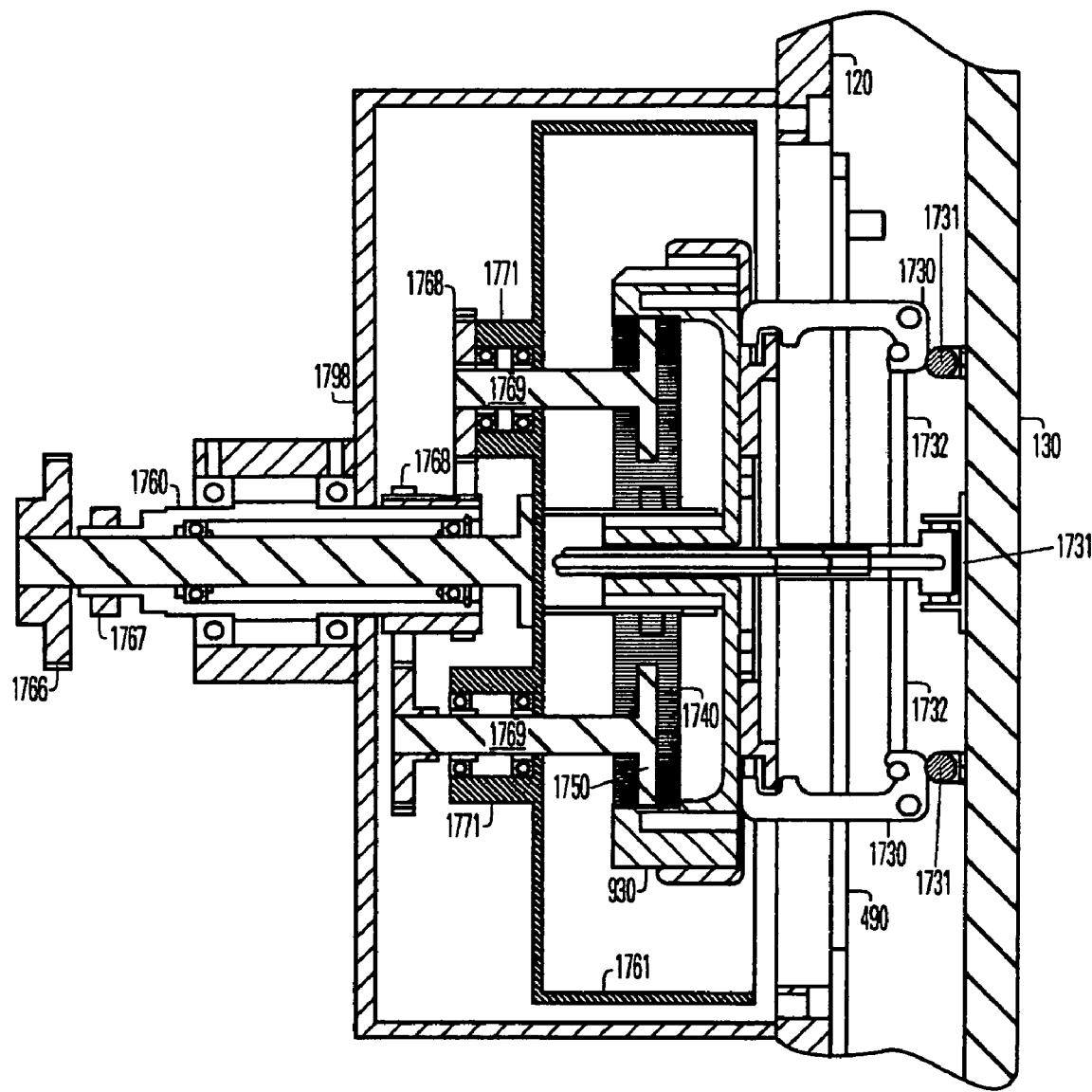
FIG. 31 is a view of the umbilical continuous flow centrifuge mounted to the console front panel.

The skiprope, also known as the umbilical, jump-rope or seal-less, approach, is the alternative to the face seal. Various apheresis systems currently use the skip-rope approach. This approach is shown conceptually in FIG. 27. The CFC disk 930, with separation channel 990, and cassette 490 are shown. The CFC disk 930 may be identical to that used in the face seal embodiment. However, in this embodiment, the means for transporting the fluid flows to and from the separation channel 990 are not ducts, as in the previous embodiment, but a flexible plastic or elastomeric umbilical 1670 connected from the rotating CFC disk 930 to the stationary cassette 490. This umbilical consists of a number of small tubes 1690, usually 3 to 5, depending on the function to be performed, bonded or twisted together, or an extended multi-lumen tube. These tubes or lumens 1690 carry blood and fluids between the input and output ports 1692 on the disk and the cassette 490. This umbilical or skip rope 1670 is rotated about the axis or rotation 1680 of the disk at one-half the speed (RPM) of the disk itself. This keeps the umbilical from twisting or winding up. The skip-rope umbilical 1670 should be as short as possible with an outermost radius of motion around the centrifuge disk 930 of about 3 inches or as small a radius as possible. Additionally, the length of the umbilical in the direction along the axis 1680 of the centrifuge disk should be as short as possible.

As with the face seal embodiment, there is inlet for whole blood into the CFC disk 930, outlets for concentrated red blood cells and plasma out of the CFC disk 930, along with inlet to provide red blood cells storage solution or other inputs. The umbilical 1670 may use low-cost extruded pvc tubing. In the design shown, two tubes have an inside diameter of about 0.060 to 0.012 inch for input of whole blood and outlet of concentrated red cells. One to three tubes have an inside diameter of about 0.030 to 0.060 inch for plasma out, possible plasma purge out, and possible storage solution into the disk 930. Thin walls of 0.015 to 0.03 inch may be used depending on the manufacturer and materials. The tubes are twisted together and may be adhesive or solvent bonded together.

A mechanism is necessary to provide the speed control, speed ratio, and the mechanical support for the umbilical 1670 and CFC disk 930. A major advantage of this approach is that there is no sealing interface with a potential to leak. The umbilical provides a completely closed and, once sterilized, sterile disposable set. This eliminates the possible risks of face seal leakage, particulates entering the blood from the seal, shear at the seal face, elevating face seal temperatures, and possible blood damage. The umbilical, because of its bending, twisting, and untwisting during use, possibly can heat up with time and result in blood damage. However, the short expected operating time of under 30 minutes with a maximum of 5000 RPM and good design are expected to avoid excessive heating. Obviously, the use of different materials may allow for longer operating time or faster operation without affecting the basic concepts of the invention.

Using the umbilical, the maximum donor blood flow is about 75 mL/min and the maximum inlet blood flow to the centrifuge disk 930 through the umbilical after anticoagulant addition is about 75 mL/min at a maximum hematocrit of about 50%. The maximum plasma flow is about 60 mL/min. The maximum packed red blood cell flow is about 42 mL/min at a hematocrit of about 90% (or 63 mL/min at a hematocrit of 60%, after storage solution addition).

The centrifuge drive mechanism, shown in FIGS. 28 through 31 is mounted on the front panel 120 of the console. This entire mechanism is not much larger than the centrifuge drive for a face-seal disk. The overall centrifuge mechanism ideally should be within a cylinder of less than 7 inches diameter by less than 9 inches long. The centrifuge disk 930 fits, and is locked into the drive cup 220 on the console 100, which drive cup 220 drives the centrifuge disk 930 at its required speed.

The disk 930 is supported on the 1-omega apparatus by a bearing assembly 1720 that is part of the disposable disk 930. The disk 930 is mounted or coupled to the cassette 490 in its sterile package before installation of the cassette 490 in the console 100. This simplifies cassette and disk mounting by making these two parts a single assembly mounted in one simple operation. When the cassette 490 is placed on the console front panel 120 and the door is closed, roller actuators 1731 in the door engages levers or locks 1730, biased by elastomeric element 1732, that de-mount the CFC disk 930 and allow it to rotate freely. When the door is opened, the coupling between disk and cassette 490 recurs. This makes removal a single, simple operation by handling only the cassette 490 with the disk attached to it.

Two pinion gears 1750 mounted on support bearings 1771 in the 1-omega mechanism engage an internal gear 1740 on the CFC disk 930 and drive it at 2-omega. These gears are mounted on two short shafts 1769 that are secured at 180 degrees apart to the umbilical drive cup 1761. This cup 1761 is driven at 1-omega by the internal shaft of dual concentric drive shafts 1760.

The dual concentric drive shafts 1760 have attached pulleys that are belt driven from two pulleys 1766, 1767 mounted on an electric motor shaft. The internal shaft of the two concentric drive shafts 1760 drives the umbilical drive cup 1761, which couples with and drives the umbilical at 1-omega.

The external tubular concentric shaft has two pulleys mounted to it that belt drivel 768 the two short shafts 1769 secured to the umbilical drive cup 1761. These shafts are secured but rotate freely in bearing assemblies 1771 that are part of or attached to the umbilical drive cup. These shafts have pinion gears 1750 that engage an internal ring gear 1740 that is part of the CFC disk 930. One such shaft and gear is adequate to directly drive the CFC disk 930, but two at 180 degrees apart are used for balance and safety via redundancy.

The concentric drive shafts rotate within a bearing block 1797 that is mounted to stationary hollow cylinder 1798 with one flat end. This cylinder 1798 is attached to the console front plate 120 and supports thereby the entire mechanism.

As another alternative, shown conceptually in FIGS. 32 and 33, rather than engaging an internal gear 1740 on the CFC disk itself, the pinion gears 1750 engage a similar internal gear 1741 on a disk drive cup 1762, which is mounted in the umbilical drive cup 1761. Toothless rotor support bearings 1752 provide additional stability and centering of the disk drive cup 1762. The disk drive cup includes a slot 1763 to allow the umbilical to be placed into the umbilical drive cup. The disk drive cup may then include pins 225 as described in connection with the cup 220 to hold the centrifuge disk in the cup when in operation. Persons of ordinary skill in the art will appreciate that other design alternatives are possible, including an external gear on the disk drive cup (or the CFC disk) surrounded by the drive gears and/or support bearings.

To reduce noise, gears and support bearings may be plastic or elastomeric.

The operation of the CFC 515 in separating blood will now be described.

Figure 34:
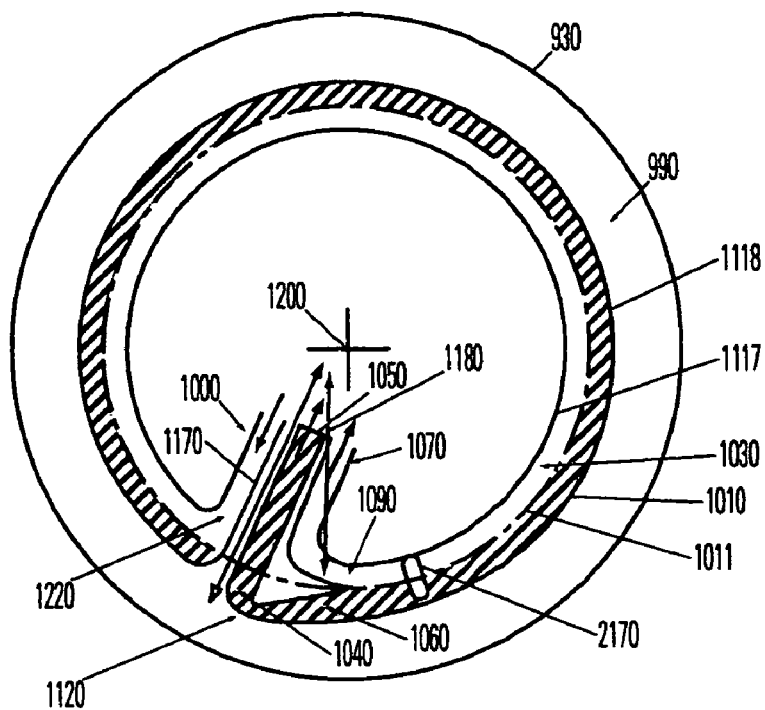
FIG. 34 shows a conceptual design for the continuous centrifuge disk separation channel.

The compact, disposable CFC disk 930 is designed to provide whole blood separation into red cell, plasma, and buffy coat components within an annular separation channel 990 and to remove these components from the channel and disk, meeting the various requirements for flow rate, hematocrit, blood component damage, and the contamination of plasma by cells. A conceptual design of the CFC disk 930 is shown in FIG. 34. Whole blood taken from the donor via the access needle 660 is anticoagulated and pumped into the CFC disk 930 via the whole blood entry duct 1000 and through an input port 1220 while the disk rotates around the axis 1200 at sufficient speed to rapidly separate incoming blood. The centrifuge disk 930 has an annular separation channel 990 near its outer periphery. Whole blood flows continuously during the donation into this separation channel 990, separates into components as the blood flows along the channel, and the components are removed at various ports along the channel. Concentrated red cells 1010 are separated to the outer (larger diameter) wall of the separation channel 990, platelets or buffy coat 1011 form on top of the red cell interface, and plasma 1030 separates to the inner wall 1117 of the channel. The red cells and plasma 1030 are removed continuously through ports and ducts to product bags. The platelets or buffy coat are collected in the channel until the end of the whole blood collection from the donor. Then the buffy coat either remains in the channel or disposable set or is removed from the channel to a buffy coat product bag.

In operation, as the first part of the donation process, the separation channel of the CFC disk 930 is primed. The CFC disk 930 has an annular separation channel 990 that has a volume of around 60 to 90 mL. This volume is initially filled with sterile air. The donor's whole blood is allowed to enter the separation channel 990 at an whole blood input port 1220 and displaces the air in the separation channel into a sterile air bag 1110, through a plasma port 1090, for use later in purging or removing blood components from the CFC disk 930 and disposable set. Priming may be accomplished at least two ways. When the cassette is initially mounted in the console, the plasma port 1090, through which plasma 1030 will be removed during the separation process, may be positioned to be above the blood filling the separation channel. The CFC disk is slowly "clocked" as the separation channel 990 fills with blood, keeping the plasma port 1090, which is positioned on the inner wall 1117 of the separation channel, above the liquid, and ultimately positioned at the highest point in the separation channel, that is, the point nearest the top of the console 100. Air is thus forced through the plasma port 1090, and may, through appropriate valve operation, forced into the sterile air bag 1110. Alternatively, if the separation channel is substantially circular and balanced, the CFC disk may be spun at a moderate speed, of, for example, between 1000 and 2000 rpm, while filing, forcing the air to the inner wall 1117 of the separation channel and out the plasma port 1090 as the separation channel 990 fills with blood.

The separation channel 990 is shaped to improve the separation and removal of red cells and plasma 1030. The channel outer wall 1118 increases in radius (from the axis of rotation 1200) in one region to be at or near its maximum distance or radius 1170 from the axis of rotation 1200 and thus form a collection pocket portion 1060 for red cells. The red cell pick-up port 1120 removes red cells at or near the bottom or largest radius 1170 of this pocket, at the greatest distance from the center of rotation. This increased radius increases the depth of the red cell layer (the radial distance from the red cell-plasma interface 1130 to the red cell pick-up port) and provides the maximum g-force and packing of red cells at this port. This maximizes the packed red cell hematocrit that can be achieved for cells removed through the red cell pick-up port at any given rotational speed of the disk. The deep red cell layer also minimizes the pulling of plasma 1030 through this layer to the red cell pick-up port.

Figure 35:
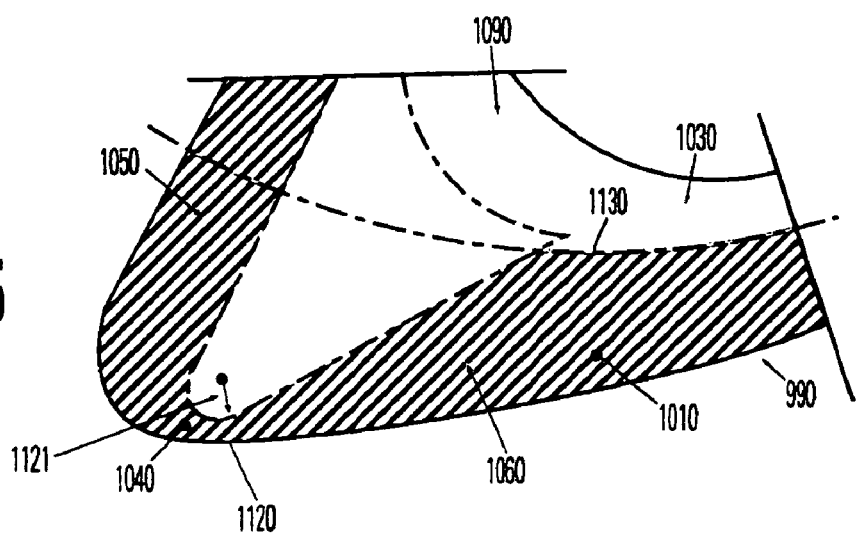
FIG. 35 shows conceptually a detail of the separation channel.
Figure 36:
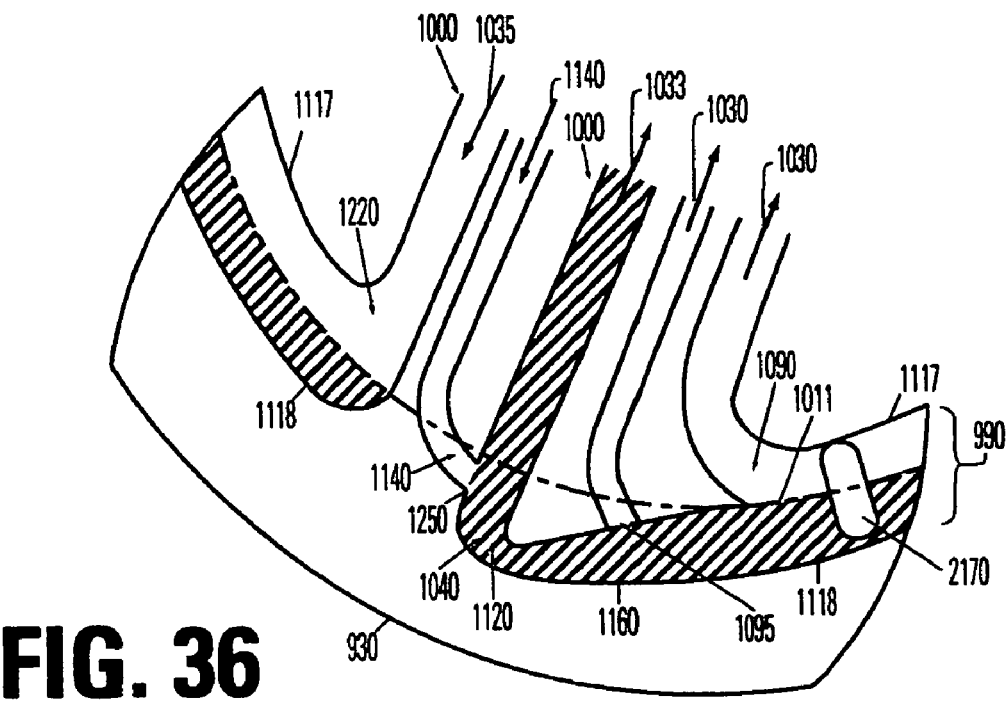
FIG. 36 shows a detail of the continuous flow centrifuge separation channel with two plasma pickup ports.

FIGS. 35 and 36 show designs for the packed red cell removal region. A narrow gap 1120, of a width substantially less than the average radial width of the separation channel 990, and generally between 10 to 30 mils, is provided over part or all of the separation channel 990, at the deepest, that is the largest radius 1170 from the spin axis 1200, part of the channel and of the red cell collection pocket portion 1060. This gap 1120 is used to pull red cells from the deepest part of the pocket where they are most highly packed, to a high hematocrit (about 90%). This narrow gap 1120 ensures that red cells are removed from the highest hematocrit region of the concentrated red cells 1010. The gap is narrow enough to cause a slight restriction and ensure that lower-hematocrit red cells or plasma 1030 from near the red cell-plasma interface 1130 does not channel through the concentrated red cells 1010 and out this removal port. The radial distance from the red cell-plasma interface 1130 to the packed red cell removal port 1040 is made sufficiently great to prevent such channeling and maximize red cell hematocrit.

The length of this gap is maximized in the axial direction, that is, essentially parallel with the axis of rotation, so that the flow velocities are low, to avoid damage to the red cells. Further, the entrance to the gap may be defined by material having a radius 1121 that is greater than or equal to the width of the gap 1120 to prevent damage to the red cells and reduce the pressure drop.

The channel inner wall 1117 may decrease in radius 1180 from the axis of rotation 1200 to form a plasma pocket portion 1100 where plasma 1030 can flow through an output port 1090 into a substantially radial plasma removal duct 1070, which can include other fluid transportation means such as a tube, that transports the plasma toward the center of the disk 930 for removal to the cassette 490. The decreasing radius at an increasing cross-sectional area for plasma flow results in a reduced plasma flow rate and the final opportunity for stray cells to separate out of the plasma stream before plasma 1030 is removed.

With reference to FIG. 36, the red cell storage solution 1140 may be added to the concentrated red cells at a storage solution port 1250 just after they pass through the red cell pick-up port 1040. Storage solution is metered into the flowing concentrated red cells at an approximately constant ratio, controlled by the microprocessor and software via the storage solution pump and red cell pump 701. The storage solution is introduced into the red cells at a slightly smaller radius from the spin center than the red cell port 1040. The addition of storage solution decreases the packed red cell hematocrit from about 90% to about 60%, and greatly reduces its viscosity and density. This permits red cells to be removed from the CFC disk 930 with lower pressure drops, less negative pressure, and lower red cell damage in the seal pump and tubing when the red cells are pumped out of the CFC disk 930 through the face seal. In particular, the procedure reduces the hemolysis caused by the red cells passing through a shear region between the rotating and non-rotating tubular segments at the axial center of the seal assembly and also reduces cavitation.

Figure 38A:
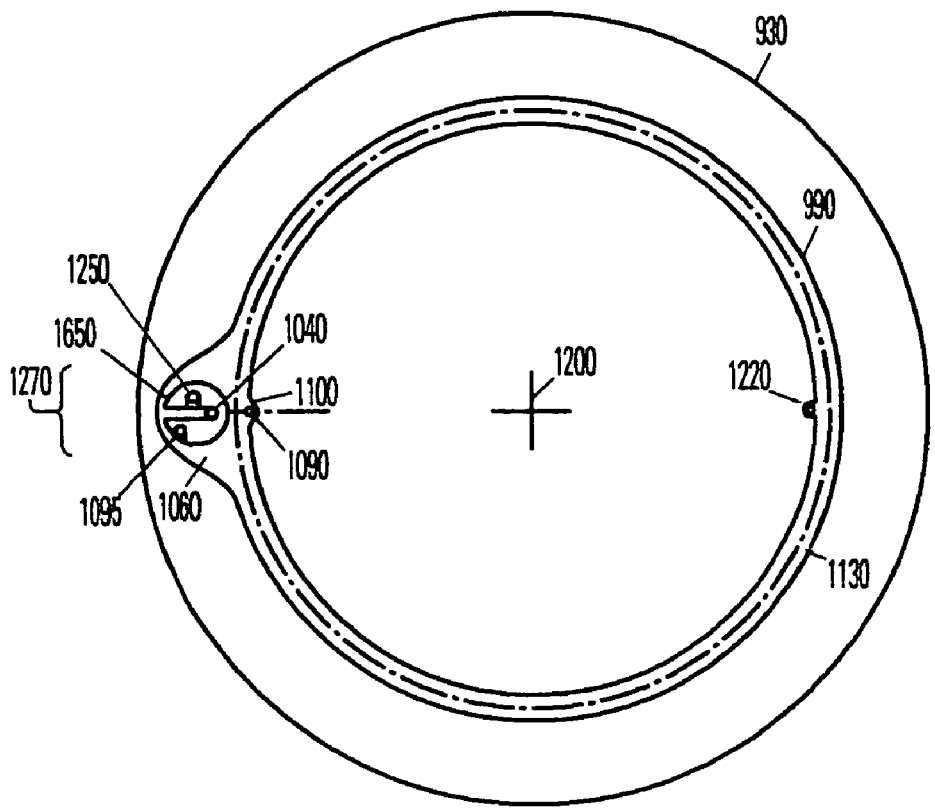
FIGS. 38A and 38B show the continuous centrifuge disk with a second design for a separation channel.
Figure 39:
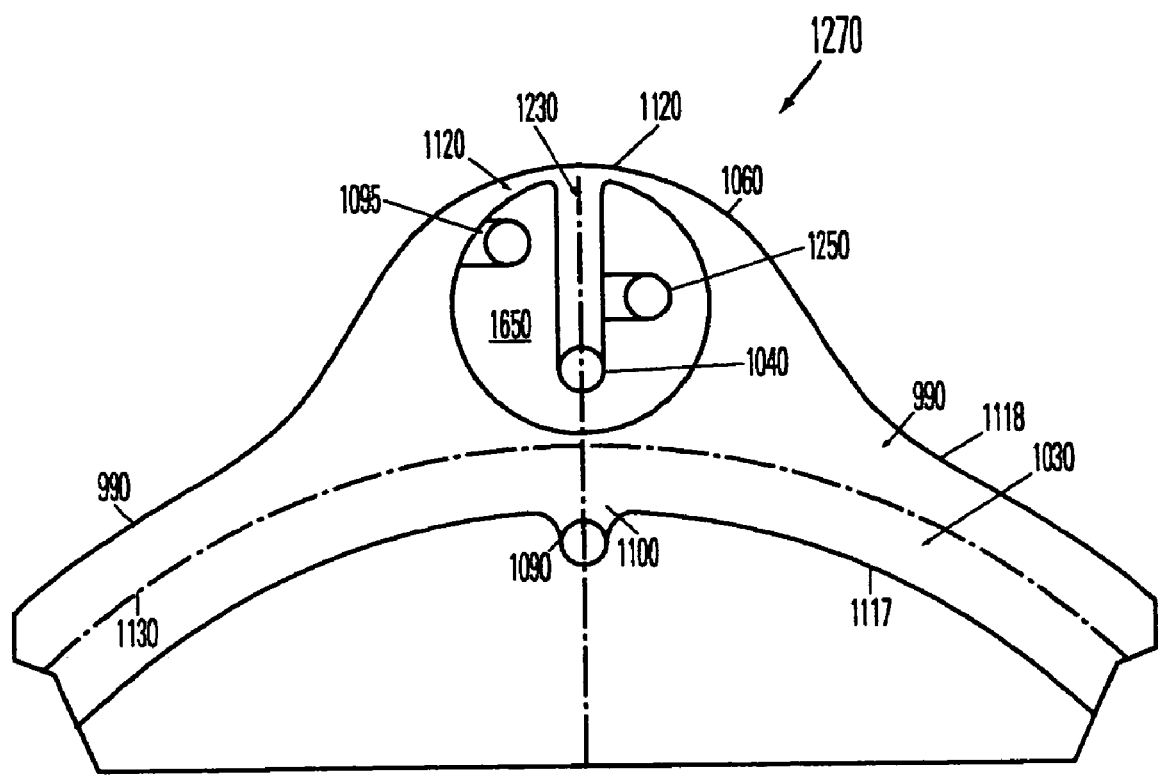
FIG. 39 shows a conceptual detail for the third design for a separation channel.

Once donation is complete, the system must be purged. There are several ways of performing this task. In the first method, plasma 1030 is removed from the plasma removal duct 1070 during steady-state continuous flow operation. When donor whole blood flow into the whole blood entry duct 1000 stops at the end of the donation, the separation channel 990 is filled with separated blood. The red cell pump 701 continues to remove red cells from the red cell collection pocket portion 1060 until all red cells are removed while disk rotation continues at a high speed. Plasma 1030 is allowed to flow back from the plasma bag and fills the separation channel 990. The separation channel 990 is now filled with plasma 1030. However, there are residual red cells loosely adhering to the walls of the separation channel 990. This prevents draining the plasma 1030 out the plasma removal duct 1070 while slowly rotating the disk because the residual red cells will mix with this plasma and overly contaminate it. It is also not feasible to pump the plasma 1030 out of the concentrated red cell removal duct 1050 because this duct is filled with red cells. An excessive amount of plasma would be needed to clear out or purge the red cells sufficiently to avoid excessive red cell contamination of the plasma 1030. Therefore, as shown in FIGS. 38A and 39, a second plasma removal duct 1080 and port 1095 may be added to the disk 930 specifically to remove plasma 1030 during the purge process when the separation channel 990 is filled with plasma 1030. In the embodiment shown, the second plasma removal port is added in an "island" 1650 near the red blood cell "pocket" portion 1060 of the separation channel 990. The disk 930 is rotated at a moderate speed and sterile air, which was collected in an air bag 1110 during disk priming, is used to replace the plasma 1030 in the separation chamber as plasma 1030 is removed through the second plasma removal port 1095. The air pressure may be great enough to force the plasma 1030 out of the disk or a pump may be used to pull the plasma out of the disk.

The second plasma removal port 1090 is located sufficiently far from the outer wall 1118 to avoid picking up red cells from this wall. Centrifugal forces from disk 930 rotation keep the cells against this outer wall 1118. The red cell collection pocket portion 1060 size and shape, and the location of the plasma purge port 1095, result in a plasma volume not recoverable from the separation channel of less than a milliliter.

As an alternative process for purging the disk 930 after the donation is completed air can be used to perform the purge without use of plasma 1030 from the plasma bag 630. Once the donation is complete, no more blood is entering the CFC disk 930. The last few minutes of the donation are used to push all of the plasma 1030 out of the disk 930 by slowing the pumping action of the rotor on the tubing segments and letting the red cell-plasma interface 1130 move toward the inner surface of the separation channel 990 until, by the end of the donation, all plasma 1030 has been expelled from the disk 930. Air then enters the channel from the sterile air bag 1110 to displace red cells, and the red cells are pumped out of the disk 930 either while spinning at a low RPM or with the disk 930 stationary and the red cell removal port 1040 located at the lowest point with respect to gravity.

As another alternative process for purging the disk 930, near the end of donation, red cells are allowed to fill the separation channel as plasma 1030 continues to be removed, forced from the channel by the increasing amount of concentrated red cells. Once the plasma 1030 is removed, the buffy coat, identified thorough use of an optical sensor 2170 placed near the plasma removal port may also be removed through the plasma port 1090, but directed into a collection bag or other receptacle This process has the advantage of not requiring an additional plasma removal port. The donation is stopped, but anticoagulant is allowed to flow into the separation channel 990 through the whole blood port 1220 and the red blood cells 1033 are removed from the separation channel through the red blood cell removal port 1040. As an alternative, air collected during the purge process may be used in place of the anticoagulant, but potential imbalance in the CFC disk then requires that a slower disk rotational speed be used. It will be noted that with the current disk designs, anticoagulant is usually convenient to use for the purge; however, it might be possible to use other fluids in the system such as storage solution in a similar manner.

The separation channel design, including the location of ducts, and disk rotational speed are key to achieving the desired separation requirements. FIGS. 37, 38, 42, 43, 44, and 45 show various alternative designs for the substantially circular separation channel, in that the axis of rotation 1200 is the center of a circle approximately defined by those portions of the separation channel that are not in the pocket portions 1060, 1100. It is not necessary, however, that the separation channel extend for a full 360 degrees, or that the channel be unbroken, although as noted below, such a design may have certain advantages. A circular separation channel may be less effective in removing all red cells rapidly in a purge process compared to an outward spiral design shown below in FIGS. 47, 48, and 49 if air is used to purge the disk. However, a substantially circular channel functions well if the anticoagulant method of purging is used.

In all the designs, the whole blood enters the separation at a port 1220, concentrated red cells 1010 are picked up in port 1040 from a pocket portion 1060 positioned at the largest radius 1170 or point furthest from the axis of rotation 1200, and plasma 1030 is removed at the plasma port 1090 other end of the separation channel 990. In all of these embodiments although not shown, storage solution 1140 may be added at the red cell storage solution port 1250 or along the red cell storage solution duct 1251 to the concentrated red cells in the red blood cell removal port 1040.

In all of the designs a variety of radial fluid conduits 1001 may be used. For example the ducts 1070, 1050, 1251 and 1000 may be machined in the disk body 1150 substantially extending toward the center of the disk 930. The ducts are sealed at 1151 by the disk cap 1500. These fluid ducts carry whole blood to the separation channel 990 from the central face seal. Plasma and concentrated red cells are carried by these ducts from the separation channel 990 to the face seal. Alternatively, tubing is used in the skip rope CFC design, but tubing may also be used as a radial fluid conduit in the face seal design.

Figure 38B:
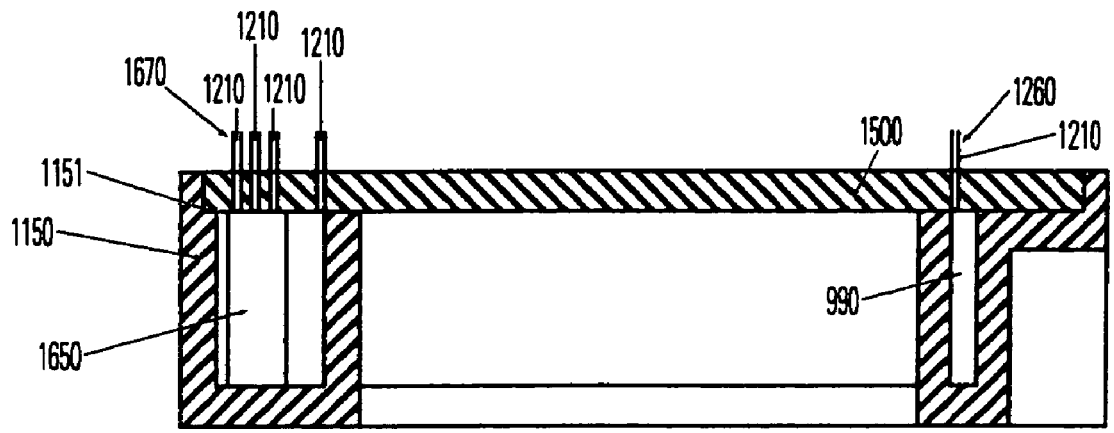

FIGS. 38A, 38B and 39 show a CFC disk 930 specifically designed for umbilical tubing 1210 attachments. This design assumes that red cells are removed first during the purge, and that plasma is removed from a separate port 1095 near the red blood cell removal port 1040 after red cell removal. Storage solution is added at the red cell storage solution port 1250 to the concentrated red cells in the red blood cell removal port 1040. Whole blood enters at the whole blood entry port 1220 through a tube 1260 which is connected to the separation channel 990 and which is 180° away from the blood component removal region 1270. Whole blood is divided into two paths that are on either side of the tube 1260. This reduces (by half) the flow rate in each 180° channel segment and may improve red cell-plasma separation. Concentrated red blood cells 1033 are channeled through a pocket formed by an island 1650 in the separation channel 990 and through narrow gap 1120 which function as described above in connection with FIG. 35, into a slot 1230 formed in the island 1650 with an opening toward the outer wall 1118 of the separation channel 990. The slot entrance does not extend the entire axial length of the separation channel, that is, in the direction parallel to the axis of rotation. Generally, the slot represents 50% to 90% of the length. Alternatively, holes can be placed at the entrance rather than a slot. Storage solution may be added into the slot 1230 through a red blood cell storage solution port 1250 and blood cells are then removed through a red blood cell removal port 1040. Plasma is removed through a plasma removal port 1090 during steady-flow, which may be positioned on the inner wall 1117 of the separation channel 990 as shown, or alternatively (not shown) on that portion of the island 1650 closest to the inner wall, and is removed through a separate port 1095 during the purge process which may be placed on the island outside the gap 1120, but near the outer wall 1118 of the separation channel. Umbilical tubing 1210 attaches to the ports at or near the whole blood entry port 1220 and the blood component removal region 1270. However, ducts to a face seal as described above can also be used instead of an umbilical, with the same separation channel and component removal design features.

Figure 42:
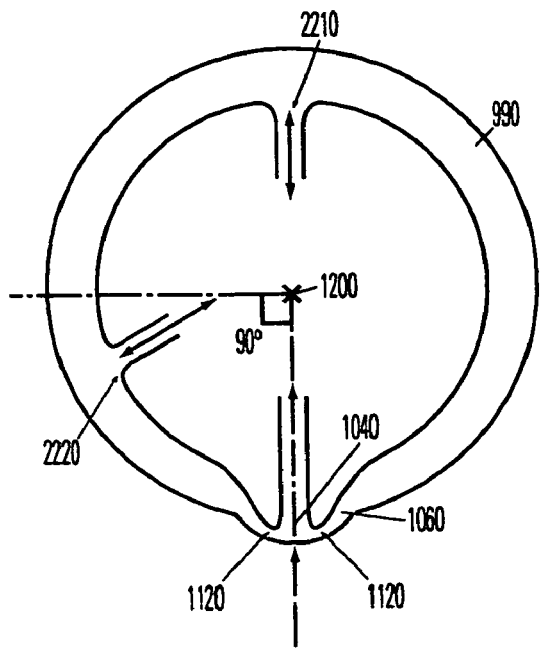
FIG. 42 shows the continuous centrifuge disk with a fourth design for a separation channel.
Figure 43:
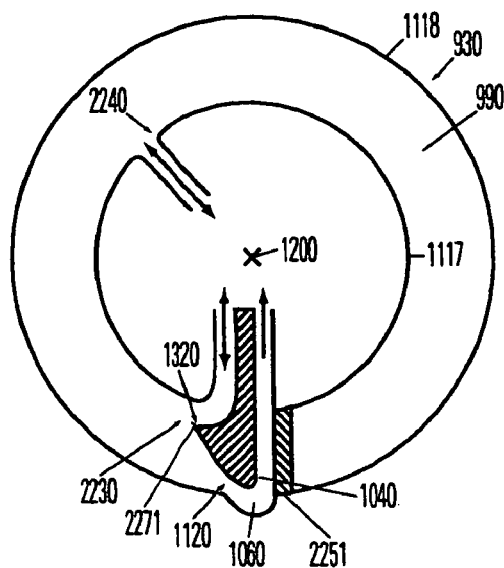
FIG. 43 shows a continuous centrifuge disk with a fifth design for a separation channel.
Figure 44:
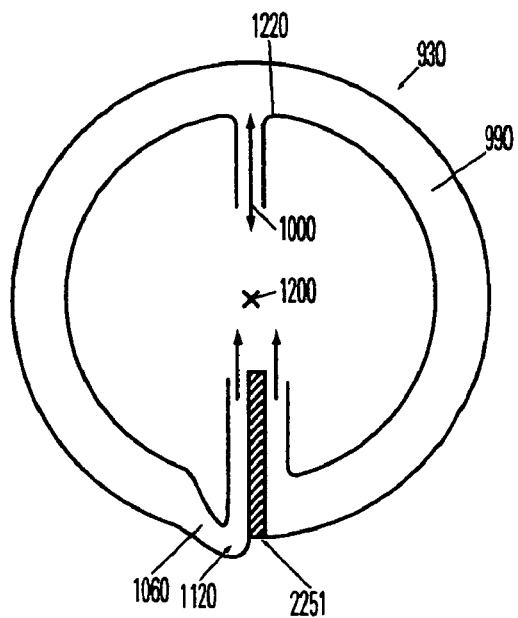
FIG. 44 shows a continuous centrifuge disk with a sixth design for a separation channel.

FIGS. 42, 43, and 44 show alternative designs for a circular separation channel 990. Each of these embodiments has radial inlet and outlet ducts. FIG. 42 shows a CFC disk 930 with features such as a collection pocket portions 1060 and narrow gaps 1120. The system can be designed such that whole blood enters at a port at point 2210, 180° from the red blood cell removal port 1040 and plasma is removed at a port at point 2220 at an angle less than 90° from the red blood cell removal port 1040, or alternatively, whole blood can enter at point 2220 and plasma can be removed at point 2210.

The embodiment of FIG. 43 also includes two ports that may alternatively be used for plasma removal or whole blood introduction depending upon the connections made to the manifold. One port is positioned at point 2230 adjacent and parallel to a red blood cell removal port 1040, while the other port at point 2240 is positioned at an angle of from 90 to 270 degrees relative to the red blood cell removal port 1040. An internal barrier wall 2251 is positioned adjacent and parallel to the red blood cell removal port 1040, but on the opposite side of the red blood cell removal port 1040 from point 2230. The embodiment may also include a red blood cell collection pocket 1060 and gap 1120, and may also include a knife edge diverter 1320 which is further described below.

In FIG. 44, a whole blood entry port 1220 is positioned 180° from the red blood cell removal port 1040. A plasma removal port 1090 is positioned adjacent and parallel to the red blood cell removal port 1040. The two ports are separated by an internal barrier wall 2251. As with the embodiment shown in FIG. 43, a narrow gap 1120 and pocket portion 1060 may be included to assist in the separation of the concentrated red blood cells 1033.

Figure 45A:
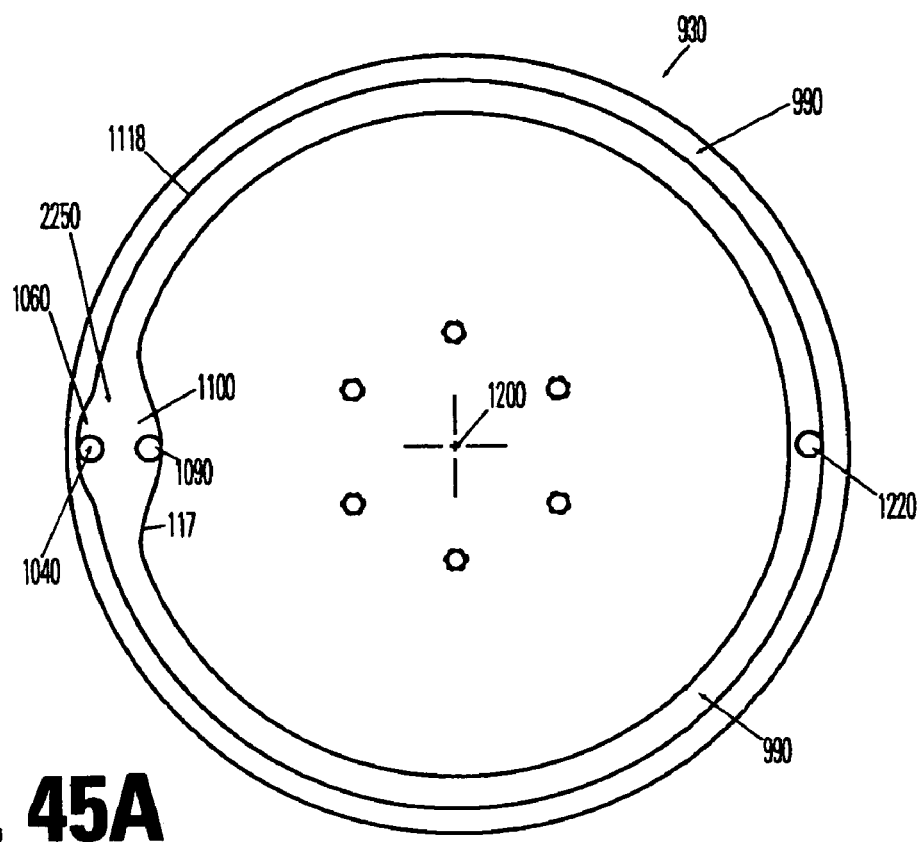
FIGS. 45A and 45B show a continuous centrifuge disk with a seventh design for a separation channel.
Figure 45B:
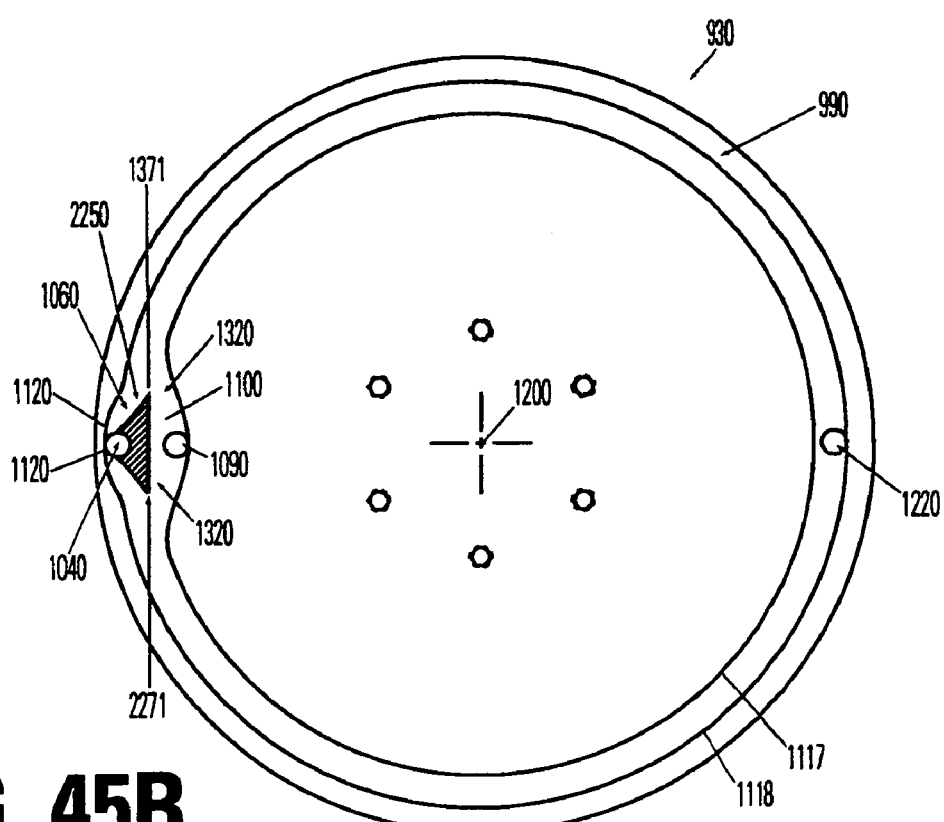

Finally, in FIGS. 45A and 45B, a circular separation channel 990 without a barrier is used. The red blood cell removal port 1040, in a pocket portion 1060 formed in the outer wall 1118 is positioned 180 degrees from the whole blood entry port 1220. Also at 180 degrees from the whole blood entry port 1220, but positioned in a pocket portion 1100 in the inner wall 1117, is the plasma removal port 1090. This design has similar advantages to the design shown in FIG. 38: for example, whole blood is divided into two paths at the whole blood entry port 1220 reducing by half the flow rate in each 180° channel segment and potentially improving red cell-plasma separation. Optionally, as shown in FIG. 45B an island structure 2250 may be used. The island 2250 allows the formation of narrow gaps 1120 near the entrance to the red blood cell removal port 1040. Furthermore, in either design storage solution may be added through a storage solution port 1250 at or just inside the red cell removal port 1040. The storage solution can be delivered through an appropriate conduit similar to that shown in the conceptual design of FIG. 36.

Figure 37:
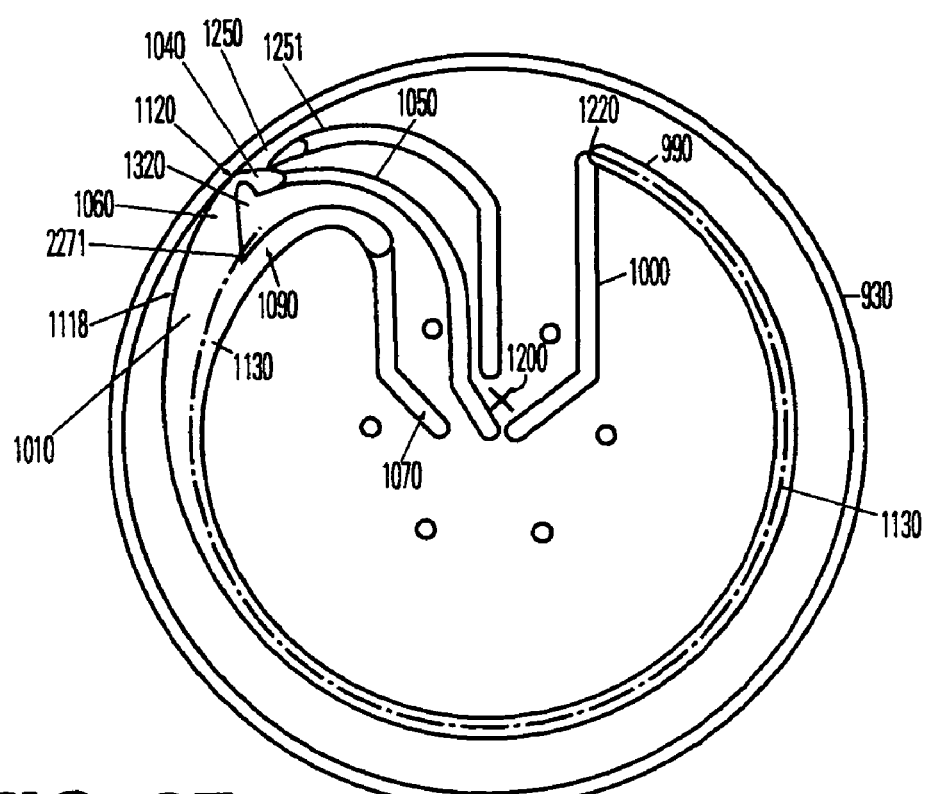
FIG. 37 shows the continuous centrifuge disk with a first design for a separation channel.

In all designs in which an island structure 2250 or an extension from the inner wall 1117 is practical, a knife edge diverter 1320 may be used to separate plasma from the concentrated red cells 1010 and buffy coat 1020. The point 2271 of the knife edge diverter 1320 is at a slightly smaller radius from the center of rotation 1200 than the radius of the red cell—buffy coat—plasma interface 1130 as shown in FIG. 37. This helps to prevent buffy coat and red cells from mixing with the plasma in the region where plasma is removed from the separation channel. The plasma in the channel from this diverter 1320 to the plasma pick-up 1090 spirals or steps inward to ensure only plasma is in this channel; red cells will separate out from plasma in this channel segment and move upstream under centrifugal forces to return to the channel segment containing red cells.

Figure 46:
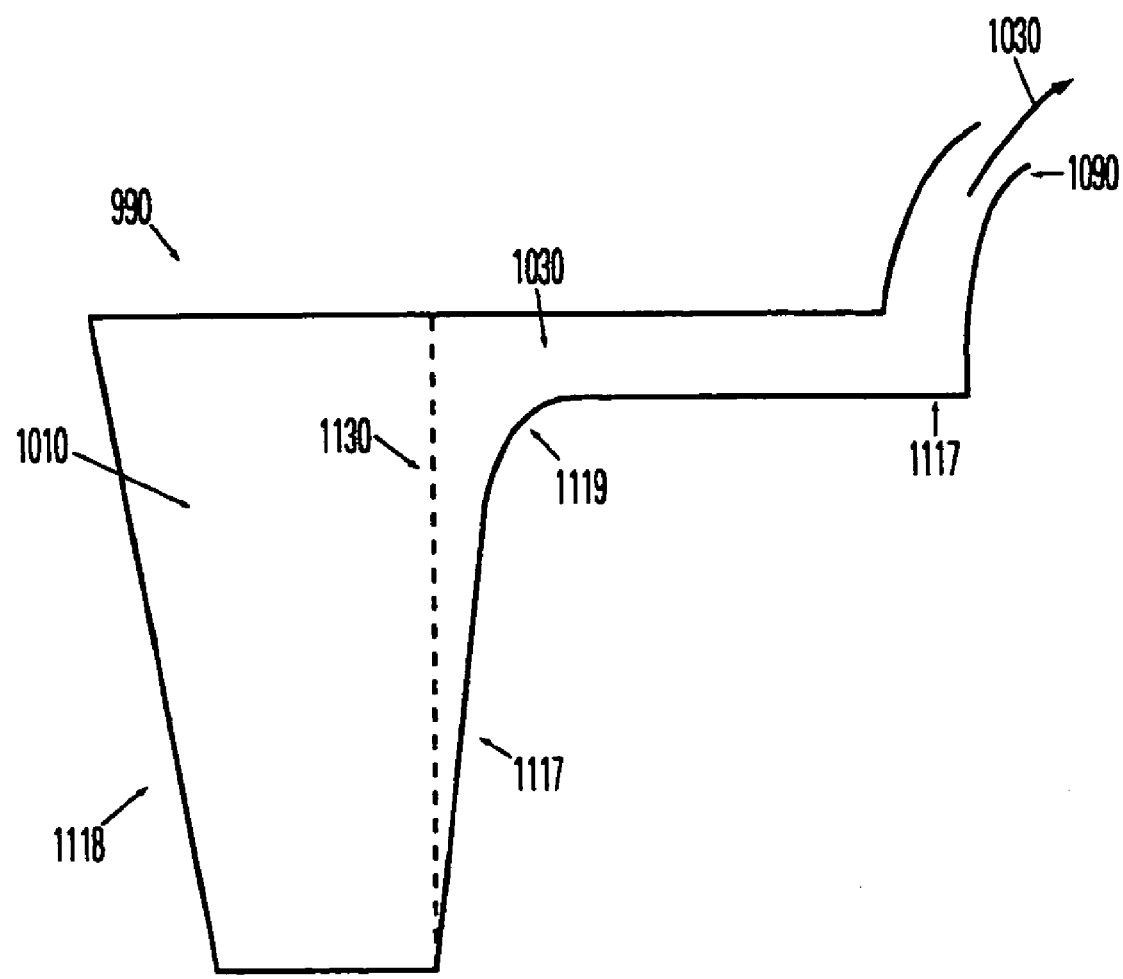
FIG. 46 shows a conceptual representation of an improved channel design.
Figure 47A:
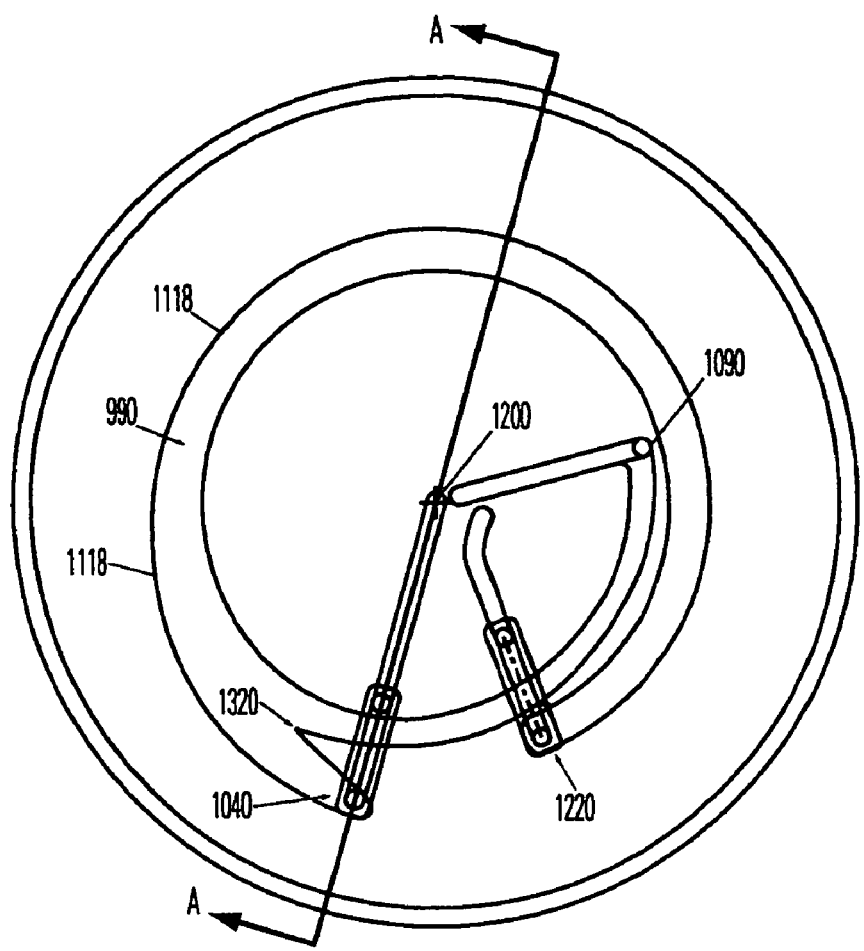
FIGS. 47A and 47B show an eighth separation channel design.
Figure 47B:
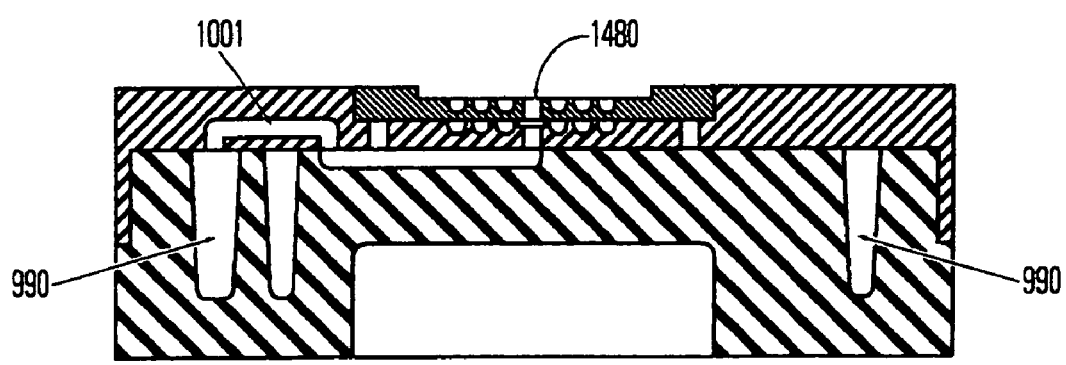

With reference to FIGS. 38B and 47B, current standard designs for separation channels usually have inner and outer walls 1118 that are substantially parallel with each other as shown in 38B or slightly tapered, as shown in FIG. 47B. However, control can be improved, for example in the purging process, by utilizing a cross-sectional shape similar to that shown in FIG. 46. The walls of the separation channel are generally tapered, and the channel 990 becomes substantially "shallower" at the inner wall 1117, as the inner wall 1117 forms a rounded edge 1119. By placing the plasma removal port 1090 within the shallower section of the inner wall 1117, and the red blood cell removal port at the "deeper" section of the channel 990 and at the outer wall 1118, mixing or contamination of plasma 1030 and red blood cells 1010 is less likely, given the position of the plasma—red blood cell interface 1130 relative to the channel and the ports.

Figure 40A:
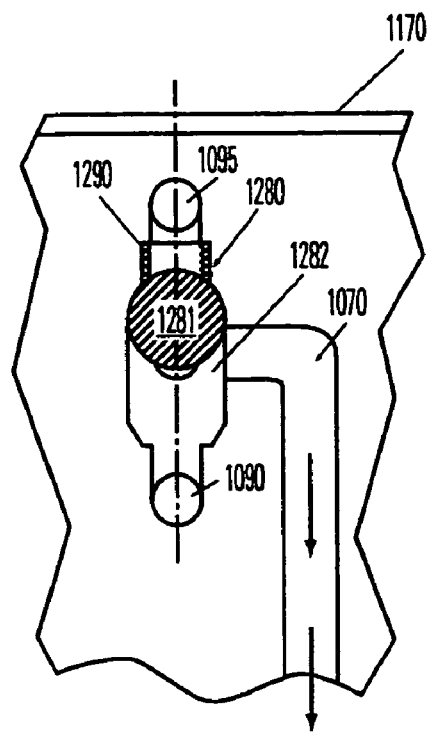
FIGS. 40A and 40B show a design for the plasma port that includes a ball valve in a first position.
Figure 40B:
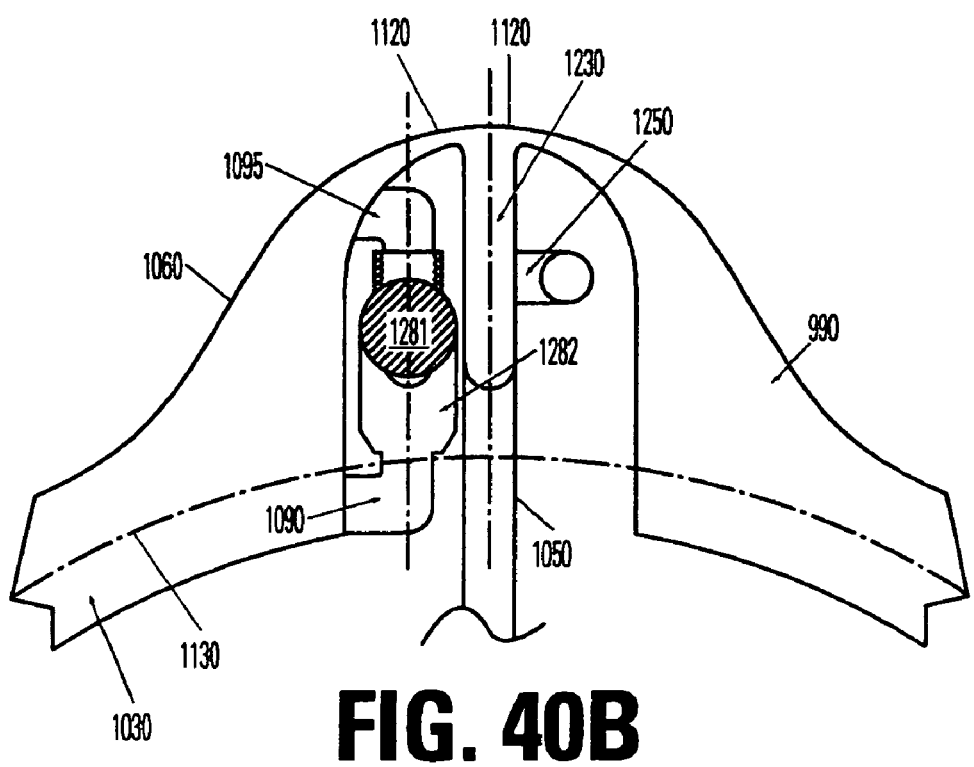

An alternative design for the removal of plasma in the separation channel 990, one during steady flow and one during the purge, is shown in FIGS. 40 and 41. A spring-loaded 1290 ball shuttle valve 1280 is used to control which port 1090, 1095 removes plasma. The ball shuttle valve 1280 includes a ball 1281 attached to a spring in a housing 1282 with three openings. One opening is attached to the plasma removal port 1090 for continuous flow another is connected to the plasma removal port 1095 for purging. The third opening is connected to a plasma removal duct 1070 or similar structure. During steady state continuous flow operation shown in FIG. 28, the CFC disk RPM is high (perhaps 4000 to 5000 RPM) and the g-forces on the ball 1281 compress the spring and close the purge port, with the steady flow port open to remove plasma 1030.

Figure 41A:
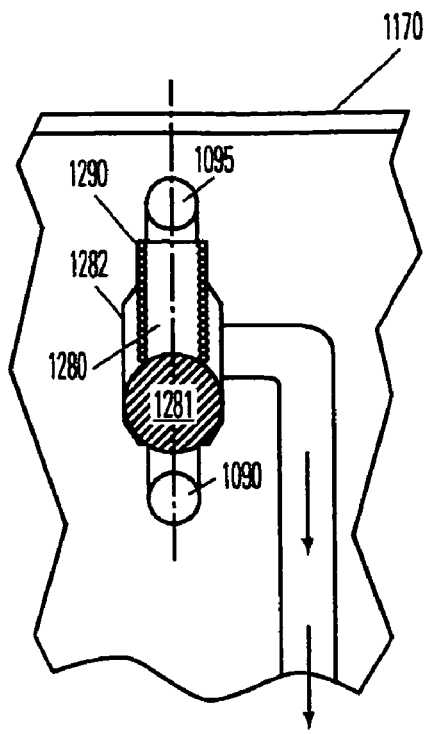
FIGS. 41A and 41B show a design for the plasma port that includes a ball valve in a second position.
Figure 41B:
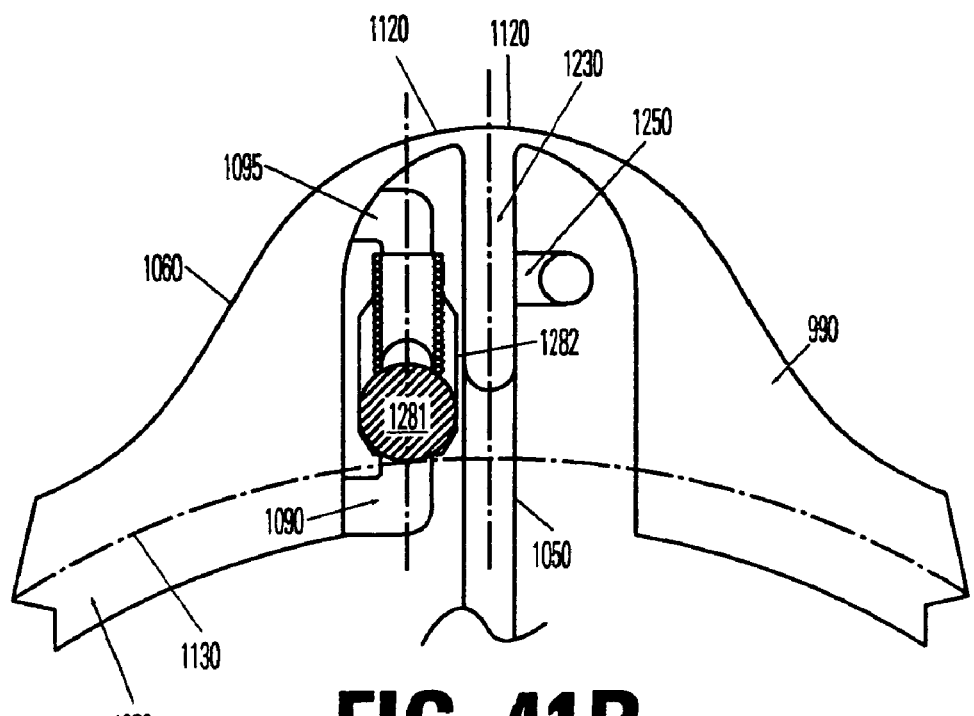

During the purge shown in FIGS. 41A and 41B, the RPM is dropped substantially (to perhaps 1000 RPM). This permits the spring force to overcome the g-force and the ball shuttle valve 1280 closes the steady flow port 1090 and opens the plasma purge port 1095. The plasma 1030 is either pumped out during the purge, or the pressure of air (entering the separation channel and displacing plasma) is used to force the plasma out as was described above in other embodiments.

It is not necessary that the separation channel be centered on the axis of rotation of the disk or be circular. FIGS. 47A and 47B show a separation channel 990 that extends about 420 degrees. This channel 990 may, as shown, have an outer wall 1118 spiral of increasing radius from whole blood entry port 1220 to concentrated red cell pick-up at port 1040, and the channel may be of decreased radius from the whole blood entry port 1220 to collect plasma at port 1090. The design may optionally include other features discussed above, such as a knife edge divider 1320.

Figure 48A:
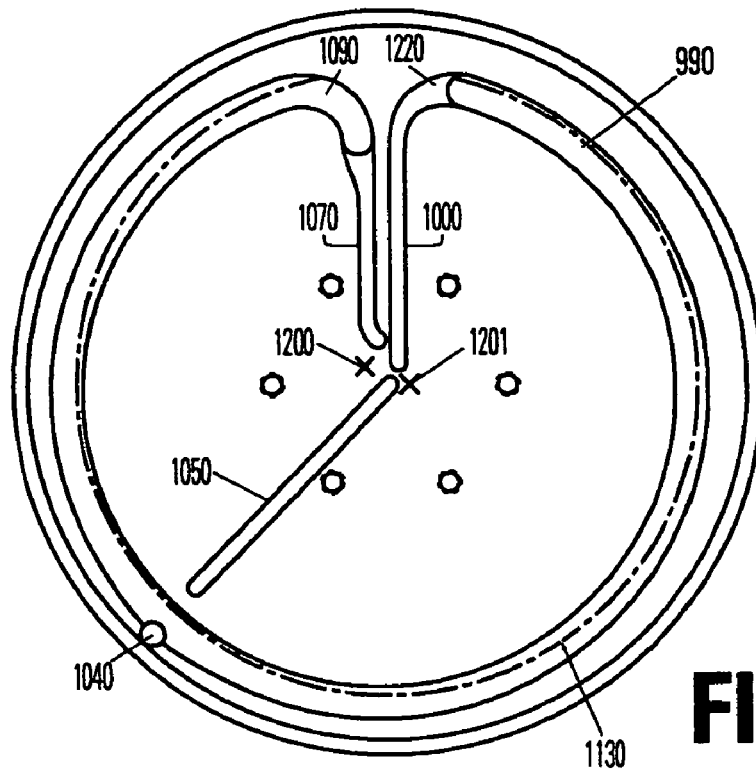
FIGS. 48A and 48B show an ninth separation channel design.
Figure 48B:
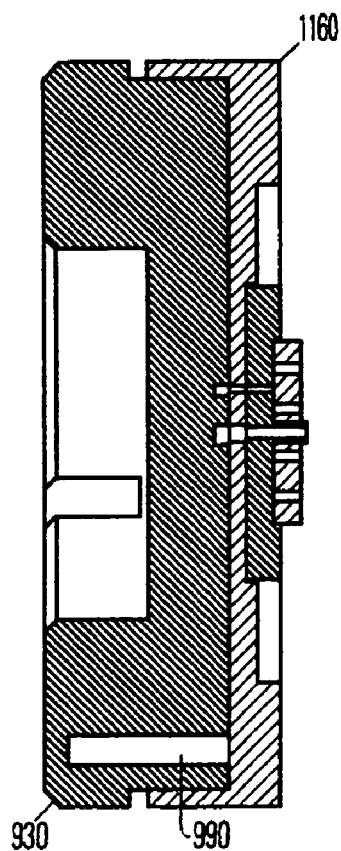

FIG. 48 shows a CFC disk 930 with a slightly spiral separation channel 990 that extends approximately 360° around the CFC disk 930 periphery. The design is substantially circular in that is it is based on a circle 1190, but unlike the circular embodiments described above, the centerpoint of the circle 1201 that is defined by the separation channel 990 is offset from the axis of rotation 1200 and the channel 990 may spiral inward slightly at the plasma port 1090. In some cases, the inward spiral may be continued past 360° to form two concentric separation channels for a portion of the disk.

Figure 49:
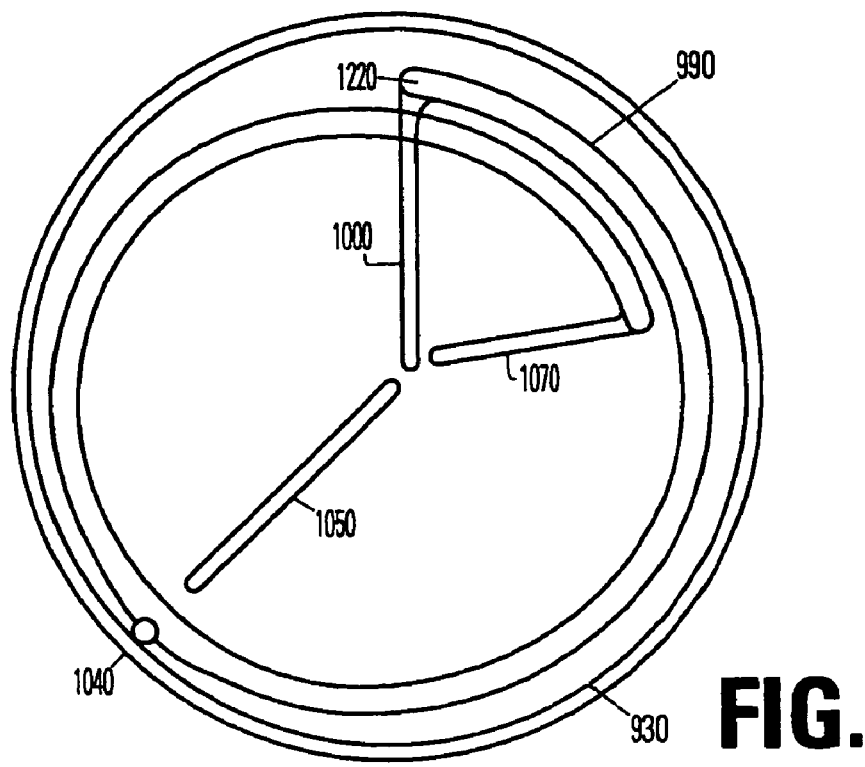
FIG. 49 shows a tenth separation channel design.

FIG. 49 shows a CFC disk 930 with another separation channel design where the separation channel 990 extends beyond 360° to 420°. The reasons for extending the channel are to provide greater separation path length for red cell packing or concentration, achieving a higher hematocrit packed red cell product 1010, or a greater separation path length for plasma 1030 (and a smaller radius) to obtain better plasma removal with cellular contamination.

Optical Sensor Control of the Red Cell-Plasma Interface

Figure 50:
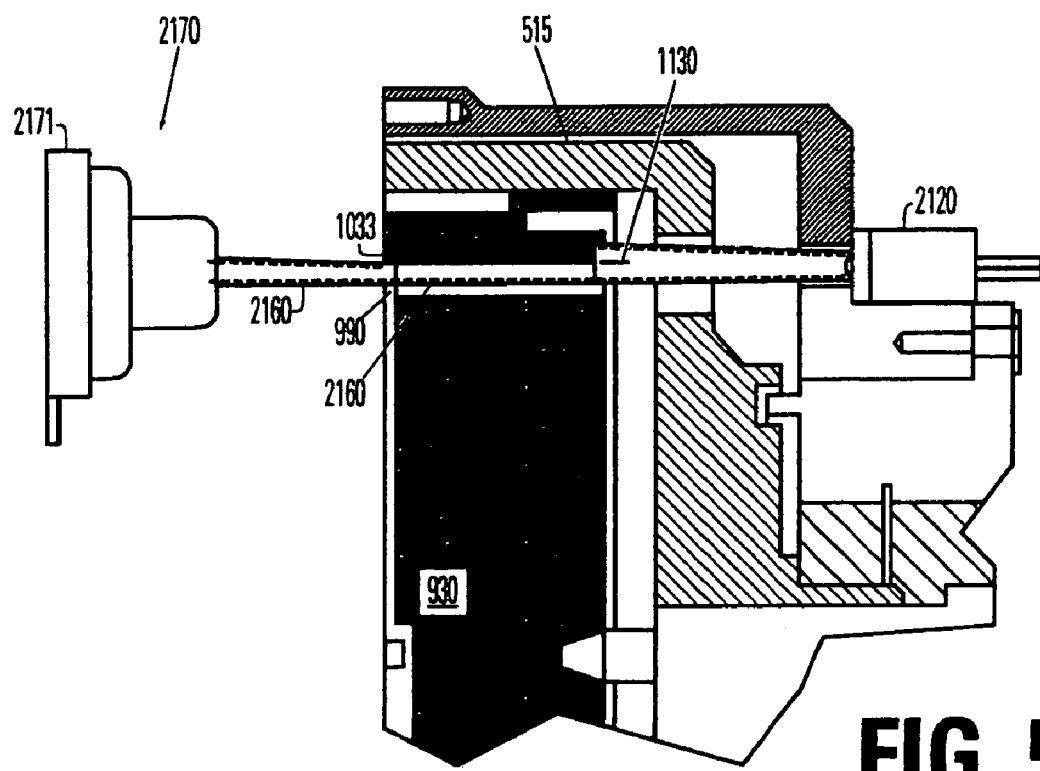
FIG. 50 is a cutaway view of a light detector for use in determining the red blood cell/plasma interface in the continuous flow centrifuge.

FIG. 50 shows the design concept used to detect and measure the location of the plasma-red cell interface within the separation channel of a rotating centrifuge disk 930 using a sensor 2170 incorporating an optical detector 2171. A light source 2120 is turned on for a very short time (an arc of about one degree) each rotation of the CFC disk 930 to illuminate a short angular segment or region of the separation channel 990 across all or part of the radial width of this channel. FIG. 50 shows a location of this optical sensing region. The red cell layer 1033 and buffy coat (not shown) block the passage of light but the plasma layer 2160 transmits this light to an optical detector 2171. The optical detector 2171 receives an amount of light proportional to the radial width of the plasma 2160 in the separation channel 990 determined by the location of the red cell/plasma interface 1130. Then the analog detector output increases when this interface moves radially outward and decreases when it moves radially inward. This detection of the interface location is used during continuous-flow operation in a feedback loop to control the ratio of the red blood cell pump flow rate which removes red blood cells 1033 from the centrifuge to the whole blood pump flow rate which pumps whole blood into the centrifuge. As this ratio increases, the red cell interface moves radially outward. In operation a desired reference interface location is established for a particular process (for example, maintaining the interface at a particular position relative to the point of a knife edge diverter) and the actual location of the interface 1130 is measured by the described optical means. The error signal of actual minus reference location, which are the optical analog values, is used to change the flow ratios described above in proportion to the error signal with appropriate time constants or averaging. This system and method can thus maintain the red cell-plasma interface 1130 in its desired location. Another optical detector 2171 can be placed to provide information about the conditions just outside the plasma removal port 1090.

As noted above, the centrifuge and cassette components may be made of clear plastic to allow for the use of optical detectors. To prevent scattering, it may be advantageous to place an opaque barrier on the disk and/or cap in the region of interest. The opaque barrier includes a hole so as to more precisely direct the light beam from the light source 2120.

An optical detector 2171 may also look at one or more additional regions in the separation channel 990. One additional region may be identical to the first measurement region but is modified to provide an accurate radial distance calibration. An additional opaque barrier may be added over the red cell portion of the separation channel in this region. This barrier extends into the plasma portion of the channel to provide only a plasma radial distance seen by the optical sensor. This fixed distance and the optical output represent a fixed hematocrit. This can be used to calibrate the optical sensor output in the measurement region. Such a calibration will compensate for changes in plasma transmissibility, light source intensity, light scattering, and light absorption through CFC disk surfaces.

Specific Processes

The current invention is able to use one console or electromechanical instrument to perform multiple blood collection and separation processes. Each process requires a different disposable set or product specifically designed to implement that process in combination with specific software for each processes.

For all processes shown schematically in FIGS. 51–59 the disposable set 480 is removed from a sterile package and hung on the pins of the console 100. Solution bags, such as anticoagulent, red blood cell additives, and saline are either attached by the operator using the Luer-lock, spike or other attachments means. The bags could also be preattached. Bacterial, for example 0.2 micron, filters may be placed in the flow paths from these bags to ensure the maintenance of sterility. The bags are hung in designated locations on the console 100.

The console 100 "calibration" button is pushed and calibrations and system software status are checked. Data collection may be performed manually by the operator using a bar code wand reader (not shown) and automatically via the bar code reader 275 console 100.

The operator places the access needle 660 in the donor's vein and after the blood samples, which are not anticoagulated, are taken from a sample site 670 near the needle, the appropriate automated process begins when the operator pushes the start button on the user interface 250.

The operator may also operate the system in a "Start Anticoagulation" mode to fill the access needle 660 and attached tubing with anticoagulant prior to initiating the automatic process Each process begins with a filling or priming of the CFC disposable disk by whole blood as described above in connection with the operation of the CFC disk 930. The whole blood is anticoagulated: as blood flows from the donor in tubing that connects the donor to the disposable set 480, anticoagulant is pumped from the manifold and metered into the whole blood at a site below the donor needle. The ratio of anticoagulant flow to donor blood flow is fixed at about 1 to 7, the ratio currently used in manual blood collections. However, this ratio may be optimized at somewhere between 1 to 7 and 1 to 14 for processes that return blood components to the donor.

Once the CFC disk annular separation channel 990 becomes filled with donor blood, steady state operation begins. Blood flows from the donor into the centrifuge at a more or less fixed flow rate. The CFC disk 930 spins as described above, and separation of whole blood into concentrated red cells, plasma, and a buffy coat 1020 occurs continuously, with red cells and plasma are removed at more or less fixed flow rates from the CFC.

An interface between the red cell layer and the plasma forms near the center of the annular separation channel 990. An optical detector 2171 measures the radial location of this interface. This interface position is controlled so as to be maintained at or near the center of the separation channel throughout steady-state continuous-flow operation. This is achieved primarily by providing, in software, for the microprocessor or other controller, to change the flow rate of red blood cell pump 701, by increasing the speed of the appropriate roller pump, to remove greater or fewer red blood cells from the separation channel. Standard feedback control methods can be used.

When the donor hematocrit is much above 40%, the red blood cell flow rate will increase appreciably at a fixed donor blood flow rate. In order to maintain a maximum effective and safe flow rate through the leukofilter 610, the red blood cell flow rate needs to be maintained at or below a maximum value depending upon the leukofilter 610. When it reaches this maximum flow rate, then the donor flow will be increased or decreased, by adjusting the pumping rate, to maintain the red cell-plasma interface 1130 in its desired location. This will increase the donation time for that small percentage of donors who have hematocrits substantially above 40% and who are donating a fixed pre-set volume of whole blood, but will not increase donation time for donors who are donating a fixed volume of red blood cells.

The buffy coat 1020 consists of white cells, including leukocytes, and platelets. It is less dense than red cells and more dense than plasma. Consequently, throughout the steady state continuous-flow separation process, the buffy coat 1020 collects or near the radial center of the separation channel, forming a radially narrow white region at the red cell-plasma interface 1130, between the concentrated red cells at the outermost part of the annular separation channel and the plasma at the innermost part of annular separation channel.

During the purge or component removal part of the process the buffy coat 1020 is either removed to another bag, left in the CFC disk 930, or left in tubing and other components in the disposable set 480. It is not pumped into or through the leukofilter 610 with the concentrated red cells. This removal of buffy coat from the whole blood decreases the amount of leukocytes that must be removed by the leukofilter 610 by a factor of roughly 100. The desired leukocyte count in the concentrated red cells after leukofiltration is $1 \times 10^6$. Buffy coat removal significantly aids leukoreduction and permits a smaller, lower-cost filter having less filter volume and consequently less red cell loss in the filter. Platelet reduction by buffy coat removal is also beneficial. Platelets can form a layer on the leukocyte filter or otherwise plug it, increasing leukofilter pressure drop and resultant hemolysis, or forcing lower flow rates. Reducing this effect by buffy coat removal permits decreased leukofilter size and cost and/or results in lower inlet leukofilter pressures.

Continuously during steady-state operation, the concentrated red cells are pumped out of the CFC disk 930, through a leukofilter 610, and into a red blood cell product bag 640. A storage or additive solution is metered into the packed red blood cell flow stream via a red cell storage solution port 1250 at a rate that achieves the desired concentration of the storage solution. This occurs before the concentrated red cells are pumped through the manifold, and can occur either within the CFC disk 930 as described in connection with the CFC disk 930 operation, or outside it. The storage solution decreases the packed red blood cell hematocrit from about 90% to about 60%. This greatly reduces the viscosity of the packed red blood cells, decreases pressure drops in tubing, and decreases hemolysis that can occur in tubing, other flow passages, the CFC seal assembly or umbilical, and the red cell pump 701. For these reasons it is preferred to add the storage solution 1140 to the packed red blood cells as close as possible to the packed red blood cell pick-up port in the separation channel.

It is also possible to force the concentrated red cells through the leukofilter 610 by increasing the pressure in the CFC disk 930. This has the advantage of eliminating the pumping of the red blood cells and thus reducing the potential for red blood cell damage. However, in the rotating seal design, the increased pressure may compromise the seal, and generally, damage may be reduced to an acceptable level by the addition of storage solution 1140 to the red blood cells before they enter the pump.

The red blood cell pump 701 flow rate is controlled so that the flow through the leukofilter 610 is maintained at or near an optimum. This optimum is a flow high enough that it does not increase donation time or process time appreciably, and low enough to prevent high leukofilter inlet pressures and resultant hemolysis. All concentrated red cells have a storage solution 1140 addition and are pumped through the leukofilter 610 as in the steady state operation.

At the end of the donation, when the selected volume of whole blood or of red blood cells has been taken from the donor, the needle 660 is removed from the donor's vein.

The CFC disk 930 separation channel is now full of separated blood components. One of the purge processes described in connection with the operation of the CFC disk 930 may be used to remove concentrated red cells to the red blood cell product bag 640 and plasma to the plasma bag 630.

Storage solution 1140 may be pumped into the leukofilter 610 to remove red blood cells trapped in the leukofilter 610 and pump them into the red blood cell product bag 640 to minimize red cells lost in the disposable set 480 and maximize overall red cell recovery. The volume of storage solution 1140 used for this purpose is limited by the maximum amount of storage solution 1140 that can be added to a unit of red cells, and by the possible liberation of leukocytes from the leukofilter 610 and carried into the red blood cell product bag 640.

Thus, the red cell product is separated from one or two units of whole blood, packed to a hematocrit of about 90%, has had storage solution added, and has been leukofiltered. The red cells will be in one or two product bags, depending upon the particular process.

Once the purge is completed the product bags are sealed off by the operator and removed from the disposable set 480. The disposable set 480 is then removed from the console 100 and the set is prepared for disposal as a biohazard material.

Many processes can be implemented using the console 100 and cassette model. One such process automatically takes whole blood from the donor, adds anticoagulant, separates the blood into concentrated red cells and plasma in the continuous-flow centrifuge, removes plasma to the plasma product bag, adds a flow of storage solution 1140 to the concentrated red cells, and pumps the red cells through a leukofilter 610 into an red blood cell product bag 640. This processes produces 1 unit of leukoreduced red blood cells in storage solution, and plasma.

Various possible ways of implementing red blood cell and plasma collection are shown in the schematic diagrams of FIGS. 51–54 and described in the State Chart shown in Table 1 and the Operational Summary shown in Table 2. It will be understood that these Figures and Tables are a non-limiting examples of possible processes and that a feature of the invention is that other processes can be performed by selecting and implementing a different series of operations and states.

Figure 51:
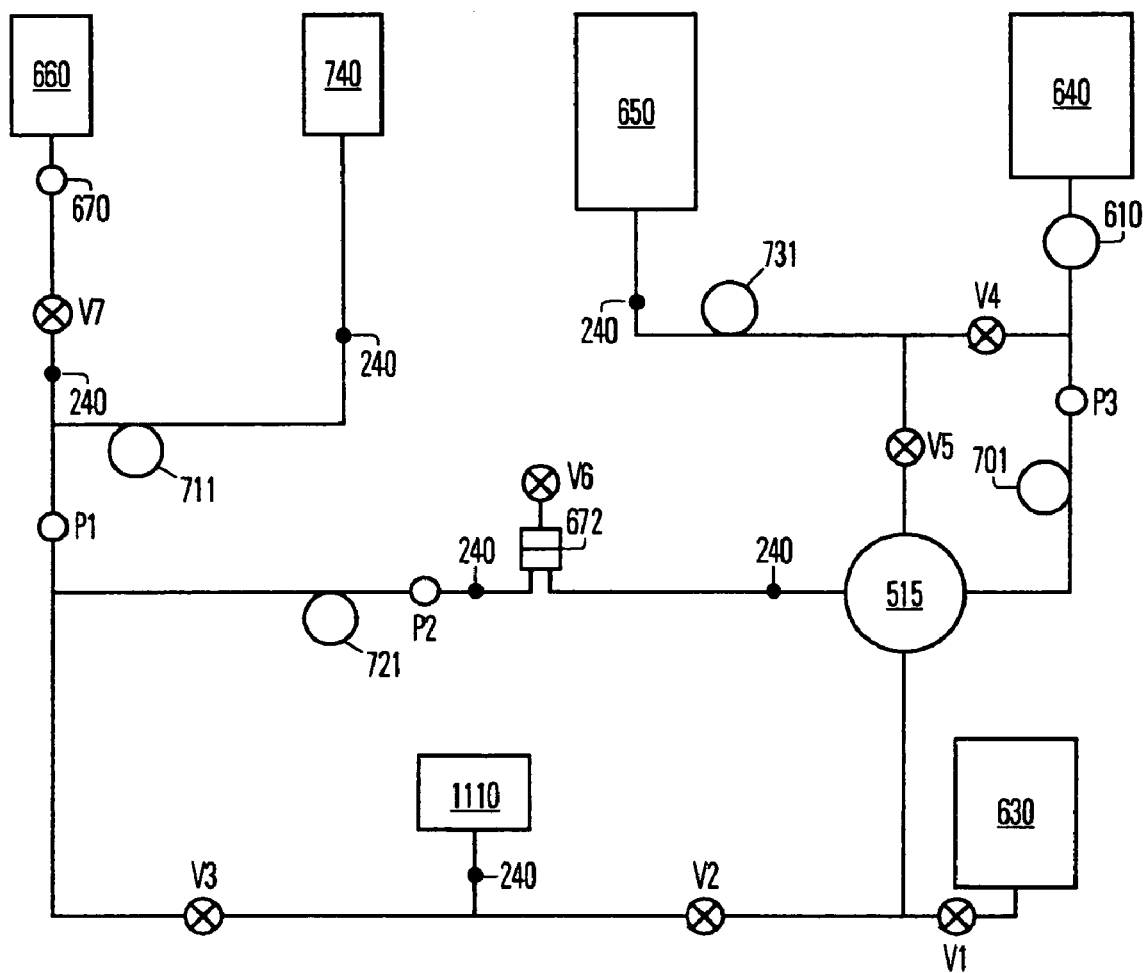
FIG. 51 is a schematic of a first alternative of connections to implement a collection of red blood cells and plasma.

With reference to FIG. 51, this implementation assumes that all plasma, in both the steady state and at the purge, is removed via one line exiting the CFC, as for example, in the CFC disk structure shown in FIG. 45 A and B. The mechanical operation of the various components such as valves, pressure transducers and the like, are as described above in connection with descriptions of the features and interaction of the cassette, console 100 and the CFC disk 930.

The console is able to implement the various steps described by activating and monitoring valve and sensor interface components on the cassette. For some of the processes described below, the connections to the tubing receptacles on the manifold 510 may be made as follows: receptacle 950 is connected to the red blood cell outlet 1033 of the centrifuge 515; the top of the bubble trap 672 is connected to receptacle 949; the storage solution bag 650 is connected to receptacle 947; a second red blood cell bag 640, if needed in the process, which also includes a leukofilter 610 is connected to receptacle 946; if a second red blood cell bag is used, the first red blood cell bag 640 is connected at 944 and a connection is made between receptacles 943 and 945, otherwise the single red blood cell bag is connected at 943; receptacle 942 is connected to the storage solution input 1032 of the centrifuge 515; the anticoagulant line intended for the needle is attached at receptacle 941; the needle line, supplying whole blood to the system is connected to receptacle 939; either a saline bag or an air bag, depending on the process, may be connected to the receptacle at 938; the plasma bag is connected at receptacle 936; the line connecting whole blood and a bubble trap, which is positioned on the cassette so as to allow it to be read by the ultrasonic sensor, is attached at receptacle 935; and the anticoagulant bag is connected at 934. Persons of ordinary skill in the art will appreciate that different connections to the manifold could be made to implement different processes.

TABLE 1

| step # | STATE TITLE | SYSTEM ACTIONS | OPERATOR ACTIONS | MODE | CFC RATE | VALVES OPEN | PUMPS ON |
|---|---|---|---|---|---|---|---|
| 1 | Initializing | | plug in system and switch on system | WAIT | | | |
| 2 | Self Check | system boot up and system internal checks (pumps, valves, etc. function) | unpack disposable, | WAIT | | | |
| 3 | System "Disposable Ready" | Display: "ready to accept disposable, is needle damped" | | WAIT | | | |
| | | | install disposable, hang preattached bags, and damp needle line, press continue button | WAIT | | | |
| 4 | Disposable, and more Self Checks | determine disposable type installed, check disposable installed correctly, check disposable integrity, and more internal system checks(pfs), | | NEXT | | | |
| 5 | Protocol confirmation | Display: "disposable type is . . . " | | WAIT | | | |
| | | | check that disposable recognized matches protocol to be performed, press continue button | WAIT | | | |
| 6 | Prep disposable | zero transducers, spin cfc slow to bed in cfc seal, evacuate system to assure air trap diaphragm positioned for blood | spike or luer attach and hang solution bags | ZERO | 500 | 6, 8 | bp and rp backwards |
| 7 | Confirmation of solutions attached | Display "ready to prime system are solution bags attached" | | WAIT | | | |
| | | | press continue button | WAIT | | | |

TABLE 1-continued

| step # | STATE TITLE | SYSTEM ACTIONS | OPERATOR ACTIONS | MODE | CFC RATE | VALVES OPEN | PUMPS ON |
|---|---|---|---|---|---|---|---|
| 8 | Prime cpda to needle | prime cpds to needle wye, continue seal bed | | NEXT | 500 | 6 | ac |
| 9 | Prime storage solution line | prime storage solution line from ss bag to p3, continue seal bed | prepare donor | NEXT | 500 | | sp |
| 10 | Home CFC | slow cfc to stop, rotate cfc to home position | | JOG | clock | | |
| 11 | Confirmation of system ready for a donor | Display "ready for a donor" | prepare donor and phlebotomize | WAIT | | | |
| | | | unclamp needle line and draw volume of blood into sample bag | WAIT | | | |
| | | | clamp sample bag and or metal clip closed, take vacutainer samples from sample bag | WAIT | | | |
| | | | press continue button to start draw | WAIT | | | |
| 12 | Start donation, blood prime systems | draw blood (60 ml/min max) from donor filling time and bubble trap (anticoagulant metered) | | PFIL | | 8 | bp, ac |
| 13 | Continue prime line | continue drawing blood to US1 setting up cfc fill | | LIQD | | 2 | bp, ac |
| 14 | Zero donor line | pause to check zero at donor lone PT1 | | ZERO | | 2 | |
| 15 | Prime cfc | clock fill cfc with whole blood (all air is purged to air bag) | | JOG | clock | 2 | bp, ac |
| 16 | Spin cfc to rate 4000 | slow donation draw down to match slow draw of rbc (approx 15 ml/min) while cfc is spun up to 4000 rpm and separation occurs (approx 10 sec.) | | | 4000 | | bp, ac, rp, sp |
| 17 | Separation/prime LF | increase donor draw rate (max to limit 30 ml/min leukofilter prime rate) prime leukofilter with blood, (storage solution flow is metered to rbc flow into leukofilter), simultaneously draw plasma | | PFIL | 4000 | 1 | bp, ac, rp, sp |
| 18 | Separation | draw at rates acceptable to donor pressure and leukofilter max flow | | PFIL | 4000 | 1 | bp, ac, rp, sp |
| 19 | Donation ends | donor draw volume reached, system stops donor blood draw and anticoagulant feed and rbc/ss pumps, displays end values, and alarms operator that donation stage is complete | | WAIT | 4000 | | |
| | | | acknowledge alarm | WAIT | 4000 | | |
| 20 | Confirmation donor is off line | display: "Is line clamped and needle removed???" | clamp needle line and remove needle, apply needle protector, sterile gauze to donor | WAIT | 4000 | | |
| | | | press continue button | WAIT | 4000 | | |
| 21 | Purge donor line with anticoagulant | purge whole blood line to p1 with anticoagulant, slow draw rbc with plasma valve open | attend to donor | SCAN | 4000 | 1 | ac, rp, sp |
| 22 | Purge donor line, air | purge whole blood line to cfc with air from air bag, slow draw rbc with plasma valve open | | | 4000 | 1, 6 | rp, sp |
| 23 | Purge rbc from cfc | draw rbc from cfc slowly allowing plasma to return from plasma bag | | | 4000 | 1 | rp, sp |
| 24 | Spin down cfc | slow cfc to stop | | NEXT | decel | | |
| 25 | Position plasma port | home and clock cfc to plasma port | | HOME | clock | | |
| 26 | Purge plasma from cfc | rotate cfc and pump air with bp from air bag purging plasma to bag | | JOG | clock | 1, 6 | bp |
| 27 | Purge plasma from line | pump air with bp from air bag | | JOG | clock | 1, 6 | bp |
| 28 | Position rbc port | clock cfc to rbc port | | JOG | clock | | |
| 29 | Purge rbc line | pump remaining rbc to purge line to leuko | | JOG | clock | 2 | rp, sp |
| 30 | Purge leuko | pump in remaining storage solution to purge leuko filter | | NEXT | | | sp |
| 31 | Air out rbc | display: "Invert RBC Product bag, mix and purge air" | | NEXT | | | |
| | | | invert RBC bag and mix, press and hold remove air button until air is to mark in tube segment Ene, seal tube at mark, and press continue | | | 2 | rp backwards |

TABLE 1-continued

| step # | STATE TITLE | SYSTEM ACTIONS | OPERATOR ACTIONS | MODE | CFC RATE | VALVES OPEN | PUMPS ON |
|---|---|---|---|---|---|---|---|
| 32 | Air out plasma | display: "Invert Plasma Product bag and purge air" | invert Plasma bag, press and hold remove air button until air is out, seal tube to bag and press continue | | | 1, 6 | bp backwards |
| 33 | Process Complete | display: "process complete, press start to initiate next process" | | | | | |

TABLE 2

63 ml/min blood to cfc
40 ml/min rbc/ss to leukofilter

| | | | | valve state | dir | speeds rpm cfc | ml/min rbc | ml/min wb | ml/min ac | ml/min as | ml count | time/step seconds | | |
|---|---|---|---|---|---|---|---|---|---|---|---|---|---|---|
| 1 | "WBCEC 020602A" | 0:00:02 | WAIT | 1111111101 | 0 | 0 | 0 | 0 | 0 | 0 | | | | |
| 2 | "Zero Transducers" | 0:00:02 | ZERO | 1111111101 | 0 | 0 | 0 | 0 | 0 | 0 | | 2 | | |
| 3 | "EPH ON" | 0:00:01 | DCN | 10001 | 10000 | 0 | 0 | 0 | 0 | 0 | | 1 | | |
| 4 | "Run CFC" | 0:00:01 | NEXT | 10001 | 10000 | 15 | 0 | 0 | 0 | 0 | | 1 | | |
| 5 | "Bed Seal/ Evacuat" | 0:00:15 | NEXT | 10010001 | 10100 | 0 | 0 | 160 | 0 | 0 | | 15 | | |
| 6 | "Home" | 0:00:05 | HOME | 1 | 0 | 30 | 0 | 0 | 0 | 0 | | 5 | | |
| 7 | "Check goal" | 0:00:01 | WAIT | 1 | 0 | 0 | 0 | 0 | 0 | 0 | | | | |
| 8 | "Reset B used" | 0:00:01 | RSET | 1 | 0 | 0 | 0 | 0 | 0 | 0 | | 1 | | |
| 9 | "Jog/Valves Off" | 0:00:10 | JOG | 1 | 0 | 4 | 0 | 0 | 0 | 0 | | 10 | | |
| 10 | "Prime SS line" | 0:20:00 | LIQD | 1 | 0 | 0 | 0 | 0 | 0 | 20 | 25 | | calc | 36" line |
| 11 | "Prime SS line" | 0:00:05 | NEXT | 1 | 0 | 0 | 0 | 0 | 0 | 20 | | 3 | | |
| 12 | "UNCAP NEEDLE" | 0:00:01 | WAIT | 1 | 0 | 0 | 0 | 0 | 0 | 0 | | | | |
| 13 | "Prime line" | 0:20:00 | LIQD | 101000001 | 0 | 0 | 0 | 70 | 0 | 0 | | 13 | calc | 72" line |
| 14 | "Prime air trap" | 0:20:00 | PFIL | 1010001 | 0 | 0 | 0 | 70 | 0 | 0 | 20 | 18 | | |
| 15 | "Prime CFC WB" | 0:00:00 | NEXT | 101000001 | 0 | 0 | 0 | 70 | 0 | 0 | 10 | 0 | | |
| 16 | "ROTATE 435" | 0:01:08 | JOG | 101000001 | 0 | 2 | 0 | 65 | 0 | 0 | | 68 | calc | |
| 17 | "CONTINUE FILL" | 0:00:15 | CONC | 101000001 | 0 | 0 | 0 | 65 | 0 | 40 | | 0 | | |
| 18 | "Pull air rbc" | 0:00:03 | NEXT | 1000001 | 10000 | 0 | 70 | 70 | 0 | 0 | | 3 | | |
| 19 | "Pumps Off" | 0:00:02 | NEXT | 1000001 | 0 | 0 | 0 | 0 | 0 | 0 | | 2 | | |
| 20 | "ROTATE 360" | 0:00:30 | JOG | 1000001 | 0 | 4 | 0 | 0 | 0 | 0 | | 30 | | |
| 21 | "Spin slow draw" | 0:20:00 | PFIL | 101000001 | 1000 | 350 | 15 | 15 | 0 | 0 | 5 | 20 | calc | |
| 22 | "Spin recirculate" | 0:20:00 | PFIL | 101000001 | 1000 | 350 | 20 | 31 | 0 | 6 | 50 | 97 | calc | |
| 23 | "Drain Air Bag" | 0:20:00 | SCN2 | 1011000001 | 1000 | 350 | 40 | 63 | 0 | 12 | | 60 | calc | 30 ml? |
| 24 | "Separate" | 0:20:00 | PFIL | 1001000001 | 1000 | 350 | 40 | 63 | 0 | 12 | 1 | 1 | | |
| 25 | "Separate" | 0:20:00 | SPIL | 1001000001 | 1000 | 350 | 40 | 63 | 0 | 12 | 351 | 334 | calc | |
| 26 | "Pumps Off" | 0:00:02 | NEXT | 1001000001 | 0 | 350 | 0 | 0 | 0 | 0 | | 2 | | |
| 27 | "Valves Off" | 0:00:01 | NEXT | 0 | 0 | 350 | 0 | 0 | 0 | 0 | | 1 | | |
| 28 | "Purge air to US1" | 0:20:00 | MOVE | 1010000001 | 1000 | 350 | 40 | 63 | 0 | 12 | | 24 | calc | |
| 29 | "Purge air to CFC" | 0:00:00 | NEXT | 1010000001 | 1000 | 350 | 40 | 63 | 0 | 12 | | 0 | | |
| 30 | "Pumps Off" | 0:00:02 | RSET | 1010000001 | 0 | 0 | 0 | 0 | 0 | 0 | | 2 | | |
| 31 | "Valves Off" | 0:00:02 | NEXT | 100000000 | 0 | 0 | 0 | 0 | 0 | 0 | | 2 | | |
| 32 | "Spn dwn/ Pumps Off" | 0:00:25 | NEXT | 100000001 | 0 | 0 | 0 | 0 | 0 | 0 | | 25 | | |
| 33 | "Home/ Valves Off" | 0:00:05 | HOME | 1 | 0 | 30 | 0 | 0 | 0 | 0 | | 5 | | |

TABLE 2-continued 63 ml/min blood to cfc
40 ml/min rbc/ss to leukofilter

| | | | valve state | dir | speeds rpm cfc | ml/min rbc | ml/min wb | ml/min ac | ml/min as | ml count | time/step seconds |
|---|---|---|---|---|---|---|---|---|---|---|---|
| 34 | "Jog/Valves Off" | 0:00:10 | JOG | 1 | 0 | 4 | 0 | 0 | 0 | 0 | 10 |
| 35 | "Purge CFC - RBC" | 0:01:50 | NEXT | 110000001 | 1000 | 0 | 60 | 30 | 0 | 0 | 110 |
| 36 | "Purge Plasma Line" | 0:00:15 | NEXT | 1010000001 | 10 | 0 | 0 | 60 | 0 | 0 | 15 |
| 37 | "Home/ Vavles Off" | 0:00:05 | HOME | 1 | 0 | 30 | 0 | 0 | 0 | 0 | 5 |
| 38 | "PROCESS COMPLETE" | 0:00:01 | END | 1 | 0 | 0 | 0 | 0 | 0 | 0 | 1 |
| | | | | | | | | | | sum of time | 911 seconds |
| | | | | | | | | | | sum of time | 15.2 minutes |

In operation, after the cassette 490 is placed in the console 100, the console 100 is activated so as to begin the process. The operator selects a whole blood or red blood cell volume to be collected from the donor. Valves v1, v3 and v6 are initially closed, valves v2, v4, v5 and v7 are open. Anticoagulant is pumped to the needle 660 to purge air and ensure correct anticoagulation of first amount of blood pumped from donor. Red cell solution is pumped to the red cell storage solution port 1250 in the CFC disk and to the entrance of the leukofilter 610. Valves v1, v6 and v3 opened to evacuate disposable air to the air bag 1110 and evacuate the bubble trap 672 so as to position the bubble trap 672 diaphragm as is conventionally required. Valve v3 is closed. The donor venous needle 660 access is made by the operator in standard fashion, the manual clamp 661 is released, and blood is pumped from the donor using the whole blood pump 721 at rates determined by donor venous pressure that may be determined using pressure transducers 200, 193. Anticoagulant continues to be pumped into the blood using the anticoagulant pump 711 downstream of the needle 660 and a blood sample site. The ratio of anticoagulant flow to blood flow is fixed. As blood is pumped initially from the donor it fills the bubble trap 672 and begins to prime the centrifuge disk separation channel 990 which may be implemented as described above in connection with the operation of the centrifuge disk. The CFC disk 930 is rotated to ensure all air is removed and that blood completely fills the disk channel and passages. Air is displaced into the air bag 1110 for later use and priming continues until whole blood enters the air bag. When the disk separation channel 990 is filled with whole blood, valve v2 is closed. The CFC disk speed is increased to its operating speed, generally at around 4000 rpms. The red blood cell plasma interface is established and steady-state continuous-flow separation into concentrated red cells and plasma begins. Plasma flows to the closed valve v2, cleaning the plasma line. Red cells are pumped out of the CFC disk 930 by the red blood cell pump 701 at a rate determined by the whole blood flow rate and by the optically-measured red cell interface location as determined by the optical detector 2171. The red cell flow rate is adjusted to keep the red cell interface in the desired, optimal location in the separation channel. Valve one is opened. Plasma flows out into the plasma product bag, which may be weighed on an electronic scale 671. When red cells flow out of the disk they are mixed with storage or additive solution in the CFC disk as described in connection with the CFC disk design above, and/or outside of the CFC disk 930 from the red cell storage solution bag 650. This solution is pumped by the storage solution pump at a flow rate that achieves the fixed, desired ratio of additive solution flow to red cell flow. The combined flow goes through a red cell leukofilter 610 into the red cell product bag 640. The continuous-flow process continues until the end of the donation. The calibrated whole blood pump stops when the selected volume of whole blood or red blood cells has been collected. The donor line 620 at the needle 660 is clamped off using the manual clamp 661 and the needle 660 is removed from the donor. The anticoagulant continues to be pumped for a time so as to purge the donor blood line 620 with anticoagulant to maximize red cell and plasma recovery. The speed of the disk is increased to 5000 rpms. The purge process now begins. Valve three v3 is opened and blood from the air bag 1110 is drawn into the CFC. The red blood cell pump 701 is controlled so as to increase the red blood cells in the separation channel while plasma continues to be removed from the disk. Air is now drawn from the air bag 1110 into the bubble trap 672 as the last of the plasma is purged from the separation channel. Valve v1 may be closed. The rotation is stopped and the red blood cell port is clocked to a position at the bottom of the disk. Air is pumped into the disk using the blood pump 721 to purge the red blood cells from the separation channel. Valve five may be closed. After all blood is removed from the separation channel, valve one may be opened to purge plasma from the plasma line. The leukofilter 610 is purged with storage solution, and the automated process is compete.

The red cell and plasma product bags are heat-sealed off and the rest of the disposable set 480 is removed and prepared by the operator for disposal as a biohazard.

Figure 52:
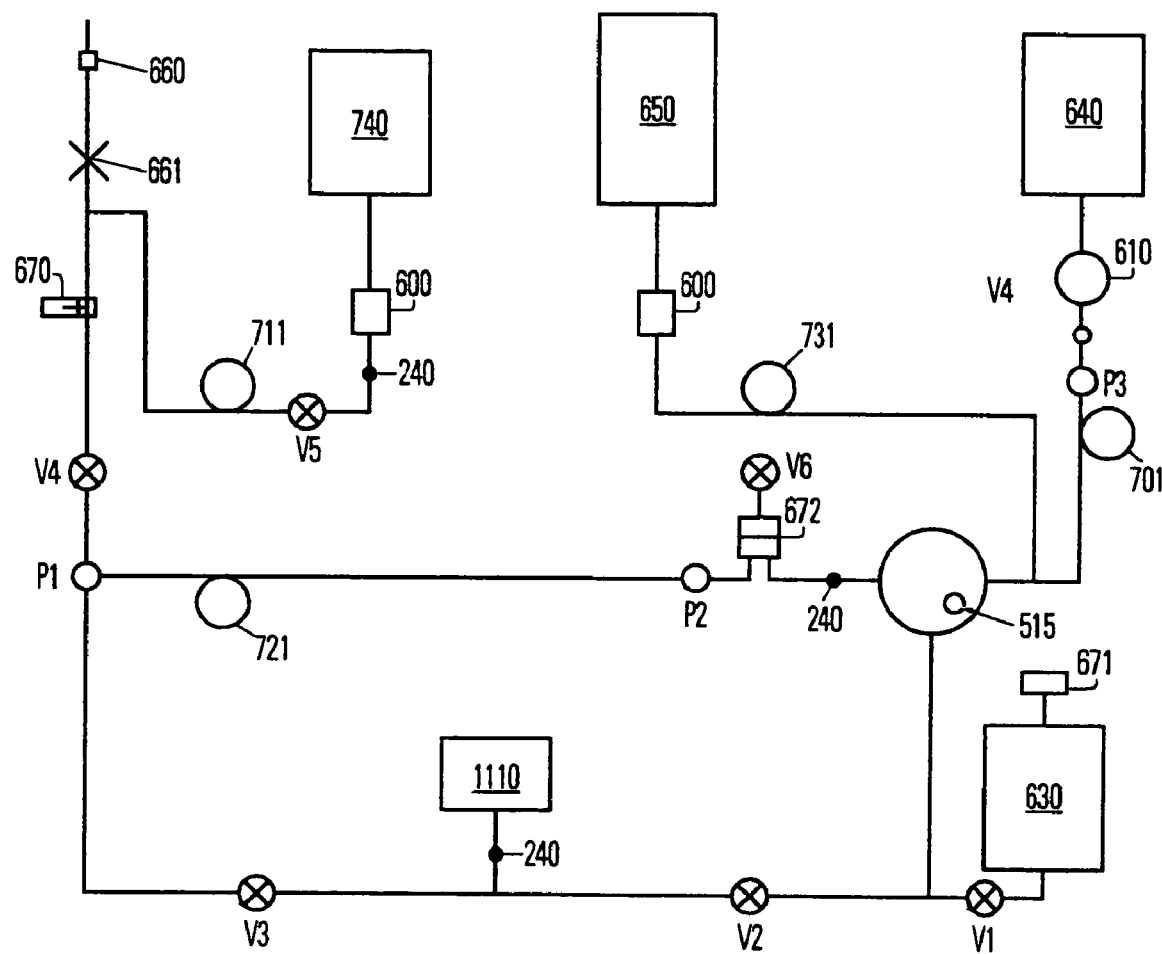
FIG. 52 is a schematic of a second alternative of connections to implement a collection of red blood cells and plasma.
Figure 53:
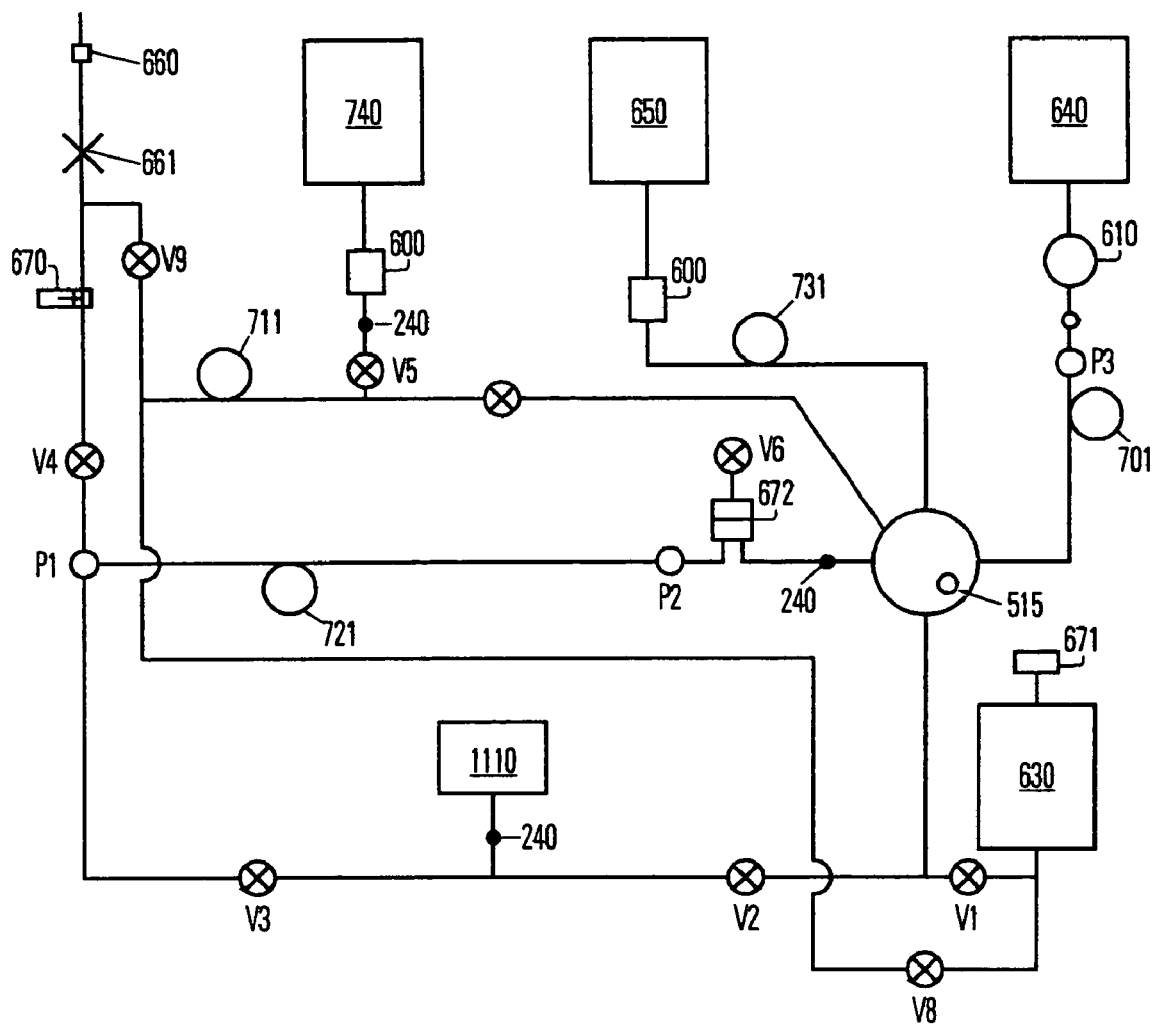
FIG. 53 is a schematic of a third alternative of connections to implement a collection of red blood cells and plasma.
Figure 54:
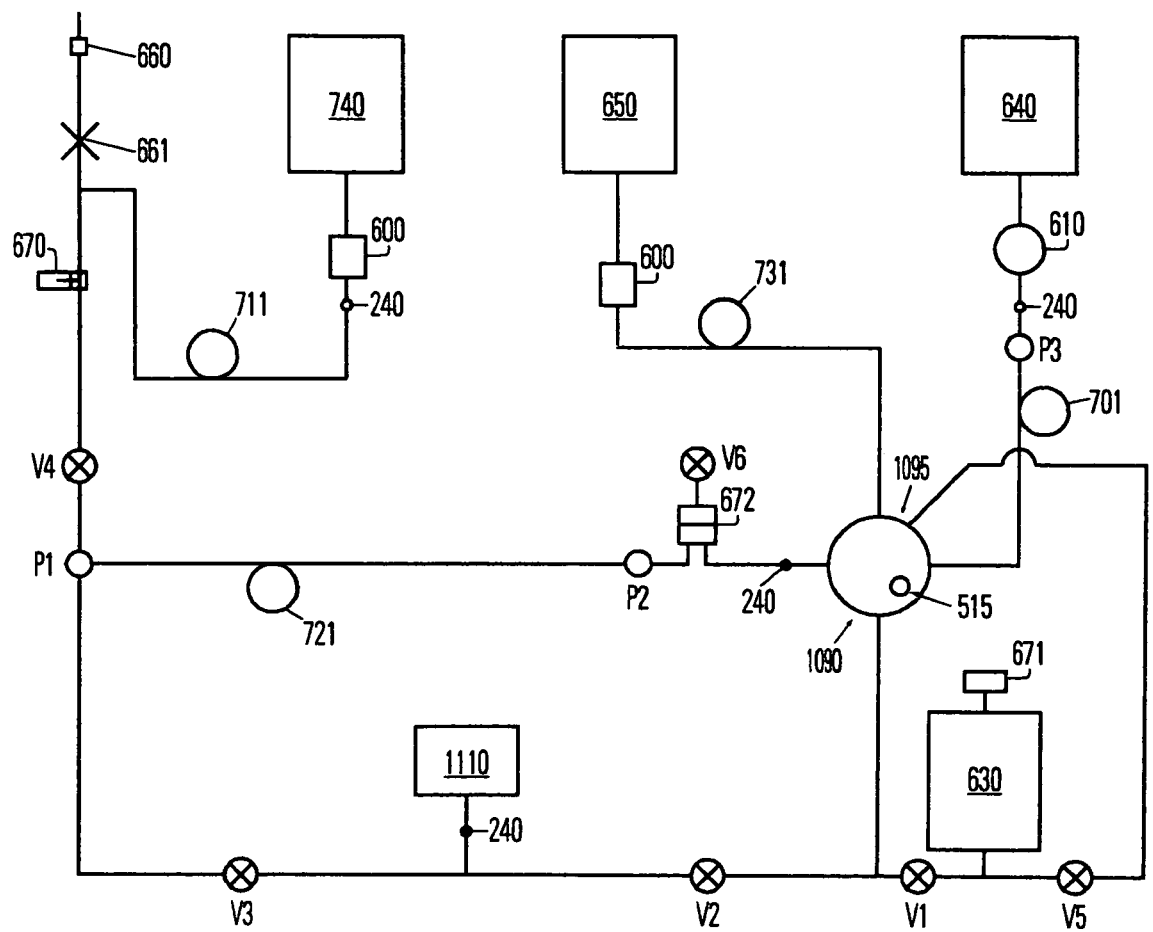
FIG. 54 is a schematic of a fourth alternative of connections to implement a collection of red blood cells and plasma.

With reference to FIGS. 52–54, the structure and processes are similar to that described in detail in the discussion relating to FIG. 51. There are differences: for example, in the process as shown by FIG. 52, storage solution is added externally to the CFC disk, and there is no direct connection of storage solution to a point near the leukofilter 610. In FIG. 54 there are two plasma lines, one removing plasma during steady state, similar to that shown in FIG. 51, and one, connected to a second plasma removal port 1095, for removing plasma during purge using the anticoagulant pump 711.

Additionally, the storage solution pump 731 pumps the storage solution to be added internally to the CFC disk 930 rather than adding the storage solution between the CFC disk 930 and the red blood cell pump 701. Also, there is no valve between the anticoagulant bag 740 and the anticoagulant pump 711, and an additional second line, with valve v5 is connected between a second plasma removal port 1095 and the plasma bag 630. During the purge process, air is pumped by the blood pump 721, under pressure, into the disk separation channel 990 and forces the plasma out to the plasma bag 630 through the second plasma port.

Figure 55:
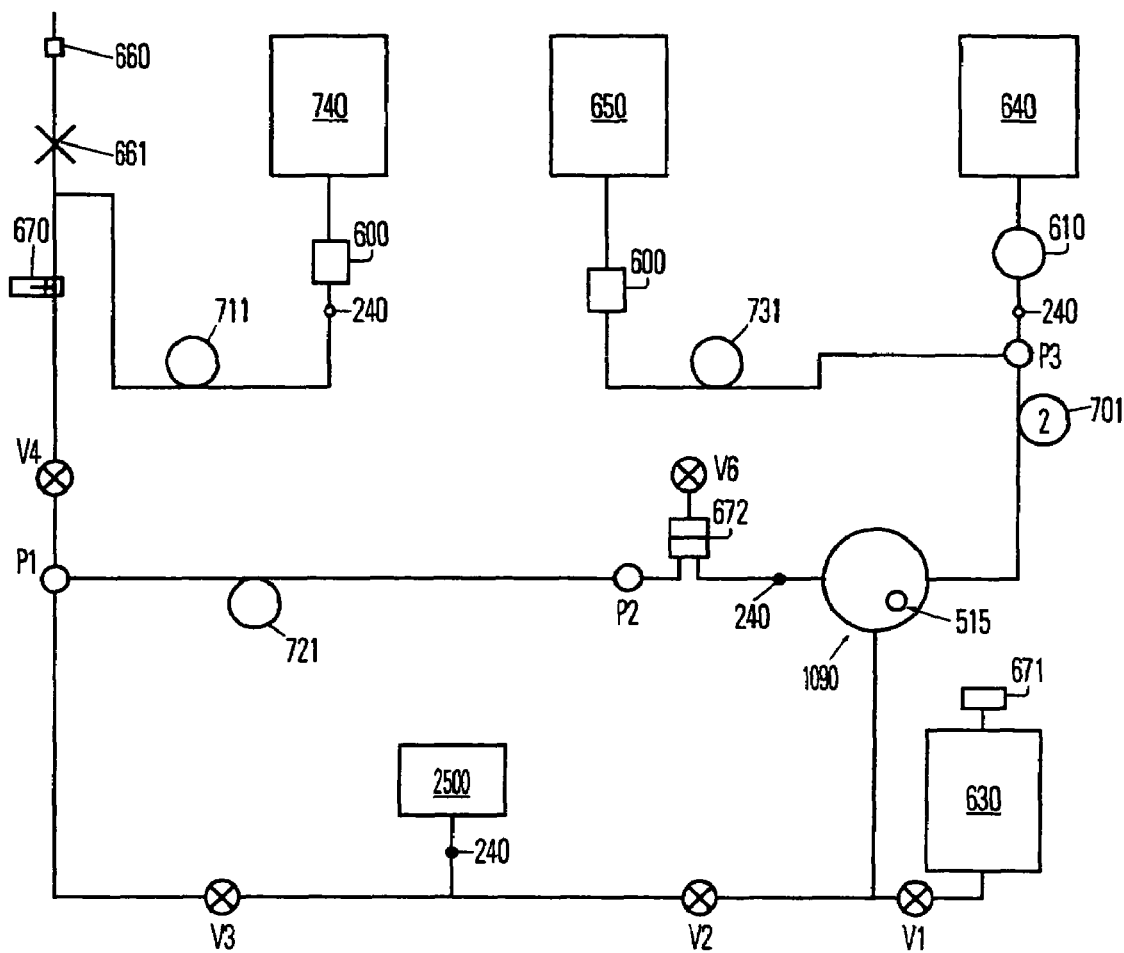
FIG. 55 is a schematic of a first alternative of connections to implement a collection of red blood cells, plasma, and buffy coat.

The process shown in FIG. 55 is similar in intent to that shown in FIG. 51, except that the buffy coat 1020 is now removed to a product bag 2500 which replaces the air bag. In addition, the storage solution pump 731 is connected above the red blood cell pump 701. In will be noted that the three possible connections of the storage solution pump: to the CFC disk 930, below the red blood cell pump 701 and above the red blood cell pump 701 represent options that could be implemented with any of the designs shown.

The buffy coat, a mixture of leukocytes and platelets, develops at the red cell-plasma interface 1130 in the CFC. It collects within the disk separation channel 990 throughout the donation and separation process. In other processes, the buffy coat may remain in the centrifuge and red blood cell outlet tubing at the end of the red blood cell removal. In the current design, the buffy coat is transferred into a platelet product bag 2500 via the plasma removal port 1090 and tubing after plasma has been removed to the plasma bag 630 by opening valve 2 and operating the whole blood pump 721 as in the purge process.

Figure 56:
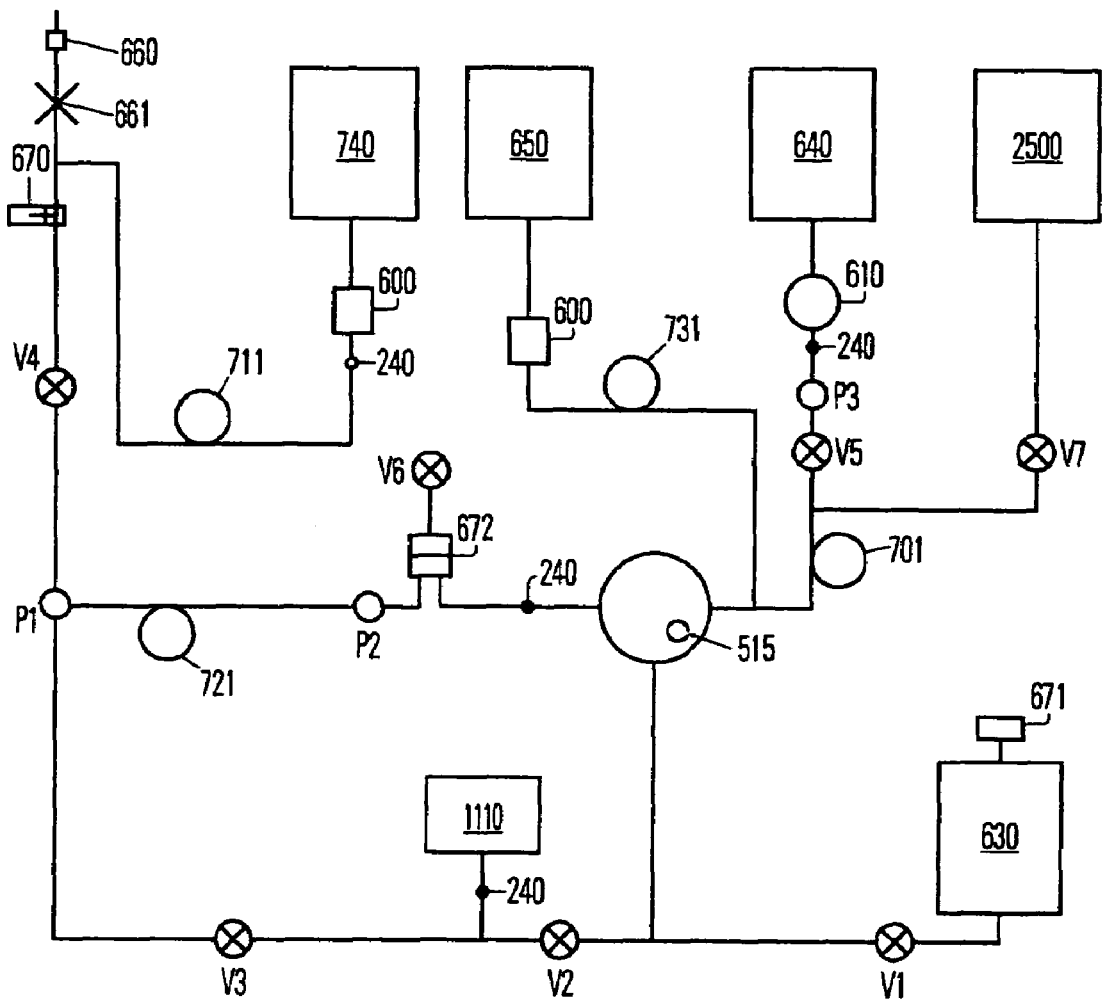
FIG. 56 is a schematic of a second alternative of connections to implement a collection of red blood cells, plasma and buffy coat.

Alternatively, as shown in FIG. 56, the buffy coat bag 2500 is connected between the red blood cell bag 640 and the red blood cell pump 701 with access controlled by valve v7. The buffy coat is pumped out of the CFC separation channel 990 to the buffy coat bag via the red blood cell port and tubing, using the red blood cell pump 701, after the red blood cells have been removed from this channel and pumped into the red blood cell bag 640 by opening valve v7 and closing valve v5.

Figure 57:
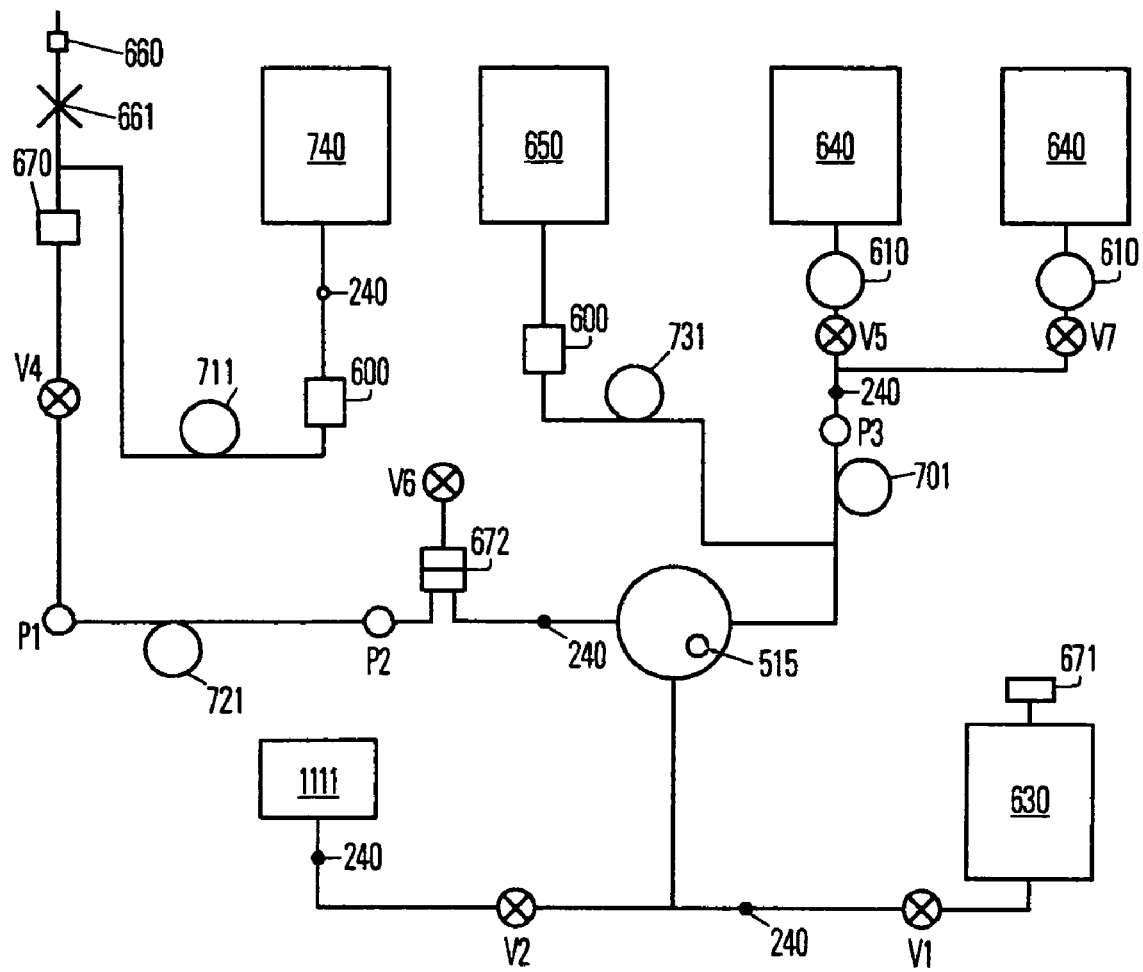
FIG. 57 is a schematic of connections to implement a collection of two units of red blood cells.

The process shown in FIG. 57 is intended to collect two units of whole blood from a donor. Each unit of whole blood is anticoagulated, separated, storage solution is added to the concentrated red cells, and these cells are pumped through a leukofilter 610 into a red blood cell product bag 640.

Essentially the process shown in FIG. 52 is performed twice in series. However, a saline bag 1111 is connected in place of the air bag and there is no connection between the saline bag 1111 and valve v3. Additionally, a second red blood cell bag 640 is connected, with a controlling valve v7, above the red blood cell pump 701. Near the end of each process during the purge of the CFC separation channel 990, red blood cells are pumped out first into the red blood cell bag while plasma flows back into the channel. After the valves controlling the red blood cell bags are closed, the plasma is pumped out of this channel by the whole blood pump 721 into the donor. When the plasma bag 630 is empty, as detected by the ultrasonic detector, saline flows into the separation channel 990 and is pumped into the donor. The saline volume pumped into the donor equals the packed red blood cell volume so that the net blood volume change for the donor is zero. In this process air is not used to purge the continuous flow centrifuge. The CFC disk rotation can be slowed or stopped during the flow of plasma and saline to the donor. At the end of the first process, after plasma and saline volumes are pumped to the donor, the separation channel 990 is filled with saline. Then in the second process valve v2 is closed and this saline is removed to the plasma bag 630 as whole blood enters and fills the CFC separation channel 990.

Near the end of this second process both the plasma and saline collected in the plasma bag 630 are returned to the donor in the same manner as plasma was returned to the donor at the end of the first process. The amount of plasma collected is determined by the microprocessor by subtracting the red blood cell pump 701 pumped volume and the anticoagulant pump 711 pumped volume from the whole blood pump pumped volume. Then the amount of saline to be pumped from the plasma bag 630 can be determined as well as the amount of additional saline to be returned. The total amount of saline to be pumped to the donor is equal to the red blood cell pump 701 pumped volume minus the solution pump pumped volume.

Figure 58:
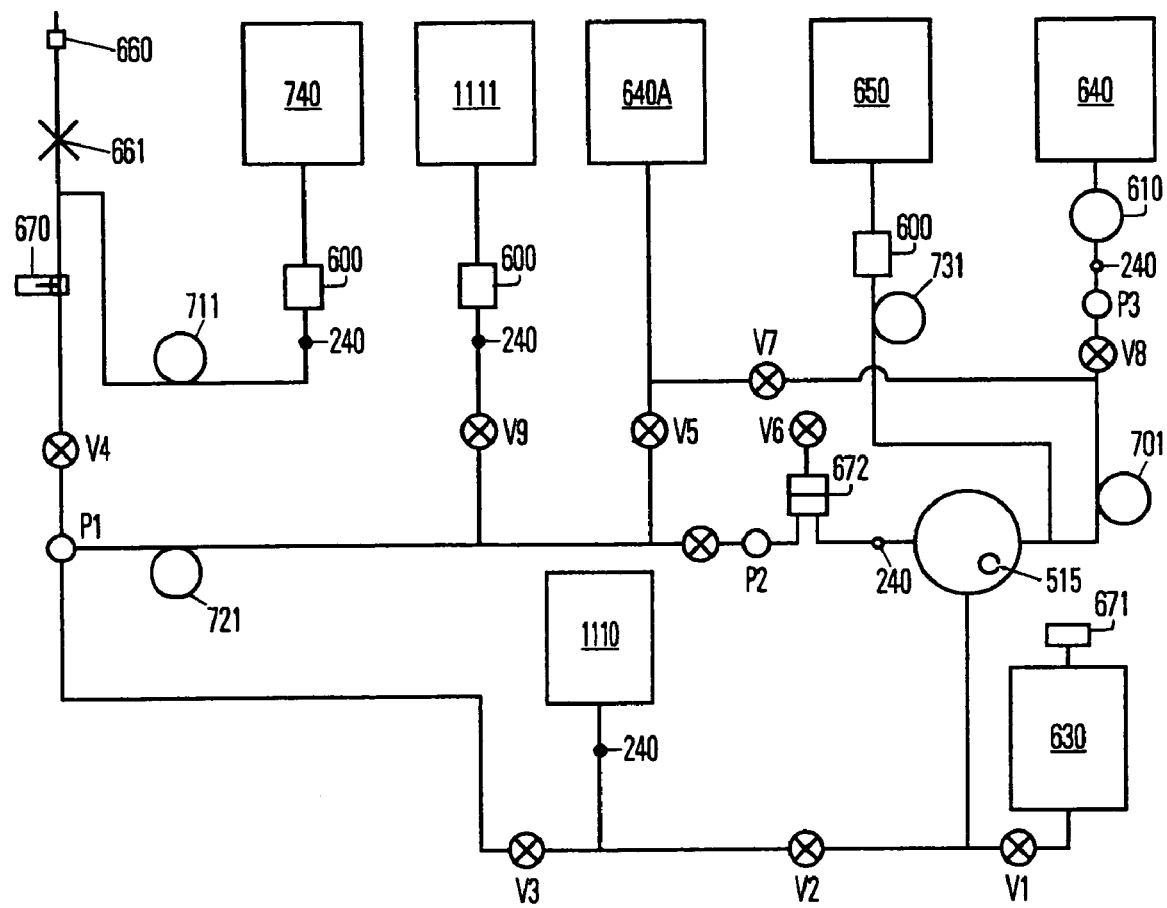
FIG. 58 is a schematic of connections to implement a collection of red blood cells and jumbo plasma products.

The process shown in FIG. 58 is intended to collect two units of whole blood from a donor. As with the processes described above, as will be evident to those of ordinary skill in the art, the movement of the various fluids and products will be implemented by the microprocessor utilizing appropriate software for control of the pumps and valves, in response to inputs from the various monitors. The two units of whole blood are processed to collect as products one unit of red cells and two units of plasma. One unit of whole blood is collected and processed initially as in the process of FIG. 39. The red cells in this first process are collected in a red blood cell temporary storage bag 640A. These red blood cells have storage solution added but are not leukofiltered. At the end of purge, the blood pump 721 pumps the red cells into the donor. The CFC separation channel 990 is filled with plasma. Then a quantity of saline is pumped by the blood pump 721 into the donor. This quantity equals the volume of plasma removed from the donor, minus the volume of storage solution added to the red cells. Then the net volume removed from the donor at the end of this first process is zero. A second unit of whole blood is collected and processed as in the process shown in FIG. 57. The whole blood enters the spinning CFC, displacing the plasma that has filled the separation channel 990 into the plasma bag 630. The whole blood separates into red cells and plasma, so red cells do not contaminate the plasma that filled the channel. Red cells are pumped, after storage solution addition, through the leukofilter 610 and into the red blood cell product bag 640. Plasma flows into the plasma bag 630. A purge of the separation channel 990 occurs. Saline may be pumped into the donor in an amount equal to whole blood removed from the donor; this may not be necessary since the volume lost by the donor would generally be acceptable.

Figure 59:
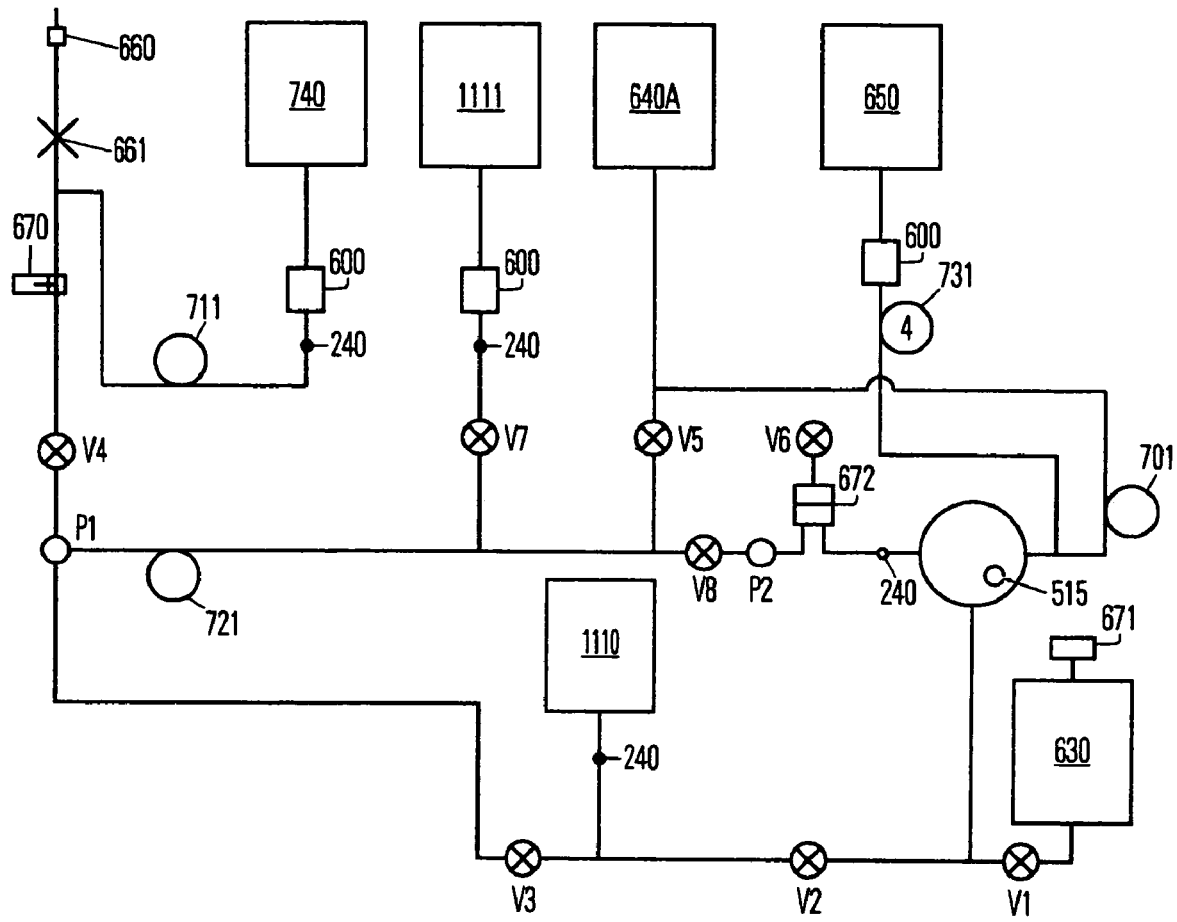
FIG. 59 is a schematic of connections to implement a collection of a plasma product.

Another process is described with reference to FIG. 59. As with the processes described above, as will be evident to those of ordinary skill in the art, the movement of the various fluids and products will be implemented by the microprocessor utilizing appropriate software for control of the pumps and valves, in response to inputs from the various monitors. This process is intended to collect multiple units of whole blood from a donor. These units of blood are processed to collect plasma only, returning red cells and buffy coat to the donor.

Each unit of blood is collected initially as in the process described in connection with FIG. 39. Red cells are pumped to a red blood cell temporary storage bag. Saline is added to the red cells before the red blood cell pump 701. Saline volume added is equal to the plasma volume removed to the plasma bag 630. In the purge process, red cells from the red blood cell temporary storage bag are pumped into the donor using the blood pump 721. The plasma remains in the CFC separation channel 990 and is displaced by the next unit of whole blood into the plasma bag 630. The final purge of plasma at the end of the process is performed with air entering the separation channel 990 and displacing the remaining plasma into the plasma bag 630. Although air is most convenient since it can be collected during the priming process, it would also be possible to use another gas. This process results in no net volume lost by the donor and no red cell, platelet, or white cell loss.

It will be evident that other processes, including processes that do not involve the connection of a donor to the cassette 490, could be implemented using the basic console and cassette design. For example, using appropriate cassette components and software it would be possible to prepare a therapeutic dose of leukoreduced platelets from pooled buffy coats using the console.

While preferred embodiments of the present invention are described above and in the following claims, it is contemplated that various modifications may be made without departing from the spirit and scope of the invention.

What is claimed is:

1. A method of simultaneous blood collection and separation using a continuous flow centrifuge having a separation channel, a blood input port, a concentrated red blood cell output port, a first plasma output port, and a second plasma output port, comprising the steps of:
    collecting blood from a donor to form a blood flow;
    simultaneously with the collecting step adding an anticoagulant to the blood flow to form an anticoagulated blood flow;
    simultaneously with the adding step, introducing the anticoagulated blood flow into the separation channel through the blood input port while keeping the blood input port open;
    simultaneously with the introducing step, operating the centrifuge to produce a flow of concentrated red blood cells and a flow of plasma from the anticoagulated blood flow;
    simultaneously with the operating step, directing the flow of plasma from the separation channel through the first plasma output port into a plasma collection bag while keeping the first plasma output port open;
    simultaneously with the operating step, directing the flow of concentrated red blood cells from the separation channel through the red blood cell output port into a fluid transportation means while keeping the red blood cell output port open;
    simultaneously with the operating step, introducing red cell storage solution into the flow of concentrated red blood cells in the fluid transportation means;
    simultaneously with the operating step, directing the flow of concentrated red blood cells from the fluid transportation means into a red blood cell collection bag;
    keeping the second plasma output port closed while the first plasma output port is open;
    at the occurrence of a preselected event, closing the blood input port to prevent the anticoagulated blood flow from entering the separation channel;
    after the closing step, directing the flow of plasma from the plasma collection bag into the separation channel;
    simultaneously with the step of directing the flow of plasma into the separation channel, continuing operation of the centrifuge to produce a flow of concentrated red blood cells;
    simultaneously with the continuing operation step, directing the flow of concentrated red blood cells from the separation channel into a fluid transportation means while keeping the concentrated red blood cell output port open;
    simultaneously with the continuing operation step, monitoring the amount of plasma in the separation channel;
    closing the concentrated red blood cell output port when the separation channel is substantially filled with plasma;
    after the step of closing the concentrated red blood cell output port, closing the first plasma output port;
    after the step of closing the first plasma output port, continuing to operate the centrifuge at a moderate speed while introducing a gas into the separation channel to create a purge plasma flow;
    simultaneously with the continuing to operate the centrifuge at moderate speed;
    opening the second plasma output port and directing purge plasma flow through the second plasma output port into the plasma collection bag.

2. The method of claim 1, wherein the step of operating the centrifuge further comprises the steps of:
    operating the centrifuge to form a buffy coat interface between the flow the red cells and the flow of plasma in the separation channel; and
    selectively controlling the anticoagulated blood flow to the separation channel, the flow of red concentrated blood cells from the separation channel and the flow of plasma from the separation channel to maintain the buffy coat interface at a selected point near the center of the separation channel;
    after the step of continuing to operate the centrifuge at moderate speed, stopping operation of the centrifuge while a portion of the buffy coat interface remains in the separation channel.

3. The method of claim 1, wherein the step of operating the centrifuge further comprises the steps of:
    operating the centrifuge to form a buffy coat interface between the flow the red cells and the flow of plasma in the separation channel; and
    selectively controlling the anticoagulated blood flow to the separation channel, the flow of red concentrated blood cells from the separation channel and the flow of plasma from the separation channel to maintain the buffy coat interface at a selected point near the center of the separation channel;
    simultaneously with the step of continuing to operate the centrifuge at moderate speed, monitoring the plasma flow to determine when substantially only the buffy coat interface is left in the separation channel;
    when substantially only the buffy coat interface is left in the separation channel, directing the buffy coat interface through the second plasma output port into a buffy coat collection bag.

4. The method of claim 1, wherein the step of operating the centrifuge further comprises the steps of:
    operating the centrifuge to form a buffy coat interface between the flow the red cells and the flow of plasma in the separation channel; and
    selectively controlling the anticoagulated blood flow to the separation channel, the flow of red concentrated blood cells from the separation channel and the flow of plasma from the separation channel to maintain the buffy coat interface at a selected point near the center of the separation channel;
    simultaneously with the step of continuing to operate the centrifuge at moderate speed, monitoring the plasma flow to determine when substantially only the buffy coat interface is left in the separation channel;

when substantially only the buffy coat interface is left in the separation channel, closing the second plasma output port, opening the concentrated red blood cell output port, and directing the buffy coat interface through the red blood cell output port into a buffy coat collection bag.

5. The method of claim 4, further comprising the step of:
filtering the flow of red blood cells in a leukofilter after the step of introducing red cell storage solution and before the step of directing the flow of red blood cells into a red blood cell collection bag; and the step of directing the buffy coat interface through the red blood cell output port into a buffy coat collection bag further comprises the step of preventing the buffy coat from entering the leukofilter.

6. A method of simultaneous blood collection and separation using a continuous flow centrifuge having a separation channel, a blood input port, a concentrated red blood cell output port, a first plasma output port, and a second plasma output port, comprising the steps of:
collecting blood from a donor to form a blood flow;
simultaneously with the collecting step adding an anticoagulant to the blood flow to form an anticoagulated blood flow;
simultaneously with the adding step, introducing the anticoagulated blood flow into the separation channel through the blood input port while keeping the blood input port open;
simultaneously with the introducing step, operating the centrifuge to produce a flow of concentrated red blood cells and a flow of plasma from the anticoagulated blood flow;
simultaneously with the operating step, directing the flow of plasma from the separation channel through the first plasma output port into a plasma collection bag while keeping the first plasma output port open;
simultaneously with the operating step, directing the flow of concentrated red blood cells from the separation channel through the red blood cell output port into a fluid transportation means while keeping the red blood cell output port open;
simultaneously with the operating step, introducing red cell storage solution into the flow of concentrated red blood cells in the fluid transportation means;
simultaneously with the operating step, directing the flow of concentrated red blood cells from the fluid transportation means into a red blood cell collection bag;
keeping the second plasma output port closed while the first plasma output port is open;
at the occurrence of a preselected event, closing the blood input port to prevent the anticoagulated blood flow from entering the separation channel;
after the closing step, continuing to operate the centrifuge at a moderate speed while introducing a gas into the separation channel to create a purge plasma flow;
simultaneously with the step of introducing a gas into the separation channel, continuing operation of the centrifuge to produce a flow of concentrated red blood cells;
simultaneously with the continuing operation step, directing the flow of concentrated red blood cells from the separation channel into a fluid transportation means while keeping the concentrated red blood cell output port open;
closing the concentrated red blood cell output port;
simultaneously with the step of continuing operation; opening the second plasma output port and directing purge plasma flow through the second plasma output port into the plasma collection bag.

7. A method of simultaneous blood collection and separation using a continuous flow centrifuge having a separation channel, a blood input port, a concentrated red blood cell output port, and a first plasma output port, comprising the steps of:
collecting blood from a donor to form a blood flow;
simultaneously with the collecting step adding an anticoagulant to the blood flow to form an anticoagulated blood flow;
simultaneously with the adding step, introducing the anticoagulated blood flow into the separation channel through the blood input port while keeping the blood input port open;
simultaneously with the introducing step, operating the centrifuge to produce a flow of concentrated red blood cells and a flow of plasma from the anticoagulated blood flow;
simultaneously with the operating step, directing the flow of plasma from the separation channel through the first plasma output port into a plasma collection bag while keeping the first Plasma output port open;
simultaneously with the operating step, directing the flow of concentrated red blood cells from the separation channel through the red blood cell output port into a fluid transportation means while keeping the red blood cell output port open;
simultaneously with the operating step, introducing red cell storage solution into the flow of concentrated red blood cells in the fluid transportation means;
simultaneously with the operating step, directing the flow of concentrated red blood cells from the fluid transportation means into a red blood cell collection bag,
at the occurrence of a preselected event, controlling the flow of concentrated red blood cells to allow the separation channel to fill with concentrated red blood cells and simultaneously removing all plasma from the separation channel;
after the controlling step and when the separation channel is filled with concentrated red blood cells, continuing to operate the centrifuge at a moderate speed while introducing a gas into the separation channel to force the concentrated red blood cells from the channel;
simultaneously with the step of introducing a gas into the separation channel, continuing operation of the centrifuge to produce a flow of concentrated red blood cells;
simultaneously with the continuing operation step, directing the flow of concentrated red blood cells from the separation channel into a fluid transportation means while keeping the concentrated red blood cell output port open.

8. A method of simultaneous blood collection and separation using a continuous flow centrifuge having a separation channel, a blood input port, a concentrated red blood cell output port, and a first plasma output port, comprising the steps of:
collecting blood from a donor to form a blood flow;
simultaneously with the collecting step adding an anticoagulant to the blood flow to form an anticoagulated blood flow;
simultaneously with the adding step, introducing the anticoagulated blood flow into the separation channel through the blood input port while keeping the blood input port open;

simultaneously with the introducing step, operating the centrifuge to produce a flow of concentrated red blood cells and a flow of plasma from the anticoagulated blood flow;

simultaneously with the operating step, directing the flow of plasma from the separation channel through the first plasma output port into a plasma collection bag while keeping the first plasma output port open;

simultaneously with the operating step, directing the flow of concentrated red blood cells from the separation channel through the red blood cell output port into a fluid transportation means while keeping the red blood cell output port open;

simultaneously with the operating step, introducing red cell storage solution into the flow of concentrated red blood cells in the fluid transportation means;

simultaneously with the operating step, directing the flow of concentrated red blood cells from the fluid transportation means into a red blood cell collection bag, at the occurrence of a preselected event, controlling the flow of concentrated red blood cells to allow the separation channel to fill with concentrated red blood cells and simultaneously removing all plasma from the separation channel;

after the controlling step and when the separation channel is filled with concentrated red blood cells, continuing to operate the centrifuge at a moderate speed while introducing anticoagulant into the separation channel to force the concentrated red blood cells from the channel;

simultaneously with the step of introducing anticoagulant into the separation channel, continuing operation of the centrifuge to produce a flow of concentrated red blood cells;

simultaneously with the continuing operation step, directing the flow of concentrated red blood cells from the separation channel into a fluid transportation means while keeping the concentrated red blood cell output port open.

9. The method of claim 1 wherein step of directing purge plasma flow through the second plasma output port into the plasma collection bag further includes the step of pumping the purge plasma flow into the plasma collection bag.

10. The method of claim 3 wherein step of directing purge plasma flow through the second plasma output port into the plasma collection bag further includes the step of pumping the purge plasma flow into the plasma collection bag; and
the step of directing the buffy coat interface further includes the step of pumping the buffy coat interface into the buffy coat collection bag.

11. The method of claim 4 wherein step of directing purge plasma flow through the second plasma output port into the plasma collection bag further includes the step of pumping the purge plasma flow into the plasma collection bag; and
the step of directing the buffy coat interface further includes the step of pumping the buffy coat interface into the buffy coat collection bag.

12. The method of claim 6 wherein step of directing purge plasma flow through the second plasma output port into the plasma collection bag further includes the step of pumping the purge plasma flow into the plasma collection bag.

13. The method of claim 1 further comprising the steps of:
prior to the adding step, determining the value of the hemocrit of the blood;
prior to the adding step, selecting a volume of concentrated red cells to be collected;
simultaneously with the step of directing the flow of concentrated red blood cells, monitoring the flow of concentrated red blood cells and calculating a value representing the concentrated red blood cells collected using the value of the hemocrit;
and wherein the occurrence of the preselected event is determined by the steps of:
comparing the value representing the concentrated red blood cells collected with the volume of concentrated red blood cells to be collected.

14. The method of claim 3 further comprising the steps of:
prior to the adding step, determining the value of the hemocrit of the blood;
prior to the adding step, selecting a volume of concentrated red cells to be collected;
simultaneously with the step of directing the flow of concentrated red blood cells, monitoring the flow of concentrated red blood cells and calculating a value representing the concentrated red blood cells collected using the value of the hemocrit;
and wherein the occurrence of the preselected event is determined by the step of:
comparing the value representing the concentrated red blood cells collected with the volume of concentrated red blood cells to be collected.

15. The method of claim 4 further comprising the steps of:
prior to the adding step, determining the value of the hemocrit of the blood;
prior to the adding step, selecting a volume of concentrated red cells to be collected;
simultaneously with the step of directing the flow of concentrated red blood cells, monitoring the flow of concentrated red blood cells and calculating a value representing the concentrated red blood cells collected using the value of the hemocrit;
and wherein the occurrence of the preselected event is determined by the step of:
comparing the value representing the concentrated red blood cells collected with the volume of concentrated red blood cells to be collected.

16. The method of claim 6 further comprising the steps of:
prior to the adding step, determining the value of the hemocrit of the blood;
prior to the adding step, selecting a volume of concentrated red cells to be collected;
simultaneously with the step of directing the flow of concentrated red blood cells, monitoring the flow of concentrated red blood cells and calculating a value representing the concentrated red blood cells collected using the value of the hemocrit;
and wherein the occurrence of the preselected event is determined by the step of:
comparing the value representing the concentrated red blood cells collected with the volume of concentrated red blood cells to be collected.

17. The method of claim 7 further comprising the steps of:
prior to the adding step, determining the value of the hemocrit of the blood;
prior to the adding step, selecting a volume of concentrated red cells to be collected;
simultaneously with the step of directing the flow of concentrated red blood cells, monitoring the flow of concentrated red blood cells and calculating a value representing the concentrated red blood cells collected using the value of the hemocrit;
and wherein the occurrence of the preselected event is determined by the step of:

comparing the value representing the concentrated red blood cells collected with the volume of concentrated red blood cells to be collected.

18. The method of claim 8 further comprising the steps of:
prior to the adding step, determining the value of the hemocrit of the blood;
prior to the adding step, selecting a volume of concentrated red cells to be collected;
simultaneously with the step of directing the flow of concentrated red blood cells, monitoring the flow of concentrated red blood cells and calculating a value representing the concentrated red blood cells collected using the value of the hemocrit;
and wherein the occurrence of the preselected event is determined by the step of:
comparing the value representing the concentrated red blood cells collected with the volume of concentrated red blood cells to be collected.

19. The method of claim 7 further comprising the steps of:
prior to the adding step, selecting a volume of blood to be collected;
simultaneously with the step of directing the flow of concentrated red blood cells, monitoring the blood flow and calculating a value representing the volume of blood collected;
and wherein the occurrence of the preselected event is determined by the steps of:
comparing the value representing the blood collected with the volume of blood to be collected.

20. The method of claim 8 further comprising the steps of:
prior to the adding step, selecting a volume of blood to be collected;
simultaneously with the step of directing the flow of concentrated red blood cells, monitoring the blood flow and calculating a value representing the volume of blood collected;
and wherein the occurrence of the preselected event is determined by the steps of:
comparing the value representing the blood collected with the volume of blood to be collected.

21. The method of claim 3 further comprising the steps of:
prior to the adding step, selecting a volume of blood to be collected;
simultaneously with the step of directing the flow of concentrated red blood cells, monitoring the blood flow and calculating a value representing the volume of blood collected;
and wherein the occurrence of the preselected event is determined by the steps of:
comparing the value representing the blood collected with the volume of blood to be collected.

22. The method of claim 4 further comprising the steps of:
prior to the adding step, selecting a volume of blood to be collected;
simultaneously with the step of directing the flow of concentrated red blood cells, monitoring the blood flow and calculating a value representing the volume of blood collected;
and wherein the occurrence of the preselected event is determined by the steps of:
comparing the value representing the blood collected with the volume of blood to be collected.

23. The method of claim 6 further comprising the steps of:
prior to the adding step, selecting a volume of blood to be collected;
simultaneously with the step of directing the flow of concentrated red blood cells, monitoring the blood flow and calculating a value representing the volume of blood collected;
and wherein the occurrence of the preselected event is determined by the steps of:
comparing the value representing the blood collected with the volume of blood to be collected.

24. The method of claim 14 wherein the monitoring step further comprises:
calculating a value representing the volume of flow of the concentrated red blood cells per unit time using the value of the hemocrit; and wherein the method further comprises the steps of:
determining a maximum value for the volume of the concentrated red blood cells per unit time; and
reducing the blood flow when the value representing the volume of flow of the concentrated red blood cells per unit time exceeds the maximum value.

25. The method of claim 15 wherein the monitoring step further comprises:
calculating a value representing the volume of flow of the concentrated red blood cells per unit time using the value of the hemocrit; and wherein the method further comprises the steps of:
determining a maximum value for the volume of the concentrated red blood cells per unit time; and
reducing the blood flow when the value representing the volume of flow of the concentrated red blood cells per unit time exceeds the maximum value.

26. The method of claim 16 wherein the monitoring step further comprises:
calculating a value representing the volume of flow of the concentrated red blood cells per unit time using the value of the hemocrit; and wherein the method further comprises the steps of:
determining a maximum value for the volume of the concentrated red blood cells per unit time; and
reducing the blood flow when the value representing the volume of flow of the concentrated red blood cells per unit time exceeds the maximum value.

27. The method of claim 24 wherein the step of directing the flow of concentrated red blood cells further comprises the step of pumping the concentrated red blood cells from the fluid transportation means into a concentrated red blood cell collection bag; and the step of directing the flow of plasma to a plasma collection bag further includes the step of pumping the plasma into the plasma collection bag; and wherein the step of reducing the blood flow further comprises:
selectively reducing pumping the flow of plasma; and
selectively reducing pumping the flow of concentrated red blood cells.

28. The method of claim 25 wherein the step of directing the flow of concentrated red blood cells further comprises the step of pumping the concentrated red blood cells from the fluid transportation means into a concentrated red blood cell collection bag; and the step of directing the flow of plasma to a plasma collection bag further includes the step of pumping the plasma into the plasma collection bag; and wherein the step of reducing the blood flow further comprises:
selectively reducing pumping the flow of plasma; and
selectively reducing pumping the flow of concentrated red blood cells.

29. The method of claim 26 wherein the step of directing the flow of concentrated red blood cells further comprises the step of pumping the concentrated red blood cells from the fluid transportation means into a concentrated red blood cell collection bag; and the step of directing the flow of plasma to a plasma collection bag further includes the step of pumping the plasma into the plasma collection bag; and wherein the step of reducing the blood flow further comprises:

selectively reducing pumping the flow of plasma; and
    selectively reducing pumping the flow of concentrated red blood cells.

30. The method of claim 24 wherein the step of collecting blood further comprises the step of pumping blood from the donor; and wherein the step of reducing the blood flow further comprises:

selectively reducing pumping the blood from the donor.

31. The method of claim 25 wherein the step of collecting blood further comprises the step of pumping blood from the donor; and wherein the step of reducing the blood flow further comprises:

selectively reducing pumping the blood from the donor.

32. The method of claim 26 wherein the step of collecting blood further comprises the step of pumping blood from the donor; and wherein the step of reducing the blood flow further comprises:

selectively reducing pumping the blood from the donor.

\* \* \* \* \*